US011925723B2

(12) United States Patent
Dehnad et al.

(10) Patent No.: US 11,925,723 B2
(45) Date of Patent: *Mar. 12, 2024

(54) BONE IMPLANT AND SYSTEMS AND COATINGS FOR THE CONTROLLABLE RELEASE OF ANTIMICROBIAL METAL IONS

(71) Applicant: Silver Bullet Therapeutics, Inc., San Jose, CA (US)

(72) Inventors: Houdin Dehnad, El Granada, CA (US); Paul E. Chirico, Campbell, CA (US); Bohdan Wolodymyr Chopko, Henderson, NV (US); John Barr, San Diego, CA (US); Robert Vincent McCormick, Saratoga, CA (US); Julie Lucero, San Jose, CA (US); Jason A. Jegge, San Jose, CA (US)

(73) Assignee: Silver Bullet Therapeutics, Inc., San Jose, CA (US)

( * ) Notice: Subject to any disclaimer, the term of this patent is extended or adjusted under 35 U.S.C. 154(b) by 68 days.

This patent is subject to a terminal disclaimer.

(21) Appl. No.: 17/336,246

(22) Filed: Jun. 1, 2021

(65) Prior Publication Data

US 2021/0283303 A1 Sep. 16, 2021

Related U.S. Application Data

(60) Continuation of application No. 16/391,195, filed on Apr. 22, 2019, now Pat. No. 11,020,508, which is a
(Continued)

(51) Int. Cl.
*A61L 27/54* (2006.01)
*A01N 25/34* (2006.01)
(Continued)

(52) U.S. Cl.
CPC .............. *A61L 27/18* (2013.01); *A01N 25/34* (2013.01); *A61K 33/24* (2013.01); *A61K 33/242* (2019.01);
(Continued)

(58) Field of Classification Search
CPC ......... A61B 17/54; A61B 17/58; A61B 17/80; A61B 17/84; A61B 17/86; A61L 27/54
See application file for complete search history.

(56) References Cited

U.S. PATENT DOCUMENTS 2,998,007 A 8/1961 Herzog
3,921,632 A 11/1975 Bardani
(Continued)

FOREIGN PATENT DOCUMENTS

DE 102006004628 A1 8/2007
WO WO 99/44538 A1 9/1999
(Continued)

OTHER PUBLICATIONS

Kang et al; Effect of a combination of low level ozone and metal ions on reducing *Escherichia coli* 0157:H7 and listeria monocytogenes; Molecules; 18(4); pp. 4018-4025; Apr. 4, 2013.

*Primary Examiner* — Nicholas W Woodall
(74) *Attorney, Agent, or Firm* — Shay Glenn LLP

(57) ABSTRACT

Antimicrobial metal ion coatings and implants including them. In particular, described herein are coatings including an anodic metal (e.g., silver and/or zinc and/or copper) that is co-deposited with a cathodic metal (e.g., palladium, platinum, gold, molybdenum, titanium, iridium, osmium, rhodium, manganese, niobium or rhenium) on a substrate so that the anodic metal is galvanically released as antimicrobial ions when the apparatus is exposed to a bodily fluid. The anodic metal may be at least about 25 percent by volume of the coating, resulting in a network of anodic metal with less
(Continued)

than 20% of the anodic metal in the coating fully encapsulated by cathodic metal. The implant may be configured as an implant such as a bone-screw or intramedullary rod-like body configured to receive a treatment cartridge having a coating as described.

17 Claims, 27 Drawing Sheets

Related U.S. Application Data continuation of application No. 15/820,393, filed on Nov. 21, 2017, now Pat. No. 10,265,435, which is a continuation-in-part of application No. 14/833,569, filed on Aug. 24, 2015, now Pat. No. 9,821,094, which is a continuation-in-part of application No. 14/679,893, filed on Apr. 6, 2015, now Pat. No. 9,114,197, which is a continuation-in-part of application No. 14/569,545, filed on Dec. 12, 2014, now Pat. No. 8,999,367, which is a continuation of application No. 14/302,352, filed on Jun. 11, 2014, now Pat. No. 8,927,004, said application No. 15/820,393 is a continuation-in-part of application No. 14/801,732, filed on Jul. 16, 2015, now Pat. No. 9,889,284, which is a continuation of application No. 13/748,546, filed on Jan. 23, 2013, now Pat. No. 9,108,051, which is a division of application No. 13/231,219, filed on Sep. 13, 2011, now Pat. No. 8,771,323, said application No. 14/801,732 is a continuation-in-part of application No. 13/527,389, filed on Jun. 19, 2012, now Pat. No. 9,248,254, which is a continuation of application No. 12/870,082, filed on Aug. 27, 2010, now Pat. No. 8,221,396.

(60) Provisional application No. 62/059,714, filed on Oct. 3, 2014, provisional application No. 61/413,230, filed on Nov. 12, 2010, provisional application No. 61/438,162, filed on Jan. 31, 2011, provisional application No. 61/447,393, filed on Feb. 28, 2011, provisional application No. 61/465,350, filed on Mar. 18, 2011, provisional application No. 61/516,388, filed on Apr. 4, 2011, provisional application No. 61/237,506, filed on Aug. 27, 2009, provisional application No. 61/340,587, filed on Mar. 19, 2010, provisional application No. 61/359,549, filed on Jun. 29, 2010.

(51) Int. Cl.
| | | |
|---|---|---|
| *A61B 17/54* | (2006.01) | |
| *A61B 17/58* | (2006.01) | |
| *A61B 17/80* | (2006.01) | |
| *A61B 17/84* | (2006.01) | |
| *A61B 17/86* | (2006.01) | |
| *A61K 33/24* | (2019.01) | |
| *A61K 33/242* | (2019.01) | |
| *A61K 33/243* | (2019.01) | |
| *A61K 33/30* | (2006.01) | |
| *A61K 33/38* | (2006.01) | |
| *A61L 27/18* | (2006.01) | |
| *A61L 27/30* | (2006.01) | |
| *A61L 27/58* | (2006.01) | |
| *A61L 29/10* | (2006.01) | |
| *A61L 29/16* | (2006.01) | |
| *A61L 31/06* | (2006.01) | |
| *A61L 31/08* | (2006.01) | |
| *A61L 31/14* | (2006.01) | |
| *A61L 31/16* | (2006.01) | |
| *C08L 67/04* | (2006.01) | |

(52) U.S. Cl.
CPC ............ *A61K 33/243* (2019.01); *A61K 33/30* (2013.01); *A61K 33/38* (2013.01); *A61L 27/306* (2013.01); *A61L 27/54* (2013.01); *A61L 27/58* (2013.01); *A61L 29/106* (2013.01); *A61L 29/16* (2013.01); *A61L 31/06* (2013.01); *A61L 31/088* (2013.01); *A61L 31/148* (2013.01); *A61L 31/16* (2013.01); *C08L 67/04* (2013.01); *A61L 2300/102* (2013.01); *A61L 2300/104* (2013.01); *A61L 2300/404* (2013.01); *A61L 2300/602* (2013.01); *A61L 2300/604* (2013.01); *A61L 2300/606* (2013.01); *A61L 2400/18* (2013.01); *A61L 2420/06* (2013.01)

(56) References Cited

U.S. PATENT DOCUMENTS

| | | |
|---|---|---|
| 4,292,968 A | 10/1981 | Ellis |
| 4,314,554 A | 2/1982 | Greatbatch |
| 4,405,311 A | 9/1983 | Greatbatch |
| 4,615,705 A | 10/1986 | Scales et al. |
| 4,772,266 A | 9/1988 | Groshong |
| 4,849,223 A | 7/1989 | Pratt et al. |
| 5,290,271 A | 3/1994 | Jernberg |
| 5,372,599 A | 12/1994 | Martins |
| 5,383,935 A | 1/1995 | Shirkhanzadeh |
| 5,423,859 A | 6/1995 | Koyfman et al. |
| 5,454,886 A | 10/1995 | Burrell et al. |
| 5,505,735 A | 4/1996 | Li |
| 5,510,109 A | 4/1996 | Tomioka et al. |
| 5,549,603 A | 8/1996 | Feiring |
| 5,681,575 A | 10/1997 | Burrell et al. |
| 5,695,857 A | 12/1997 | Burrell et al. |
| 5,714,047 A | 2/1998 | Pedrazzini |
| 5,725,377 A | 3/1998 | Lemler et al. |
| 5,770,255 A | 6/1998 | Burrell et al. |
| 5,788,687 A | 8/1998 | Batich et al. |
| 5,958,440 A | 9/1999 | Burrell et al. |
| 5,985,308 A | 11/1999 | Burrell et al. |
| 6,080,490 A | 6/2000 | Burrell et al. |
| 6,117,296 A | 9/2000 | Thomson |
| 6,287,484 B1 | 9/2001 | Hausslein et al. |
| 6,312,469 B1 | 11/2001 | Gielen et al. |
| 6,425,887 B1 | 7/2002 | McGuckin et al. |
| 6,447,513 B1 | 9/2002 | Griggs |
| 6,451,003 B1 | 9/2002 | Prosi et al. |
| 6,458,092 B1 | 10/2002 | Gambale et al. |
| 6,458,889 B1 | 10/2002 | Trollsas et al. |
| 6,478,790 B2 | 11/2002 | Bardani |
| 6,500,165 B1 | 12/2002 | Frank |
| 6,522,918 B1 | 2/2003 | Crisp et al. |
| 6,558,388 B1 | 5/2003 | Bartsch et al. |
| 6,613,807 B2 | 9/2003 | Uhrich |
| 6,616,678 B2 | 9/2003 | Nishtala et al. |
| 6,716,895 B1 | 4/2004 | Terry |
| 6,719,987 B2 | 4/2004 | Burrell et al. |
| 6,773,429 B2 | 8/2004 | Sheppard, Jr. et al. |
| 6,830,747 B2 | 12/2004 | Lang et al. |
| 6,840,919 B1 | 1/2005 | Håkansson |
| 6,913,763 B2 | 7/2005 | Lemer |
| 6,936,006 B2 | 8/2005 | Sabra |
| 6,936,270 B2 | 8/2005 | Watson et al. |
| 6,960,215 B2 | 11/2005 | Olson, Jr. et al. |
| 7,147,865 B2 | 12/2006 | Fishman et al. |
| 7,179,849 B2 | 2/2007 | Terry |
| 7,223,227 B2 | 5/2007 | Pflueger |
| 7,255,713 B2 | 8/2007 | Malek |
| 7,456,012 B2 | 11/2008 | Rytténn et al. |
| 7,457,667 B2 | 11/2008 | Skiba |
| 7,632,277 B2 | 12/2009 | Woll et al. |

(56) References Cited

U.S. PATENT DOCUMENTS

| | | | |
|---|---|---|---|
| 7,662,176 B2 | 2/2010 | Skiba et al. |
| 7,672,719 B2 | 3/2010 | Skiba et al. |
| 7,704,520 B1 | 4/2010 | Calhoun |
| 7,727,221 B2 | 6/2010 | Penner et al. |
| 7,824,699 B2 | 11/2010 | Ralph et al. |
| 7,846,162 B2 | 12/2010 | Nelson |
| 7,904,147 B2 | 3/2011 | Schneider et al. |
| 7,919,111 B2 | 4/2011 | Chudzik et al. |
| 7,951,853 B2 | 5/2011 | Ismail et al. |
| 7,955,636 B2 | 6/2011 | Terry |
| 7,985,415 B2 | 7/2011 | Giroux |
| 8,048,150 B2 | 11/2011 | Weber et al. |
| 8,052,743 B2 | 11/2011 | Weber et al. |
| 8,080,055 B2 | 12/2011 | Atanasoska et al. |
| 8,114,148 B2 | 2/2012 | Atanasoska et al. |
| 8,118,857 B2 | 2/2012 | VanCamp et al. |
| 8,178,120 B2 | 5/2012 | Vandesteeg et al. |
| 8,221,396 B2 | 7/2012 | Dehnad et al. |
| 8,236,046 B2 | 8/2012 | Weber |
| 8,267,992 B2 | 9/2012 | Atanasoska et al. |
| 8,292,932 B2 | 10/2012 | Matthis et al. |
| 8,309,216 B2 | 11/2012 | Ohrlander et al. |
| 8,591,531 B2 | 11/2013 | Buevich et al. |
| 8,636,753 B2 | 1/2014 | Buevich et al. |
| 8,771,323 B2 | 7/2014 | Dehnad et al. |
| 8,927,004 B1 | 1/2015 | Dehnad et al. |
| 8,999,367 B1 | 4/2015 | Dehnad et al. |
| 9,108,051 B2 | 8/2015 | Dehnad et al. |
| 9,114,197 B1 | 8/2015 | Dehnad et al. |
| 9,248,254 B2 | 2/2016 | Dehnad et al. |
| 9,452,242 B2 | 9/2016 | Dehnad et al. |
| 9,789,298 B2 | 10/2017 | Dehnad et al. |
| 9,821,094 B2 | 11/2017 | Dehnad et al. |
| 9,889,284 B2 | 2/2018 | Dehnad et al. |
| 10,004,548 B2 | 6/2018 | Dehnad et al. |
| 10,265,435 B2 | 4/2019 | Dehnad et al. |
| 11,020,508 B2 | 6/2021 | Dehnad et al. |
| 11,224,471 B2 | 1/2022 | Dehnad et al. |
| 11,317,955 B2* | 5/2022 | Sfeir ............... A61B 17/8625 |
| 2002/0029043 A1 | 3/2002 | Ahrens et al. |
| 2002/0031601 A1 | 3/2002 | Darouiche et al. |
| 2002/0082679 A1 | 6/2002 | Sirhan et al. |
| 2002/0111603 A1 | 8/2002 | Cheikh |
| 2002/0143302 A1 | 10/2002 | Hinchliffe et al. |
| 2003/0050689 A1 | 3/2003 | Matson |
| 2003/0065292 A1 | 4/2003 | Darouiche et al. |
| 2004/0039441 A1 | 2/2004 | Rowland et al. |
| 2004/0223944 A1 | 11/2004 | Capelli |
| 2004/0267234 A1 | 12/2004 | Heart et al. |
| 2005/0004558 A1 | 1/2005 | Gambale et al. |
| 2005/0125054 A1 | 6/2005 | Bhat et al. |
| 2005/0152949 A1 | 7/2005 | Hotchkiss et al. |
| 2005/0177103 A1 | 8/2005 | Hunter et al. |
| 2005/0181004 A1 | 8/2005 | Hunter et al. |
| 2005/0256525 A1 | 11/2005 | Culbert et al. |
| 2005/0271701 A1 | 12/2005 | Cottone et al. |
| 2006/0004431 A1 | 1/2006 | Fuller et al. |
| 2006/0030872 A1 | 2/2006 | Culbert et al. |
| 2006/0041182 A1 | 2/2006 | Forbes et al. |
| 2006/0264698 A1 | 11/2006 | Kondonis et al. |
| 2007/0016163 A1 | 1/2007 | Santini et al. |
| 2007/0141106 A1 | 6/2007 | Bonutti et al. |
| 2007/0168012 A1 | 7/2007 | Ragheb et al. |
| 2007/0179609 A1 | 8/2007 | Goble et al. |
| 2007/0244548 A1 | 10/2007 | Myers et al. |
| 2007/0260054 A1 | 11/2007 | Chudzik |
| 2007/0298377 A1* | 12/2007 | Kenealy ............... A61C 8/0012 433/201.1 |
| 2008/0009888 A1 | 1/2008 | Ewers et al. |
| 2008/0058733 A1 | 3/2008 | Vogt et al. |
| 2008/0109034 A1 | 5/2008 | Mather et al. |
| 2008/0147186 A1 | 6/2008 | Joshi et al. |
| 2008/0195033 A1 | 8/2008 | Eagleson et al. |
| 2008/0195223 A1 | 8/2008 | Eddin et al. |
| 2008/0255618 A1 | 10/2008 | Fisher et al. |
| 2008/0319424 A1 | 12/2008 | Muni et al. |
| 2009/0004239 A1 | 1/2009 | Ladet et al. |
| 2009/0005867 A1 | 1/2009 | Lefranc et al. |
| 2009/0005869 A1 | 1/2009 | Laurencin et al. |
| 2009/0012350 A1 | 1/2009 | Tihon |
| 2009/0035342 A1 | 2/2009 | Karandikar et al. |
| 2009/0036744 A1 | 2/2009 | Vayser |
| 2009/0099613 A1 | 4/2009 | Vilims |
| 2009/0112236 A1 | 4/2009 | Stopek |
| 2009/0198286 A1* | 8/2009 | Lozier ............... A61B 17/80 606/301 |
| 2009/0204129 A1 | 8/2009 | Fronio |
| 2009/0248048 A1 | 10/2009 | Milbocker |
| 2010/0076463 A1 | 3/2010 | Mavani et al. |
| 2010/0092531 A1 | 4/2010 | Odermatt et al. |
| 2010/0131051 A1 | 5/2010 | Peterson |
| 2010/0217370 A1 | 8/2010 | Scheuermann et al. |
| 2010/0249783 A1 | 9/2010 | Triue |
| 2010/0292756 A1* | 11/2010 | Schneider ............... A61N 1/326 607/50 |
| 2010/0326835 A1 | 12/2010 | Speitling |
| 2010/0331966 A1 | 12/2010 | Borck |
| 2011/0091515 A1 | 4/2011 | Zilberman et al. |
| 2011/0125287 A1 | 5/2011 | Hotter et al. |
| 2011/0130774 A1 | 6/2011 | Criscuolo et al. |
| 2011/0153027 A1 | 6/2011 | Behan |
| 2011/0200655 A1 | 8/2011 | Black et al. |
| 2011/0257666 A1 | 10/2011 | Ladet et al. |
| 2012/0148633 A1 | 6/2012 | Sun et al. |
| 2012/0251592 A1 | 10/2012 | Neff et al. |
| 2012/0323220 A1 | 12/2012 | Mackay et al. |
| 2013/0005829 A1 | 1/2013 | Jamiolkowski et al. |
| 2013/0018448 A1 | 1/2013 | Folan et al. |
| 2013/0045266 A1 | 2/2013 | Choi et al. |
| 2013/0158571 A1 | 6/2013 | Meneghin et al. |
| 2013/0164346 A1 | 6/2013 | Lee et al. |
| 2013/0172915 A1 | 7/2013 | Thomas et al. |
| 2013/0224276 A1 | 8/2013 | Hunter et al. |
| 2013/0245783 A1 | 9/2013 | Thull |
| 2013/0295184 A1 | 11/2013 | Choi et al. |
| 2017/0224458 A1* | 8/2017 | García Martín ....... A61C 13/00 |
| 2017/0239398 A1 | 8/2017 | Sfeir et al. |
| 2017/0312399 A1 | 11/2017 | Dehnad et al. |
| 2018/0296262 A1 | 10/2018 | Dehnad et al. |
| 2022/0133376 A1 | 5/2022 | Dehnad et al. |

FOREIGN PATENT DOCUMENTS

| | | |
|---|---|---|
| WO | WO 00/47273 A1 | 8/2000 |
| WO | WO 00/51659 A1 | 9/2000 |
| WO | WO 02/009767 A2 | 2/2002 |
| WO | WO 03/049798 A2 | 6/2003 |
| WO | WO 2004/006885 A2 | 1/2004 |
| WO | WO 2004/026357 A1 | 4/2004 |
| WO | WO 2004/045549 A2 | 6/2004 |
| WO | WO2004/059027 A2 | 7/2004 |
| WO | WO 2005/049105 A2 | 6/2005 |
| WO | WO2005/051448 A1 | 6/2005 |
| WO | WO 2006/135479 A2 | 12/2006 |
| WO | WO 2007/076376 A2 | 7/2007 |
| WO | WO2007/097790 A1 | 8/2007 |
| WO | WO 2007/109069 A2 | 9/2007 |
| WO | WO 2007/117214 A1 | 10/2007 |
| WO | WO2009/158333 A2 | 12/2009 |
| WO | WO2010/111502 A2 | 9/2010 |
| WO | WO 2011/031789 A1 | 3/2011 |
| WO | WO 2011/127149 A1 | 10/2011 |
| WO | WO 2013/004727 A1 | 1/2013 |
| WO | WO 2013/049106 A2 | 4/2013 |
| WO | WO 2013/049799 A1 | 4/2013 |
| WO | WO 2013/114145 A1 | 8/2013 |

\* cited by examiner

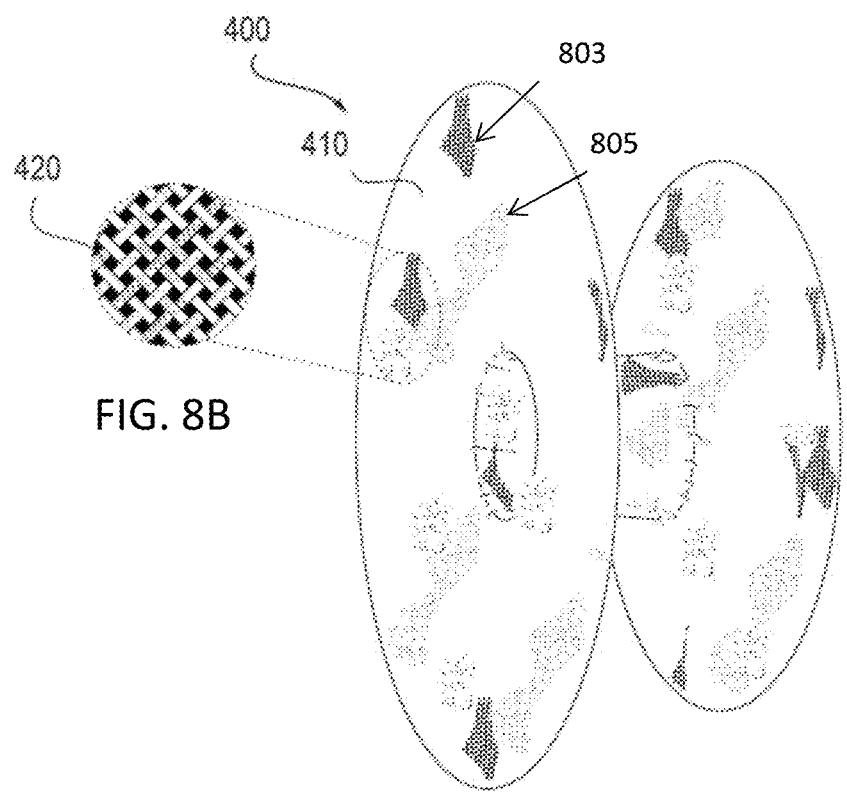
FIG. 8B
FIG. 8A
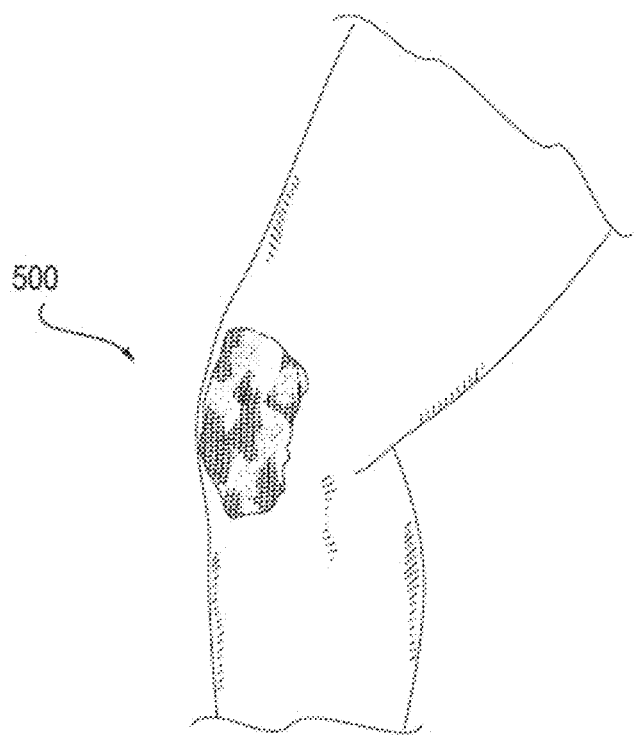
FIG. 9

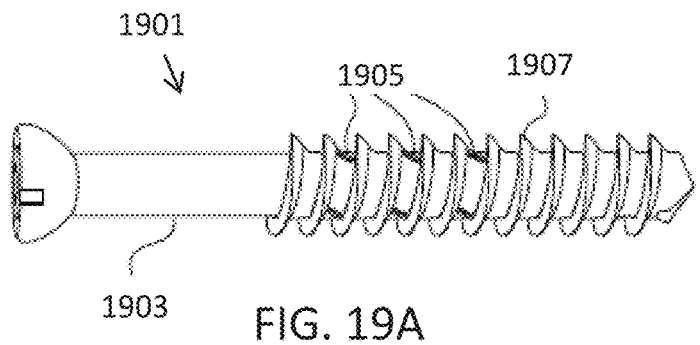
FIG. 19A
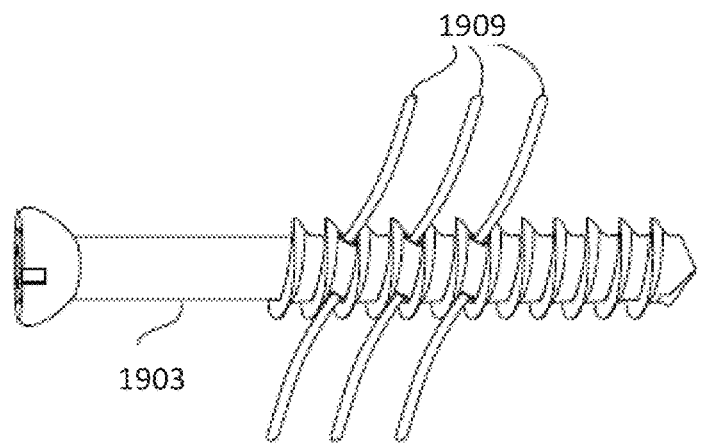
FIG. 19B
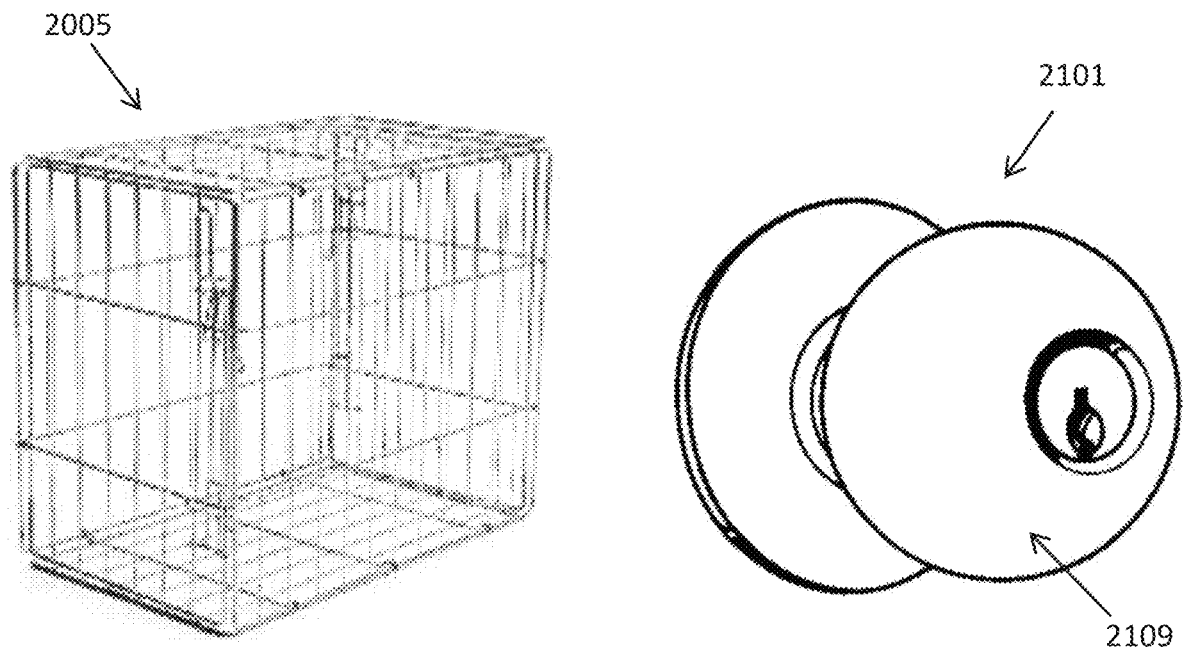
FIG. 20
FIG. 21

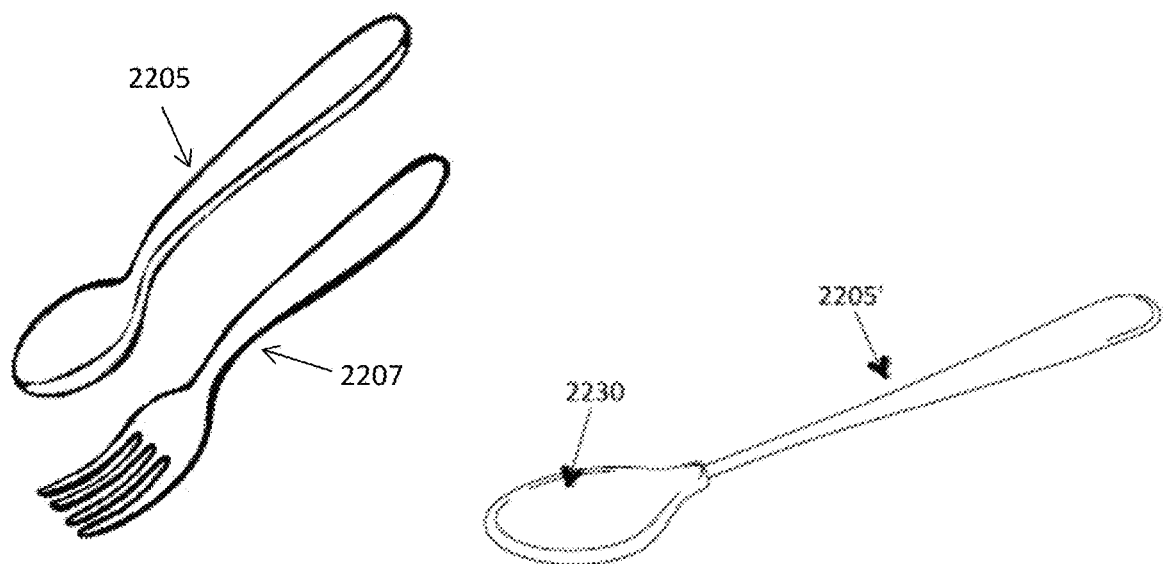
FIG. 22A
FIG. 22B
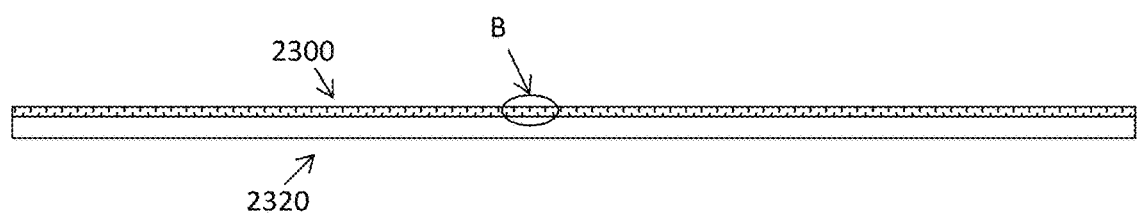
FIG. 23A
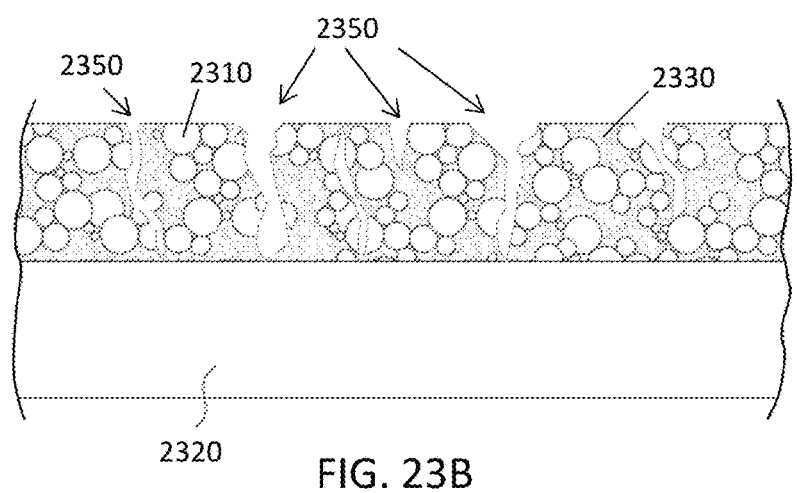
FIG. 23B

BONE IMPLANT AND SYSTEMS AND COATINGS FOR THE CONTROLLABLE RELEASE OF ANTIMICROBIAL METAL IONS

CROSS REFERENCE TO RELATED APPLICATIONS

This patent application is a continuation of U.S. patent application Ser. No. 16/391,195, filed Apr. 22, 2019, titled "BONE IMPLANT AND SYSTEMS AND COATINGS FOR THE CONTROLLABLE RELEASE OF ANTIMICROBIAL METAL IONS," now U.S. Pat. No. 11,020,508, which is a continuation of U.S. patent application Ser. No. 15/820,393, filed Nov. 21, 2017, titled "BONE IMPLANT AND SYSTEMS AND COATINGS FOR THE CONTROLLABLE RELEASE OF ANTIMICROBIAL METAL IONS," now U.S. Pat. No. 10,265,435, which is a continuation-in-part to U.S. patent application Ser. No. 14/833,569, filed on Aug. 24, 2015, and titled "COATINGS FOR THE CONTROLLABLE RELEASE OF ANTIMICROBIAL METAL IONS," now U.S. Pat. No. 9,821,094, which is a continuation-in-part of U.S. patent application Ser. No. 14/679,893, filed on Apr. 6, 2015, titled "COATINGS FOR THE CONTROLLABLE RELEASE OF ANTIMICROBIAL METAL IONS," now U.S. Pat. No. 9,114,197, which is a continuation-in-part of U.S. patent application Ser. No. 14/569,545, filed on Dec. 12, 2014, titled "BIOABSORBABLE SUBSTRATES AND SYSTEMS THAT CONTROLLABLY RELEASE ANTIMICROBIAL METAL IONS," now U.S. Pat. No. 8,999,367, which is a continuation of U.S. patent application Ser. No. 14/302,352, filed on Jun. 11, 2014, titled "BIOABSORBABLE SUBSTRATES AND SYSTEMS THAT CONTROLLABLY RELEASE ANTIMICROBIAL METAL IONS," now U.S. Pat. No. 8,927,004. U.S. application Ser. No. 14/833,569 also claims priority to U.S. Provisional Patent Application No. 62/059,714, filed on Oct. 3, 2014 and titled "COATINGS FOR THE CONTROLLABLE RELEASE OF ANTIMICROBIAL METAL IONS." Each of these patents and patent applications is herein incorporated by reference in its entirety.

U.S. patent application Ser. No. 15/820,393 also claims priority as a continuation-in-part to U.S. patent application Ser. No. 14/801,732, filed on Jul. 16, 2015, titled "BONE IMPLANT AND SYSTEMS THAT CONTROLLABLY RELEASES SILVER," now U.S. Pat. No. 9,889,284, which is a continuation of U.S. patent application Ser. No. 13/748,546, filed on Jan. 23, 2013, titled "BONE IMPLANT AND SYSTEMS THAT CONTROLLABLY RELEASES SILVER," now U.S. Pat. No. 9,108,051, which is a divisional of U.S. patent application Ser. No. 13/231,219, filed on Sep. 13, 2011, titled "BONE IMPLANT AND SYSTEMS THAT CONTROLLABLY RELEASES SILVER," now U.S. Pat. No. 8,771,323, which claims priority to the following U.S. Provisional Patent Applications: U.S. Provisional Patent Application No. 61/413,230, filed on Nov. 12, 2010, and titled "SILVER ELUTING BONE IMPLANTS AND METHODS OF USE;" U.S. Provisional Patent Application No. 61/438,162, filed on Jan. 31, 2011, and titled "BONE SUPPORTING IMPLANTS WITH ANTIBACTERIAL PROPERTIES;" U.S. Provisional Patent Application No. 61/447,393, filed on Feb. 28, 2011, and titled "INTRAMEDULLARY (INTRAOSSEAL) ROD, NAIL OR CATHETER WITH GALVANICALLY PRODUCED ANTIBACTERIAL PROPERTIES;" U.S. Provisional Patent Application No. 61/465,350, filed on Mar. 18, 2011, and titled "ANTIMICROBIAL IMPLANT TO PROVIDE MECHANICAL SUPPORT FOR A BORE THAT UTILIZES A GALVANIC POTENTIAL BETWEEN TWO OR MORE METALS TO CREATE IONS THAT ARE GERMICIDAL AND/OR ANTIFUNGAL;" U.S. Provisional Patent Application No. 61/516,388, filed on Apr. 4, 2011, and titled "GALVANIC ANTIMICROBIAL BONE SCREW FOR THE TREATMENT OF DISEASED, FRACTURE OR MISALIGNED BONE AND TO PROMOTE BONE GROWTH AND REGENERATION," each of which is incorporated by reference in its entirety.

U.S. patent application Ser. No. 14/801,732 is also a continuation-in-part of U.S. patent application Ser. No. 13/527,389, filed on Jun. 19, 2012, titled "BONE IMPLANTS FOR THE TREATMENT OF INFECTION," now U.S. Pat. No. 9,248,254, which is a continuation of U.S. patent application Ser. No. 12/870,082, filed Aug. 27, 2010, titled "BONE IMPLANTS FOR THE TREATMENT OF INFECTION," now U.S. Pat. No. 8,221,396, which claims priority to the following U.S. Provisional Patent applications: U.S. Provisional Patent Application No. 61/237,506, filed on Aug. 27, 2009, titled "SILVER ELLUTING BONE IMPLANTS AND METHODS OF USE;" U.S. Provisional Patent Application No. 61/340,587, filed on Mar. 19, 2010, titled "ANTIMICROBIAL ION ELUTING IMPLANTABLE DEVICE;" and U.S. Provisional Patent Application No. 61/359,549, filed on Jun. 29, 2010, titled "SILVER ELUTING BONE IMPLANTS AND METHODS OF USE," each of which is incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are substrates having antimicrobial metal ion coatings. In particular, described herein are substrates that are coated with an anodic metal (e.g., silver and/or zinc and/or copper) that is co-deposited with a cathodic metal (e.g., palladium, platinum, gold, molybdenum, titanium, iridium, osmium, niobium, rhodium, manganese, or rhenium) on the substrate to form a continuous path of interconnected veins of anodic metal within the matrix of cathodic metal or a continuous path of interconnected veins of cathodic metal within the matrix of anodic metal, wherein the continuous path extends from an outer surface of the coating to the substrate. Thus, the antimicrobial anodic metal (e.g., silver, zinc, copper) may be galvanically released as antimicrobial ions when the coated substrates is contacted by a conductive fluid environment, including when inserted into a subject's body.

BACKGROUND

Antimicrobial or antibiotic agents are widely used to treat as well as to prevent infection. In particular, silver is known to be antimicrobial and has been used (primarily as a coating) in various medical devices with limited success. Both active (e.g., by application of electrical current) and passive (e.g., galvanic) release of silver ions have been proposed for use in the treatment and prevention of infection. However, the use of silver-releasing implants have been limited because of the difficulty in controlling and distributing the release of silver ions as well as the difficulty in maintaining a therapeutically relevant concentration of silver ions in an appropriate body region. Zinc shares many of the same antimicrobial properties of silver, but has been less commonly used, and thus even less is known about how to control the amount and distribution of the release of silver ions to treat and/or prevent infection.

It would be highly beneficial to use an antimicrobial agent such as silver and/or zinc as part of an implant, including a bioabsorbable implant, in part because the risk of acquiring infections from bioabsorbable materials in medical devices is very high. Many medical applications exist for bioabsorbable materials including: wound closure (e.g., sutures, staples, adhesives), tissue repair (e.g., meshes, such as for hernia repair), prosthetic devices (e.g., internal bone fixation devices, etc.), tissue engineering (e.g., engineered blood vessels, skin, bone, cartilage, liver, etc.) and controlled drug delivery systems (such as microcapsules and ion-exchange resins). The use of bioabsorbable materials in medical applications such as these may reduce tissue or cellular irritation and the induction of an inflammatory response.

Bioabsorbable materials for medical applications are well known. For example, synthetic bioabsorbable polymers may include polyesters/polylactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers, as well as naturally derived polymers such as albumin, fibrin, collagen, elastin, chitosan, alginates, hyaluronic acid; and biosynthetic polyesters (e.g., 3-hydroxybutyrate polymers). However, like other biomaterials, bioabsorbable materials are also subjected to bacterial contamination and can be a source of infections which are difficult to control. Those infections quite often require their removal and costly antimicrobial treatments.

Efforts to render bioabsorbable materials more infection resistant generally have focused on impregnating the materials with antibiotics or salts such as silver salts, and have provided only limited and instantaneous antimicrobial activity. It is desirable to have an antimicrobial effect which is sustained over time, such that the antimicrobial effect can be prolonged for the time that the bioabsorbable material is in place. This can range from hours or days, to weeks or even years.

Further, although antimicrobial/antibacterial metal coatings on medical devices have been suggested, metal coatings (such as silver or copper coatings) have not been characterized or optimized. In such applications, it is important that the metal coatings do not shed or leave behind large metal particulates in the body, which may induce unwanted immune responses and/or toxic effects. Further, it is essential that the release of the antimicrobial agent (metal) be metered over the lifetime of the implant.

For example, U.S. Pat. No. 8,309,216 describes substrates including degradable polymers that include an electron donor layer (such as silver, copper or zinc) onto which particles of palladium and platinum, plus one other secondary metal (chosen from gold, ruthenium, rhodium, osmium, iridium, manganese or platinum) are deposited onto. Although such materials are described for anti-microbial implants (e.g., pacemakers, etc.), the separate layers formed by this method would be problematic for antimicrobial coatings in which the undercoating of silver, copper or zinc were being released, potentially undermining the platinum and secondary metal.

Similarly, U.S. Pat. No. 6,719,987 describes bioabsorbable materials having an antimicrobial metal (e.g., silver) coating that can be used for an implant. The silver coating is for release of particles (including ions) and must be in a crystalline form characterized by sufficient atomic disorder. In this example, the silver is also deposited in one or more layers. U.S. Pat. No. 6,080,490 also describes medical devices with antimicrobial surfaces that are formed by layers of metals (e.g., silver and platinum) to release ions; layers are etched to expose regions for release. The outer layer is always Palladium (and one other metal), beneath which is the silver.

Thus, it would be highly desirable to provide devices, systems and methods for the controlled release (particularly the controlled galvanic release) of a high level of silver, zinc or silver and zinc ions from a bioabsorbable material into the tissue for a sufficient period of time to treat or prevent infection.

Known systems and devices, including those described above, that have attempted to use ions (e.g., silver and/or zinc) on bioabsorbable materials to treat infection have suffered from problems such as: insufficient amounts of ions released (e.g., ion concentration was too low to be effective); insufficient time for treatment (e.g., the levels of ions in the body or body region were not sustained for a long enough period of time); and insufficient region or volume of tissue in which the ion concentration was elevated (e.g., the therapeutic region was too small or limited, such as just on the surface of a device). Further, the use of galvanic release has generally been avoided or limited because it may effectively corrode the metals involved, and such corrosion is generally considered an undesirable process, particularly in a medical device.

For example, Osteomyelitis is an infection of a bone by a microorganism such as bacteria or fungi. Diabetes, joint replacement, trauma, and injected drug use can lead to osteomyelitis. As people live longer, incidences of osteomyelitis are expected to increase. To complicate matters, an infection, such as following joint replacement surgery, can occur long after the incision has been closed. An infection buried in a bone can be difficult to detect; it is not visible to the eye and taking a culture sample is difficult and painful. Once diagnosed, antibiotics can eliminate many infections. Unfortunately, microorganisms are developing resistances rendering existing antibiotics useless. Reports of patients infected with microorganisms resistant to regular and "last resort" antibiotics are increasing in number. For these patients, there are few or no effective options. The problem is expected to become worse as microorganisms exchange genetic material and more species become resistant to antibiotics. Prophylactic use of antibiotics, although commonly done, is discouraged because it may increase antibiotic resistance. Infection with methicillin resistant *Staphylococcus aureus* (MRSA) is a significant health problem that is expected to worsen. Additionally, microorganisms on the surface of an artificial joint or other implanted device can cooperate to create an impervious layer, called a biofilm. A biofilm may form a mechanical barrier to an antibiotic.

Silver is known to be antimicrobial and has been used (primarily as a coating) in various medical devices with limited success. Both active (e.g., by application of electrical current) and passive (e.g., galvanic) release of silver ions have been proposed for use in the treatment and prevention of infection. However, the use of silver-releasing implants have been limited because of the difficulty in controlling and distributing the release of silver ions as well as the difficulty in maintaining a therapeutically relevant concentration of silver ions in an appropriate body region. Zinc shares many of the same antimicrobial properties of silver, but have been less commonly used, and thus even less is known about how to control the amount and distribution of the release of silver ions to treat and/or prevent infection.

Thus, it would be highly desirable to provide device systems and methods for the controlled release (particularly the controlled galvanic release) of a high level of silver, zinc or silver and zinc ions into the tissue for a sufficient period of time to treat or prevent infection.

Specifically, known systems and devices that have attempted to use ions (e.g., silver and/or zinc) to treat infection have suffered from problems such as: insufficient amounts of ions released (e.g., ion concentration was too low to be effective); insufficient time for treatment (e.g., the levels of ions in the body or body region were not sustained for a long enough period of time); and insufficient region or volume of tissue in which the ion concentration was elevated (e.g., the therapeutic region was too small or limited, such as just on the surface of a device). Further, the use of galvanic release has generally been avoided or limited because it may effectively corrode the metals involved, and such corrosion is generally considered an undesirable process, particularly in a medical device.

In general, controlled release of silver and/or zinc ions would be beneficial. Control of the release of ions may allow the treatment of the patient to be regulated by turning the release on/off. In general, silver coated devices do not typically allow for the controlled release of ions. Silver coatings or impregnations do not typically allow controlled release, because they are always "on" (e.g., always releasing silver) to some degree. Zinc coatings on traditional implants may suffer from the same problem. Since release depends on the ionic concentration of body fluids, the actual release (and therefore concentration) of ions may be difficult to predict and control.

There is a need for antimicrobial coatings for substrates generally. Antimicrobial coatings may be useful for any surface that will be exposed to a conductive fluid, including blood, sweat, lymph, etc., whether implanted or not. For example, there is a particular need for antimicrobial coatings for bioabsorbable materials, which can create an effective and sustainable antimicrobial effect, which do not interfere with the bioabsorption of the bioabsorbable material, and which do not shed or leave behind large metal particulates in the body as the bioabsorbable material disappears.

Therapeutically, the level of silver and/or zinc ions released into a body is important, because it may determine how effective the antimicrobial ions are for treating or preventing infection. As described in greater detail below, the amount or ions released galvanically may depend on a number of factors which have not previously been well controlled. For example, galvanic release may be related to the ratio of the anode to the cathode (and thus, the driving force) as well as the level of oxygen available; given the galvanic reaction, the level of oxygen may be particularly important for at the cathode. Insufficient oxygen at the cathode may be rate-limiting for galvanic release.

For example, with respect to silver, it has been reported that a concentration of 1 mg/liter of silver ions can kill common bacteria in a solution. Silver ions may be generated a galvanic system with silver as the anode and platinum or other noble metal as the cathode. However one of the challenges in designing a galvanic system for creation of silver ion in the body that has not been adequately addressed is the appropriate ratios of the areas of the electrodes (e.g., anode to cathode areas) in order to create the germicidal level of free silver ions. One challenge in designing a galvanic system is addressing the parasitic loss of current due to formation of silver chloride via reaction:

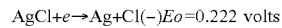

AgCl+$e$→Ag+Cl(−) $Eo$=0.222 volts

We herein propose that it may be beneficial to have an area of the cathode under common biological condition that is at least larger than 8% of the silver area to sustain the germicidal level of silver ions. For the purpose of this discussion, the following assumptions have been made: for a concentration of: [H+]=10^(−7) moles/liter; [OH—]=10^(−7) moles/liter; [O2]=5*10^(−3) moles/liter in the capillary; [Cl—]=0.1 moles/liter. The values of the following were also assumed (as constants or reasonable approximations): Faraday's constant, F=96000 coulombs/mole; diffusivity of oxygen=0.000234 cm2/sec; diffusivity of Ag+=10^(−6) cm2/sec; diffusivity of Cl—=10^(−6) cm2/sec; R, Gas constant=8.3141 K$^{-1}$ mol$^{-1}$; T, temp. K; Mw of silver=108 grams/mol; germicidal concentration of silver=10^(−5) mol/liter.

At equilibrium, for a galvanic cell it is acceptable to assume that the two electrodes are at the same potential. Using the Nernst equation, the equilibrium concentration of oxygen when the silver ion is at the germicidal level may be calculated:

$$E=Eo-(RT/nF)\ln[(\text{Activity of products})/(\text{activity of reactants})]$$

$$E=Eo-(0.0592/n)\text{Log }[(\text{product})/(\text{reactant})]$$

For the half cell reaction at the anode (silver electrode): Ag→Ag(+)+e(−). This reaction is written as a reduction reaction below:

Ag(+)+$e$(−)→Ag $Eo$=0.800 volt      eq. (1)

[Ag+]=1 mg/liter*(gr/1000 mg)*(1 mol/108 (Mw of Ag))=10^(−5) Ag+mole/liter; E=0.800−(0.0592/1) log [1/(10^(−5))]. Based on this, the resulting E=8.00−(0.0592*5)=0.504 volt.

For the cathode, the reactions are:

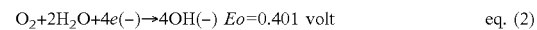

O$_2$+2H$_2$O+4$e$(−)→4OH(−) $Eo$=0.401 volt      eq. (2)

O$_2$+4H(+)+4$e$(−)→2H$_2$O $Eo$=1.229 volt      eq. (3)

In dilute aqueous solutions these two reactions are equivalent. At equilibrium the potential for the two half-cell potentials must be equal:

$$E=0.401-(0.0592/4)\log\{[OH(-)]^4/[O2]\}$$

$$E(\text{silver})=0.504=0.401-(0.0592/4)\log\{[10^{-7}]^4/[O2]\}$$

Solving for [O$_2$], the result is: [O$_2$]=10^(−21) atm. The result of this analysis is that, thermodynamically speaking, as long as the concentration of oxygen is above 10^(−21), the concentration of the sliver ion could remain at the presumed germicidal level.

However, a parasitic reaction to creation of silver ions is the formation of AgCl due to reaction of Cl— at the silver electrode. The half-cell potential for this reaction is:

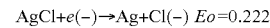

AgCl+$e$(−)→Ag+Cl(−) $Eo$=0.222

Solving the Nernst equation for this reaction with E=0.504, the concentration of chloride [Cl—]=2×10^(−5). The importance of this reaction becomes apparent in evaluating the current needed to compensate for the losses of current due to this reaction and the increased in ratio of the area of the cathode to the anode.

The current density per unit area requirements of the device can be estimated by combining Fick's and Faraday equations: the silver losses due to diffusion of silver from the device can be calculated using the Fick's equation:

$$j = D[C(d) - C(c)]/d \quad \text{Fick's equation}$$

The current needed to create the silver ions (A/cm2): $i = j \cdot n \cdot F$, where, j is the mass flux, C(d) is the concentration of the silver at the device and C(c) is concentration of silver at the capillary bed (=0). D is the diffusion coefficient of silver ($10^{-6}$) cm2/sec, d is the average distance of the device from the capillary bed (assumed to be=0.5 cm in the bone), F is Faraday's constant (96000 col./mol), and n is the charge number.

The combination of the two equations for silver diffusion gives:

$$i(Ag) = D \cdot n \cdot F(C(d))/d$$

Thus:

$$i(Ag) = \{10^{-6} \cdot 1 \cdot (10^{-5}) \cdot (96000) \cdot (5 \cdot 10^{-3}) / 0.5\} \cdot (1 \text{ liter}/1000 \text{ cc})$$

$$= 2 \cdot 10^{-9} \text{ Amp/cm}^2$$

The current needed to create the silver ions at the desired concentration is approximately 2 nanoAmp/cm2. Similarly, the current density (A/cm2) required to reduce the chloride ions from biological level (0.1 molar) to the desired level of $2 \cdot 10^{-5}$ molar could be calculated. For this equation the approximate values of the constants are $D = 10^{-6}$, $d = 0.1$ cm. The change in the Chloride concentration it assumed to be $(0.1 - 2 \cdot 10^{-5}) = 0.1$. The current needed to feed the parasitic reaction can then be determined:

$$i(cl) = \{(10^{-6}) \cdot (1) \cdot (96000) \cdot (0.1)/(0.1)\} \cdot (1 \text{ lit}/1000 \text{ cc})$$

$$= 9.6 \cdot 10^{-5}$$

$$= 96 \text{ microAmp/Cm}^2$$

The total anodic current needed is: $i(Ag) + i(Cl) = i$ (anodic) = 96 microAmps/cm². On the cathode, the reaction limitation is the flux of oxygen form the source to the surface of the electrode. The max i(cathodic) current could be approximated to:

$$i(O2) = \{(0.000324) \cdot (4) \cdot (96000) \cdot (5 \cdot 10^{-3})/(0.5)\} \cdot (1 \text{ lit}/1000 \text{ cc})$$

$$= 1.24 \cdot 10^{-3} \text{ Amps/cm}^2$$

Since the total cathodic current must be equal to total Anodic current:

$$i(\text{cathodic}) \cdot \text{Area of the cathode} = i(\text{anodic}) \cdot \text{Area of Anode}$$

$$\Rightarrow \text{Area of the Cathode/Area of the anode} = (96 \cdot 10^{-6})/(1.24 \cdot 10^{-3}) = 0.077$$

This suggests that the area of the cathode must be at least equal to 8% of that of anode.

In addition to the ratio of the cathode to the ratio of the anode, another factor affecting the release of silver ions that has not previously been accounted for in galvanic release of silver to treat infection is the concentration of oxygen needed.

The concentration of the oxygen needed to power the galvanic system is typically higher than that of the equilibrium concentration, since the system must overcome the activation energy of the reactions (over-potential) and supply the additional current. In the model below we evaluated the concentration of the oxygen needed to overcome the activation energy for the reactions. Using the Tafel equation:

$$\eta = \beta \log [i/io]$$

where i=current density, $\eta$=the over-potential, $\beta$=overpotential voltage constant, and io=intrinsic current density. For platinum, the oxygen over-potential constants are: $\beta = 0.05$ volt and io=$10^{-9}$ A/m². Using $i = 9.6 \cdot 10^{-5}$ Amp then:

$$\eta = 0.05 \log [9.6 \cdot 10^{-5}/(10^{-9})]$$

$$\eta = 0.25 \text{ volt}$$

Adding the over potential to the potential at the equilibrium (0.501 volts), and the total working half-potential needed at the cathode becomes equal to (0.501+0.25)=0.751.

Using the Nernst equation to determine the concentration of oxygen at the cathode:

$$E = 0.751 = 0.401 - (0.0592/4) \log \{[OH(-)]^4/[O2]\}$$

Thus, the concentration of oxygen at the electrode should be at least $7 \cdot 10^{-5}$ mole.

The results of this analysis show that an implanted galvanic system would benefit from having an area of the cathode to the area of the anode ($A_{cathode}/A_{anode}$) of greater that about 8% and the concentration of the oxygen at the site of implant to be at least $7 \cdot 10^{-5}$ moles per liter, which may avoid rate-limiting effect.

Thus, to address the problems and deficiencies in the prior art mentioned above, described herein are systems, methods and devices (and in particular coatings, methods of coatings) for substrates that controllably release antimicrobial metal ions, including apparatuses (e.g., devices and/or systems) and methods for prevent infection and for eliminating existing infections. The coatings described herein may be used as part of any appropriate substrate, including medical devices (both implanted, inserted, and non-implanted/inserted medical devices), and non-medical devices including hand-held articles. In some particular examples, described below are implants including bioabsorbable substrates, and methods for using them. Also described herein are systems, methods and devices for prophylactically treating a patient to prevent an infection and options for eliminating an existing infection, including those untreatable by any existing treatments. Described below are implants and methods for preventing and treating bone infections using an implantable, controllable, and rechargeable bone screws.

SUMMARY OF THE DISCLOSURE

In general, described herein are coatings and methods of forming and using coatings for any substrate that will come into contact with a bodily fluid and/or secretion, in which the coating may galvanically release antimicrobial ions. The coatings are configured so that the release of the antimicrobial ions (e.g., silver, zinc and/or copper) is sustained over a predetermined time period of continuous or intermittent exposure to the bodily fluid, and further so that the amount and/or concentration of the antimicrobial ions released is above a predetermined threshold for effective antimicrobial effect either locally or within a region exposed to the coating.

Although particular attention and examples of types of substrates, such as medical devices, and in particular implantable medical device including bioabsorbable substrates, it should be readily understood that the coatings described herein may be used on any substrate surface that will come into contact with bodily fluids which would benefit from an antimicrobial effect, including devices that are not inserted or implanted into a body. Bodily fluids are generally electrically conductive, and may include any of: blood, blood serum, amniotic fluid, aqueous humor, vitreous humor, bile, breast milk, cerebrospinal fluid, cerumen, chyle, chyme, endolymph, perilymph, exudates, feces (diarrhea), female ejaculate, gastric acid, gastric juice, lymph, mucus (including nasal drainage and phlegm), pericardial fluid, peritoneal fluid, pleural fluid, pus, rheum, saliva, sebum, semen, sputum, synovial fluid, sweat, tears, urine, vaginal secretion, vomit, etc.

As used herein, a substrate may be any surface onto which the coating may be applied, which may be any appropriate material, including, but not limited to metals (e.g., alloys, etc.), ceramics, stone, polymers, wood, glass, etc., including combinations of materials. In some variations the surface of the substrate may be prepared before the coating is applied, as described herein. The substrate may be rigid or flexible. In particular, the coatings described herein may be applied to flexible and/or fiber-like materials such as strings, sutures, woven materials, thin electrical leads, and the like. As described in greater detail herein, the coating typically does not inhibit the flexibility, pliability, bendability, etc. of the substrate material.

The coatings described herein typically include co-depositions of an anodic metal (e.g., one or more of zinc, silver, and/or copper) and a cathodic metal (e.g., one or more of: palladium, platinum, gold, molybdenum, titanium, iridium, osmium, niobium, rhodium, manganese, and rhenium). The anodic and cathodic material in the coating are non-uniformly dispersed within the coating, so that there are veins (e.g., microdomains or microregions, such as clusters, clumps, etc.) of anodic metal within a matrix of cathodic metal and/or veins of cathodic metal within a matrix of anodic metal. The relative amounts of anodic metal in the coating may be between 20% and 80% by volume, or more preferably between 25% and 75% by volume, or more preferably still, between 30% and 70% by volume (e.g., greater than 20%, greater than 25%, greater than 30%, etc.).

The anodic metal within the coating typically forms a continuous path through the coating (extending from the outer surface of the coating all the way to the base of the coating, which may be the portion against the substrate), so that all or most all (e.g., greater than 80%, greater than 85%, greater than 90%, greater than 95%, greater than 96%, greater than 97%, greater than 98%, greater than 99%, etc.) of the anodic metal in the coating is interconnected, preventing entrapment of a substantial portion of the anodic metal within the coating. Similarly, the cathodic metal within the coating may be in continuous contact throughout the coating layer (extending from the outer surface of the coating all the way to the base of the coating, which may be the portion against the substrate) so that all or most all (e.g., greater than 80%, greater than 85%, greater than 90%, greater than 95%, greater than 96%, greater than 97%, greater than 98%, greater than 99%, etc.) of the cathodic metal in the coating is interconnected.

As mentioned, the coatings described herein may be applied to any appropriate substrate. For example, an apparatus that galvanically releases antimicrobial ions may include: a substrate; and a coating on the substrate comprising an anodic metal (that has been co-deposited with a cathodic metal on the substrate) to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming a continuous path of interconnected veins of anodic metal within the matrix of cathodic metal or a continuous path of interconnected veins of cathodic metal within the matrix of anodic metal, wherein the continuous path extends from an outer surface of the coating to the substrate; further wherein the anodic metal is galvanically released as antimicrobial ions when the apparatus is inserted into a subject's body.

The substrate may be an implant configured to be inserted into a human body, including a medical device. The substrate may be device configured to be temporarily or permanently inserted into the body (e.g., surgical tools, implants, etc.). In some variations the substrate may be a device configured to be worn on a human body (e.g., jewelry, clothing, surgical gowns, masks, gloves, etc.). The substrate may be a structure configured to hold, support and/or house a subject (e.g., gurney, chair, bed, etc.). The coating may be applied to all or a portion of the substrate, particularly those surfaces of the substrate that may be placed in contact with a bodily fluid (e.g., a handle, supporting surface, etc.). The substrate may be a household item, such as a cutlery (e.g., spoons, baby spoons, forks, etc.), food handling items (e.g., platters, plates, straws, cups, etc.), handles (e.g., doorknobs, pushes, etc.), faucets, drains, tubs, toilets, toilet knobs, light switches, etc.

The anodic metal may be any combination of the anodic metals described herein (e.g., zinc, silver, copper, both zinc and silver, etc.). The anodic metal may be least about 30 percent by volume (or in some variations, by weight, e.g., when the densities of anodic and cathodic materials are similar) of the coating.

The cathodic metal may generally have a higher galvanic potential than the anodic metal. This may drive the galvanic (e.g., "corrosion") of the anodic metal when the coating is exposed to a bodily fluid. For example, the cathodic metal may comprise one or more of: palladium, platinum, gold, molybdenum, titanium, iridium, osmium, niobium, rhodium, manganese, and rhenium.

The coating may be formed by vapor deposition. For example, the anodic metal and the cathodic metal may have been vapor-deposited onto the substrate so that the anodic metal is not encapsulated by the cathodic metal, e.g., so that the anodic metal (and/or in some variations the cathodic metal) include veins that extend continuously through the coating from the outer surface to the base (e.g., the "bottom" of the coating adjacent to the substrate) of the coating. Thus, the continuous path of interconnected veins may be interconnected so that less than 15% of the anodic metal is completely encapsulated within the matrix of cathodic metal, or less than 15% of the cathodic metal is completely encapsulated within the matrix of anodic metal. The continuous path of interconnected veins may be interconnected so that less than 10% of the anodic metal is completely encapsulated within the matrix of cathodic metal, or less than 10% of the cathodic metal is completely encapsulated within the matrix of anodic metal.

An apparatus that galvanically releases antimicrobial ions may include: a substrate; and a coating on the substrate comprising zinc and silver and a cathodic metal that are all co-deposited onto the substrate, wherein the zinc and silver are at least about 25 percent by volume (or in some variations by weight) of the coating and form a non-uniform mixture of the zinc and the cathodic metal and a non-uniform mixture of the silver and the cathodic metal, wherein the coating comprises a plurality of microregions or microdomains of zinc and silver in a matrix of cathodic metal or a plurality of microregions or microdomains of cathodic metal in a matrix of zinc and a matrix of silver, the microregions or microdomains forming a continuous path of interconnected veins of zinc and silver within the matrix of cathodic metal or a continuous path of interconnected veins of cathodic metal within the matrix of zinc and the matrix of silver, wherein the continuous paths extend from an outer surface of the substrate; further wherein the zinc and silver are galvanically released as antimicrobial ions when the apparatus is inserted into a subject's body.

In some variations, the substrate may be bio-absorbable. For example, in some variations, the substrate is configured to degrade within the body to form a degradation product including an anion that complexes with ions of the anodic metal and diffuses into the subject's body to form an antimicrobial zone. For example, a bioabsorbable apparatus that galvanically releases antimicrobial ions may include: an implant having an outer surface comprising a substrate; and a coating on the substrate comprising an anodic metal that is co-deposited with a cathodic metal on the substrate to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming continuous paths of interconnected veins of anodic metal within the matrix of cathodic metal or continuous paths of interconnected veins of cathodic metal within the matrix of anodic metal, wherein the continuous paths extend from an outer surface of the coating to the substrate; further wherein the anodic metal is galvanically released as antimicrobial ions when the apparatus is inserted into a subject's body.

Thus, also described herein are bioabsorbable substrates, and particularly bioabsorbable filaments, that galvanically release antimicrobial ions. The bioabsorbable filament is coated with an anodic metal (such as silver, copper and/or zinc) that has been co-deposited with a cathodic metal (such as platinum, gold, palladium) along at least a portion of the length of the filament. The filament retains its flexibility. After insertion into the body, the anodic metal corrodes as the filament is bioabsorbed. The degradation of the filament may create a local pH that enhances the release of the silver and/or copper and/or zinc ions.

In general, the coated filaments may be arranged into structures (e.g., sutures, mesh, slings, yarns, etc.) that can be implanted into the body.

As mentioned, the anodic and cathodic metals forming the coatings described herein are typically co-deposited together, and not coated in layers (e.g., atop each other). For example, the metals may be jointly vapor deposited. Examples of jointly deposited anodic and cathodic materials include silver-platinum, copper-platinum, zinc-platinum, silver-gold, copper-gold, zinc-gold, etc. Different types of jointly deposited anodic and cathodic metals may be arranged on the bioabsorble substrate. For example, silver-platinum may be coated near (either not touching or touching) a region of zinc-platinum; different co-deposited anodic/cathodic metals may be a spacer region on the substrate.

In some variations, described herein are devices and methods for preventing an infection in an implantable device such as a pacemaker or a defibrillator when inserting it into a body by incorporating bioabsorbable materials that galvanically release antimicrobial/antibacterial metals such as silver and/or zinc and/or copper. For example, an implant may be inserted into a woven mesh made of a bioabsorbable material that is coated (or impregnated) with an anti-microbial anodic metal ions such as silver or zinc co-deposited with a catalytic cathodic metal such as platinum, gold, or palladium.

In general, as mentioned above, the anodic metal may be silver, zinc, or any other metal with germicidal activity, and the cathode metal may be platinum, gold, palladium, or any other metal with catalytic action, including molybdenum, titanium, iridium, osmium, rhodium, manganese, niobium and rhenium. The biodegradable substrate may be a biodegradable filament, such as polylactic acid (PLA), poly (lactic-co-glycolic acid) (PLGA), polyglycolide (PGA), polyglycoside-co-trimethylene carbonate (PGTMC), poly (caprolactone-co-glycoside), poly(dioxanone) (PDS), and poly(caprolactone) (PCL). As used herein the terms biodegradable and bioabsorbable may be used interchangeably.

For example, described herein are biodegradable filaments that may be formed into an envelope, pouch, pocket, etc. (generically, a co-implantable structure) made of a biodegradable polymer (such as PLGA, PGA, PLA, polycaprolactone, etc.). The implant may be co-implanted with the co-implantable structure, for example, by placing the mesh onto the implant before, during or after insertion into the body. The co-deposited metal coating of the co-implantable structure creates a galvanic system resulting in release of germicidal ions protecting the device from getting infected in the body once the device is implanted with the structure into a body. In the semi-aqueous environment of the body, the metal will corrode over time by releasing the ions (e.g., silver ions, copper ions, zinc ions, etc.). A coated bioabsorbable polymer could also or alternatively be used as an insert inside the lumen of the device such as a cannula, cannulated screw, or as a coating on a device. In another configuration the metal ions could be coupled with a polyanionic (negatively charged) polymer and mixed with the polymer.

For example, described herein are bioabsorbable apparatuses that galvanically release antimicrobial ions. The apparatus may comprise: a flexible length of bioabsorbable filament; and a coating on the length of filament comprising an anodic metal that is co-deposited with a cathodic metal on the length of filament; wherein the coated filament is flexible; further wherein the anodic metal is galvanically released as antimicrobial ions when the apparatus is inserted into a subject's body.

In general, in apparatuses (systems and devices) in which the anodic metal and the cathodic metal are co-deposited (e.g., by vapor deposition) the anodic metal may be at least about 25 percent (e.g., at least about 30 percent, at least about 35 percent, etc.) by volume of the coating. This may prevent complete encapsulation of the anodic material (e.g., zinc, silver, etc.) by the cathodic material (e.g., palladium, platinum, gold, molybdenum, titanium, iridium, osmium, niobium, rhodium, manganese, and rhenium). As described in greater detail below, the coatings applied may be configured to result in microregions or microdomains of anodic material in a matrix of cathodic material. The microdomains may be interconnected or networked, or they may be isolated from each other. In general, however, the concentrations of anodic material and cathodic material may be chosen (e.g., greater than 25% by volume of the anodic material, between about 20% and about 80%, between about 25% and about 75%, between about 30% and about 70%, etc.) so that the majority of the anodic material in the coating thickness is connected to an outer surface of the coating, allowing eventual corrosion of most, if not all of the anodic metal as anti-bacterial metal ions, while providing sufficient cathodic material to provide adequate driving force for the corrosion of the anodic material. Thus, the coating may comprise the anodic metal and the cathodic metal that have been vapor-deposited onto the length of filament so that the anodic metal is not encapsulated by the cathodic metal.

As mentioned, the anodic metal may comprise zinc, copper or silver, or in some variations both zinc and silver. In general, the cathodic metal has a higher galvanic potential than the anode. For example, the cathodic metal may be one or more of: palladium, platinum, gold, molybdenum, titanium, iridium, osmium, rhodium, manganese, niobium and rhenium.

As mentioned, in general the bioabsorbable substrate (e.g., filament) may comprise one or more of: polylactic acid (PLA), poly(lactic-co-glycolic acid) (PLGA), polyglycolide (PGA), polyglycoside-co-trimethylene carbonate (PGTMC), poly(caprolactone-co-glycoside), poly(dioxanone) (PDS), and poly(caprolactone) (PCL).

In general, the bioabsorbable substrate (including a length of bioabsorbable filament) is configured to degrade within the body to form a degradation product, including an anion that complexes with ions of the anodic metal and diffuses into the subject's body to form an antimicrobial zone.

The bioabsorbable substrate (e.g., bioabsorbable filament) may be configured as a mesh, bag, envelope, pouch, net, or the like, that may be configured to hold an implant. For example, the flexible structure may be configured to at least partially house a pacemaker, defibrillator, neurostimulator, or ophthalmic implant.

Also described herein are bioabsorbable apparatuses that galvanically release antimicrobial ions and comprise: a plurality of lengths of bioabsorbable filament arranged in a woven structure; and a coating on the lengths of filament comprising zinc and silver and a cathodic metal that are all co-deposited onto the lengths of filament, wherein the zinc and silver are at least about 25 percent by volume of the coating; further wherein the zinc and silver are galvanically released as antimicrobial ions when the apparatus is inserted into a subject's body. As mentioned, the woven structure may form a mesh, bag, envelope, pouch, net, or other structure that is configured to at least partially enclose an implant within the subject's body.

Also described herein are bioabsorbable apparatuses that galvanically releases antimicrobial ions and include: a plurality of lengths of bioabsorbable filament; and a coating on the lengths of filament comprising an anodic metal that is co-deposited with a cathodic metal on the lengths of filament; wherein the lengths of filament are arranged into a flexible structure; further wherein the anodic metal is galvanically released as antimicrobial ions when the apparatus is inserted into a subject's body.

Methods of forming any of these apparatuses are also described, including methods of forming a coated bioabsorbable substrate, for example, by co-depositing (vapor depositing) an anodic material and a cathodic material onto the substrate. The substrate may be a fiber or the structure formed of the fiber. In some variations the method may also include forming different regions of co-deposited anodic and cathodic materials, wherein the different regions include different combinations of anodic and cathodic materials. The different regions may be non-contacting. In general, co-deposing anodic and cathodic materials are typically performed so that the anodic material forms greater than 25% by volume of the coating, preventing encapsulation of the anodic material by cathodic material within the coating.

Also described are methods of treating a subject using the bioabsorbable materials that are co-deposited with one or more coating of anodic and cathodic metals (e.g., materials). For example, described herein are methods of galvanically releasing antimicrobial ions to form an antimicrobial zone around an implant that is inserted into a subject's tissue. The method may include step of: inserting into the subject's tissue an apparatus comprising a plurality of lengths of bioabsorbable filament having a coating comprising an anodic metal and a cathodic metal that are co-deposited onto the lengths of filament, wherein the implant is at least partially housed within the apparatus; galvanically releasing antimicrobial ions from the coating (e.g., galvanically releasing ions of silver and zinc); allowing the lengths of filament to degrade into a degradation product including anions, wherein the anions complex with antimicrobial ions of the anodic metal and diffuse into the tissue to form an antimicrobial zone around the implant. The method may also include inserting an implant into the apparatus before the apparatus is inserted into the subject's body. For example, inserting the apparatus into the body may comprise inserting a flexible apparatus comprising the plurality of length of bioabsorbable filaments forming a bag, envelope, pouch, net or other structure (woven or otherwise) formed to hold the implant. For example, the method may also include inserting a pacemaker, a defibrillator or a neurostimulator into the apparatus.

Inserting the apparatus may comprise inserting the apparatus having a plurality of lengths of bioabsorbable filaments coated with the anodic metal that comprises silver and zinc that are co-deposited onto the lengths of filament with the cathodic metal.

Allowing the lengths of filament to degrade may comprise degrading the lengths of filament into anions that bind to silver ions from the coating. For example, inserting the apparatus comprises inserting the apparatus having a plurality of lengths of bioabsorbable filaments coated with the anodic metal that is co-deposited onto the lengths of filament with the cathodic metal, wherein the anodic metal is at least about 25 percent by volume of the coating (e.g., at least about 30%, at least about 35%, etc.).

Inserting the apparatus comprising the plurality of lengths of bioabsorbable filament may comprise inserting the apparatus having a plurality of lengths of one or more of: polylactic acid (PLA), poly(lactic-co-glycolic acid) (PLGA), and polyglycolide (PGA).

In general, the antimicrobial zone around the implant may be sustained for at least seven days.

Also described herein are apparatuses that galvanically releases antimicrobial ions and include: a substrate; and a coating on the substrate, the coating comprising a mixture of between about 25% and 75% by volume of an anodic metal and between about 25% to 75% by volume of a cathodic metal co-deposited on the substrate, wherein the coating comprises a plurality of microregions or microdomains of anodic metal in a matrix of cathodic metal or a plurality of microregions or microdomains of cathodic metal in a matrix of anodic metal, the microregions or microdomains forming interconnected veins of anodic metal through the coating thickness, or an interconnected veins of cathodic metal through the coating thickness, wherein the paths extend from an outer surface of the coating through the coating to an opposite side of the coating; wherein the anodic metal is galvanically released as antimicrobial ions when the apparatus is exposed to a bodily fluid.

In general, these coatings may be formed in a pattern on the substrate. For example, the coating may form one or more of: a sinusoidal pattern, cross-hatched pattern, a mesh pattern, a web pattern, or a zig-zag pattern.

As discussed above, any appropriate substrate may be used, including one or more of: a cloth, a surgical drape, a catheter, an outer housing of a surgical implant, a pacemaker, defibrillator, neurostimulator, or ophthalmic implant. The substrate may comprise a surface of one of: an implantable shunt, an artificial joint, a hip implant, a knee implant, a stent, an implantable coil, a pump, an intrauterine device (IUD), a heart valve, a surgical fastener, a surgical staple, a surgical pin, a surgical screw, an implantable electrical lead, or an implantable plate.

For example, described herein are apparatuses that galvanically releases antimicrobial ions, the apparatus comprising: a substrate; and a patterned coating on the substrate, the patterned coating comprising a mixture of between about 25% and 75% by volume of an anodic metal and between about 25% to 75% by volume of a cathodic metal co-deposited on the substrate, wherein the coating comprises a plurality of microregions or microdomains of anodic metal in a matrix of cathodic metal or a plurality of microregions or microdomains of cathodic metal in a matrix of anodic metal, the microregions or microdomains forming interconnected veins of anodic metal through the coating thickness, or an interconnected veins of cathodic metal through the coating thickness, wherein the paths extend from an outer surface of the coating through the coating to an opposite side of the coating, wherein the patterned coating includes one or more of: a sinusoidal pattern, cross-hatched pattern, a mesh pattern, a web pattern, or a zig-zag pattern, further wherein the anodic metal is galvanically released as antimicrobial ions when the apparatus is exposed to a bodily fluid.

Also described herein are methods of galvanically releasing antimicrobial ions from a coated surface, comprising: contacting the coated surface with a bodily fluid, wherein the coated surface comprises a coating having a mixture of between about 25% and 75% by volume of an anodic metal and between about 25% to 75% by volume of a cathodic metal co-deposited on the surface, further wherein the coating comprises a plurality of microregions or microdomains of anodic metal in a matrix of cathodic metal or a plurality of microregions or microdomains of cathodic metal in a matrix of anodic metal, the microregions or microdomains forming a path of interconnected veins of anodic metal through the coating thickness, or a path of interconnected veins of cathodic metal through the coating thickness, wherein the path extends from an outer surface of the coating through the coating to an opposite side of the coating; and galvanically releasing antimicrobial ions of the anodic metal from the coating.

Contacting the coated surface may include contacting a surface having a pattern of coating, wherein the pattern is one or more of a sinusoidal pattern, cross-hatched pattern, a mesh pattern, a web pattern, or a zig-zag pattern. In this way, the entire surface does not need to be coated, though the antimicrobial ions may be release in a larger region to a larger field of antimicrobial protection, particularly when apparatuses including the coatings are inserted or implanted into a body.

For example contacting the coated surface may include contacting a surface of a one or more of: a cloth, a surgical drape, as surgical instrument cover, a surgical instrument, a catheter, an outer housing of a surgical implant, a pacemaker, defibrillator, neurostimulator, or ophthalmic implant, an implantable shunt, an artificial joint, a hip implant, a knee implant, a stent, an implantable coil, a pump, an intrauterine device (IUD), a heart valve, a surgical fastener, a surgical staple, a surgical pin, a surgical screw, an implantable electrical lead, an implantable plate, a handle, a cage, or an item of cutlery.

Contacting the coated surface with the bodily fluid may include implanting an apparatus including the coated surface into a patient's body. In some variations, contacting the coated surface with the bodily fluid comprises touching the coated surface with a bare skin surface.

In addition to the cathode metals for any of the apparatuses (devices, systems, etc.) described herein my include manganese as the cathode metal or as one of the cathode metals. In particular, any of the cathode metals (e.g., for the coatings) may include a combination of platinum and manganese, or palladium and manganese, or a combination of all three. For example, the coating may be applied by sputter platinum, palladium and manganese, and these metals could be co-sputtered at the same time with the anode metal (e.g., Ag).

Also described herein are systems, devices and methods that may generally be used to treat or prevent infection, including bone infections such as osteomyelitis by the controlled release of silver, zinc, or silver and zinc ions. In particular, the systems, methods and devices described herein may be configured to allow controllable galvanic release of ions (e.g., silver, zinc or silver and zinc ions) to treat or prevent infection. Many of the variations described herein may be used in conjunction with one or more implants that also structurally or therapeutically support the patient, including particularly the patient's bones.

In general, any of the implants described herein may be used to treat bone and/or soft tissue. In some variations the implants are bone implants specifically, and may be configured to support as well as treat the bone. For example, the implant may be used to secure (as a screw, nail, bolt, clamp, etc.) another member such as a plate, rod, or the like, or the implant may itself include a support member such as a rod, plate, etc. In some variations, the implant is a soft tissue implant that is configured to be secured within non-bone body structures.

Although many of the examples described herein are illustrated describing the release of silver ions, any of the devices, methods and systems described may be configured for the release of zinc ions instead of, or in addition to, silver ions. It may be beneficial to release both zinc and silver ions. In some situations it may be beneficial to release zinc rather than silver, or vice versa. For example, variations of the devices releasing zinc may be used preferentially when the infection targeted is resistant to silver. Zinc may also "corrode" faster, e.g., releasing ions more quickly and/or at a higher concentration than silver, which may be avoided or exploited depending upon the context.

Described herein are systems, devices and methods for the controlled release of silver, zinc, or silver and zinc ions to treat or prevent infection that may address many of the problems identified above. For example, described herein are devices configured for the galvanic release of ions that may be controlled with an on/off switch mechanism. For example, in some variations the galvanic relationship can be regulated remotely (before or after the silver and/or zinc releasing implant has been inserted into the body). In some variations the systems and device may be configured so that the implant includes a separable or separate cathode and/or anode. The anode region (e.g., silver, zinc, or silver and zinc anode) may be placed central to the treatment region while the cathode could be positioned in an oxygen-rich region that may be separate from the treatment region (e.g., oxygenated blood). This may allow effective treatment of even relatively anoxic regions, including bone.

The devices and systems described herein may also be configured to regulate the effective cathode active surface area and anode active surface area (e.g., making the cathode surface area much larger than the effective anode surface area). For example, the cathode active surface area may be 5% greater (e.g., Au/Palladium), 8% (e.g., Au/Pt), 10% (e.g., Au/Ag), etc. than the anode surface area.

For example described herein are implants, including bone implants, for providing antimicrobial treatment to a region of a bone (and/or surrounding tissues) In some variations the implant includes: an elongate cannulated body having a threaded outer region; at least one exit channel extending from the cannulated body and out through the threaded outer region; and one or more silver, zinc, or silver and zinc release members configured to extend from the cannulated body and out of the exit channel.

The ion release members may be configured as part of a removable treatment cartridge that is configured to fit within the cannulated body of the implant so that the one or more ion release members extend from the cannulated body. Note, as used herein the phrase "treat" and "treatment" may include acute and prophylactic treatments.

In the simplest variation, the implant is configured as a bone screw that is hollow or contains a hollow inner body region into which a replaceable/rechargeable treatment cartridge may be inserted and/or removed. The cartridge may be itself screwed into the body, or it may be otherwise secured within the body. The cartridge may include one or more (e.g., a plurality) of ion release members extending or extendable from the cartridge and therefore the implant. An ion release member may be configured to release silver, zinc or silver and zinc. In general an ion release member may be configured as an elongate member such as an arm, wire, branch, or the like. The ion release member may be a wire (e.g., silver wire), or it may be a coated member such as a Nitinol or other shape-memory member, including a silver and/or zinc coating. As mentioned, the implant (or the treatment cartridge portion) may include a plurality of ion release members.

An implant may have one or more exit channels. In general the exit channels may be openings from the inner hollow region (e.g. cannulated body) of the implant through a side wall of the implant and out, possibly in the threaded region. Thus, in some variations the exit channel is configured to deflect the one or more ion release members away from a long axis of the implant. For example, the exit channel may be configured to deflect the one or more ion release members against a thread of the outer threaded region so that it deflects away from the implant. In some variations a plurality of exit channels extending through the cannulated body.

An implant may also include a guide (or guide element, including a rail, keying, etc.) within the channel configured to guide or direct the one or more ion release member out of the cannulated body from the at least one exit channel. The exit channels may be configured to allow tissue (e.g., bone) ingrowth, which may help with stability of the device once implanted. For example, the exit channels may be slightly oversized compared to the ion release members, permitting or encouraging in-growth. In some variations the exit channels may be doped or otherwise include a tissue-growth enhancing or encouraging factor (such as a growth factor), or may be otherwise modified to encourage tissue growth.

In some variations the treatment cartridge may include a silver, zinc or silver and zinc anode and the elongate body includes a cathode, wherein the cathode has a higher redox potential than the anode. The cathode may have an irregular surface, or a high-surface area (e.g., per unit volume); for example, the cathode may be formed of a foamed metal. In general the surface area of the cathode may be substantially greater than the surface are of the anode.

The treatment cartridge may be replaceable. For example, a treatment cartridge may be configured to be removable from the cannulated body of the implant in situ, without removing the body of the implant from the device. Thus, the body of the implant may be structurally supportive (e.g., supporting the bone) while the silver-releasing portion may be re-charged by inserting another (replacement) cartridge after the previous cartridge has corroded. For example, an elongate cannulated body may be configured as bone screw (e.g., an intramedullary bone screw).

In some variations, an implant for providing antimicrobial treatment to a tissue includes: an elongate body having a threaded outer screw region; an inner channel within the elongate body; a plurality of exit channels extending from the inner channel and out through the threaded outer screw region; and a treatment cartridge configured to fit within the inner channel, the cartridge comprising a plurality of ion release members configured to extend out of the exit channels.

As mentioned, the inner channel may include a guide element configured to direct the release members out of the exit channels. The guide element may be a shaped channel region (e.g., keying) or the like, configured to regulate the interaction between the implant body and the cartridge.

Any of the variations described herein may also include a tissue sampling feature. For example, the treatment cartridge may comprise a sampler element configured to obtain a sample from a patient in whom a bone implant has been implanted. A sampler element may be a region configured to scrape, cut or otherwise remove a sample of tissue, particularly as the cartridge is removed from the implant. The sampled tissue may be examined for infection or the like.

Also described herein are systems for the controllable galvanic release of silver, zinc or silver and zinc ions from an implant to prevent or treat infection. For example, a system may include: a threaded implant configured to be inserted into a bone and to hold an ion releasing treatment cartridge; a cathode on the implant, the cathode comprising a material having a higher redox potential than the material of the anode (e.g., silver, zinc or silver and zinc); a treatment cartridge comprising a silver, zinc or silver and zinc anode, wherein, when the treatment cartridge is held by the implant, the cathode is in electrical contact with the anode, driving the galvanic release of ions from the release cartridge; and a switchable control configured to regulate electrical contact between the anode and cathode.

In any of the variations described herein, the cathode may comprise a material selected from the group consisting of: palladium, platinum, and gold. The cathode and anode may be configured to generate a galvanic current greater than about 0.2 µamps. The treatment cartridge may include a plurality of ion release members configured to extend from the implant when the cartridge is engaged therewith.

As mentioned above, any of the variations described herein may include a switchable control configured to turn on and/or off the galvanic activity between the anode and cathode. In some variations the switch may be configured to electrically separate the anode and cathode preventing or limiting the galvanic reaction. In some variations, the switchable control may be configured for remote activation. For example, a switchable control may include a magnet.

Also described herein are methods of controllably delivering silver ions from an implant to prevent or treat infection. Such a method may include the steps of: engaging an implant with a removable ion-releasing treatment cartridge, wherein the treatment cartridge comprises an anode (silver, zinc or silver and zinc), and wherein the implant includes a cathode comprising a material having a higher galvanic potential than the anode, further wherein the cathode has a greater active surface area than the active surface area of the anode; and activating a switchable control to initiate the galvanic release of ions from the treatment cartridge by placing the cathode in electrical contact with the anode.

The step of engaging the implant with the removably treatment cartridge may include coupling the treatment cartridge with an implant already inserted into a patient. The method may also include the step of placing at least a portion of the cathode in communication with a source of oxygen at a concentration of greater than $7 \times 10^{-5}$ mol/L. In some variations, the implant may be implanted into a bone.

Also described are systems for the release of ions from an implant to prevent or treat infection, the system including: an implant configured to hold a silver, zinc or silver and zinc release treatment cartridge; a removable treatment cartridge comprising a silver, zinc or silver and zinc anode; and a cathode comprising a material having a higher redox potential than the anode, wherein the cathode is configured to be positioned separately from the anode and in contact with an oxygen-rich environment when the implant is implanted; wherein, when the treatment cartridge is held by the implant, the cathode is in electrical contact with the anode, driving the galvanic release of ions from the treatment cartridge.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 8A is a side perspective view of one example of a plug or patch that may be used, e.g., to repair a hernia. The device is coated with multiple types of combined coatings for galvanic release of metal ions.

FIG. 8B shows an enlarged view of one region of the plug.

FIG. 9 is a perspective view of one variation of a bandage or patch including a combined coating, shown on a patient's knee.

FIG. 15A is an example of a triple lumen device and FIG. 15B is an example of a dual lumen device.

FIG. 19A is another example of bone screw implant having openings or channels from which members (shown extending in FIG. 19B) may extend. Either or both the bone screw and the extending members may be coated as described herein.

FIG. 20 shows an example of an animal cage coated as described herein.

FIG. 21 shows an example of a doorknob coated as described herein.

FIG. 22A shows an example of cutlery (a fork and spoon) coated as described herein.

FIG. 22B shows another example of spoon coated as described herein.

FIG. 23A show a cross-sectional view through an example of a substrate surface having a coating comprising an anodic metal co-deposited with a cathodic metal, in which the coating has been cracked, enhancing available surface area, as described herein.

FIG. 23B is a schematic representation of an enlarged view of a portion of the coated substrate of FIG. 23A, schematically showing (not to scale) micro-domains or veins of anodic metal within a cathodic matrix, showing cracks in the coating.

FIG. 24A shows an example of a cross-hatched pattern that may be formed on a substrate, including a tube or catheter, by masking. FIG. 24B illustrates an example of a diagonal hatched pattern of coating as described herein that may be coated on a substrate, including a catheter or tubing.

FIG. 24C illustrates another example of a sinusoidal pattern of coating.

In FIG. 25A the draping shown may be coated with the antimicrobial coating described herein, and the draping applied over an endoscope. FIG. 25B shows another endoscope, attached to a monitor, including a surgical drape.

DETAILED DESCRIPTION

Figure 1A:
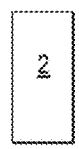
FIGS. 1A-1F illustrate the general concept of galvanic release of silver ions.
Figure 1B:
Figure 1C:
Figure 1D:
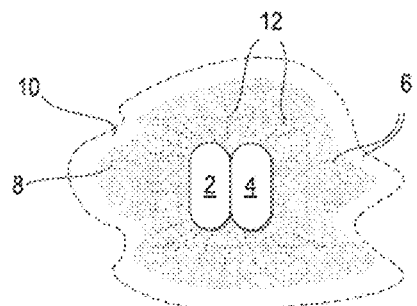

In general, described herein are apparatuses (e.g., systems and devices) that include a coating or layer that galvanically releases antimicrobial ions over an extended period of time. The coating may be applied to a substrate, e.g., a bioabsorbable and/or biodegradable substrate that may degrade during the same period that the antimicrobial ions are being released, e.g., days, months, years. In some variations the substrate may be coated with an adhesion layer on the substrate. The substrate may be pre-treated (e.g., to remove oxides, such as the titanium oxide layer on a nickel titanium substrate). In general, the coating may include a combination of anodic metal, such as silver and/or zinc and/or copper, and a cathodic metal, such as palladium, platinum, gold, molybdenum, titanium, iridium, osmium, niobium, rhodium, manganese and rhenium, where the anodic metal and cathodic metals are co-deposited (e.g., by vapor deposition) so that the anodic metal is exposed to an outer surface of the coating and not fully encapsulated in the cathodic metal, and there is sufficient cathodic metal to drive the galvanic release of anodic ions when exposed to bodily fluids such as blood, lymph, etc. (e.g., when implanted into the body).

For example, described herein are apparatuses including substrates onto which anodic metal and cathodic metals are co-deposited to form a coating, allowing the anodic metal to be galvanically released as ions (e.g., antimicrobial silver, copper and/or zinc ions) when the apparatus is exposed to a conductive fluid (e.g., a bodily fluid). The substrate may include an adhesive coating (such as a tantalum or titanium layer that is applied before the galvanic coating of co-deposited antic and cathodic metal).

Galvanically Releasable Coating

In general, the antimicrobial metal ion coatings described herein are galvanically releasable within a tissue, and include one or more anodic metal (typically silver and/or zinc and/or copper) that is co-deposited with a cathodic metal (typically platinum and/or palladium). The anodic metal and the cathodic metal are co-deposited, e.g., by sputtering or other appropriate methods described herein, so that the resulting coating is non-homogenous, with a percentage of anodic metal (e.g., silver) that is greater than about 30% co-distributed (typically in clusters, veins or clumps as illustrated and described below) with the cathodic metal (e.g., platinum), where the cathodic metal is greater than about 30% (e.g. % w/w) of the coating. The antimicrobial metal ion coatings described herein may be generally referred to as non-homogenous mixtures where the anode is distributed in connected clusters (veins) within the cathodic metal (or vice-versa). Generally, both the anodic metal and the cathodic metal are exposed in microdomains across the outer surface of the coatings, allowing galvanic release; as the anodic metal is released, it may form channels (e.g., tunnels, mines, etc.) through the coating, e.g., within the cathodic material. In some variations the cathodic material remains behind. In some variations some of the cathodic material may also be released.

Thus, in any of these variations, the coating may comprise a non-uniform mixture of the anodic and cathodic metals, with a plurality of microregions or microdomains of anodic metal in a matrix of cathodic metal, and/or a plurality of microregions or microdomains of cathodic metal in a matrix of anodic metal. These microregions or microdomains may be formed by co-deposition as described herein.

Any of the coatings described herein may include co-deposited multiple anodic and/or multiple cathodic metals forming the coating. In some variations, it may be preferable to separate regions having a first anodic metal (e.g., silver) from regions having a second anodic metal (e.g., zinc), so that they are separated (e.g., in some variations electrically separated) and/or non-contacting, allowing preferential release of one metal ion (e.g., zinc) compared to silver. This may allow control of the release profile, and may extend the length of effective release time for as coating.

In general, these coatings may be any appropriate thickness. For example, the thickness could be a few microns thick or more (e.g., greater than 2 microns, greater than 5 microns, greater than 10 microns, greater than 15 microns), etc. For example, the thickness of the coating may be between about 10 microinches (approximately 2500 Angstroms or approximately 0.25 microns) and about 25 microinches (approximately 6350 Angstroms or about 0.64 microns). The thickness of the coating may be uniform or non-uniform. Only some regions of the substrate may be coated, while other regions may be masked to prevent coating. For example, in an electrical stimulation apparatus (e.g., cardiac stimulator, neurostimulator, etc.) the body and/or connectors of the device may be insulated while the electrical leads (electrical contacts) to deliver energy to the tissue may be uncoated. Alternatively in some variations the electrical contacts are coated as described herein.

Figure 1E:
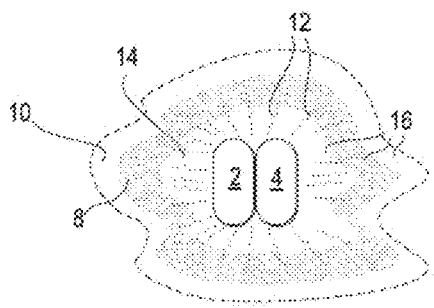
Figure 1F:
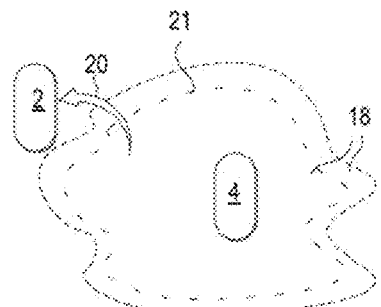

FIGS. 1A-1F conceptually describe a simple galvanic cell setup such as for use in a body. The setup is shown treating an infection, but the same process could be applied to healthy tissue to prevent an infection (prophylactically). The components including a first metal 2 (e.g., silver), second metal 4 (e.g., platinum), and electrolytic fluid 6 (e.g., blood) are shown individually in FIGS. 1A-1C and arranged in a tissue in FIGS. 1D-1F. Electrolytic body fluid 6 is shown bathing or contacting healthy tissue 10 as well as infected tissue 8. When silver metal 2 contacts platinum metal 4 in body fluid 6, it forms a galvanic cell with a silver anode and platinum cathode. As shown in FIG. 1E, ionic silver 12 is generated and spreads through the body fluid, killing microorganisms and creating an infection-free zone 14 in body fluid 16 in the vicinity of the anode. After treatment is complete, the silver anode 2 may be completely corroded 20 leaving an infection-free body fluid 18. Any metal with a higher redox potential than silver may be used as the cathode. The metal may be a noble metal, such as gold, palladium or platinum. Although the example shown in FIGS. 1A-1F describes using a silver metal anode that is placed adjacent to a platinum metal cathode, described herein are coatings in which the anodic metal (e.g., silver, zinc, copper) is co-deposited onto a biodegradable substrate.

In general, a coating of anodic metal and cathodic metal may be configured so that the anodic metal and cathodic metal are within the same coating layer. The microregions of anodic metal may be embedded within the cathodic metal, including being embedded within a matrix of cathodic metal (or vice versa). As illustrated below, the microdomains or microregions of anodic metal are within a cathodic matrix, allowing a large spatial release pattern of anodic metal ions by galvanic action triggered by the contact of the anodic metal and the cathodic metal within the electrolytic bodily fluid. The coatings described herein, in which the anodic metal and the cathodic metal are combined as part of the same layer may be referred to as "combined" coatings, in which an anionic metal and a cationic metal are both jointly coated, and/or non-homogenous (non-uniform) mixtures of anodic and cathodic metal.

The combined coatings described herein may be non-uniform mixtures of anodic and cathodic metals. For example, the anionic metal may form microregions or microdomains within the cationic metal (or vice versa). In general, the cathodic metal microdomains may form one or more (typically a plurality) of continuous paths through the cathodic metal. For example, the microdomains described herein may be veins, clusters, threads, clumps, particles, etc. (including interconnected veins, clusters, threads, clumps, particles, etc.) of anodic metal, e.g., silver, copper, and/or zinc, etc., that are connected to an outer surface of the coating, so that they are exposed to the electrolytic bodily fluid (e.g., blood). The microdomains of anodic metal may form a network within the matrix of the cathodic metal. Thus, the anodic metals may be present in one or more networks that are electrically connected within the cathodic matrix. The individual sizes of particles, threads, branches, veins, etc. forming the microdomains may be small (typically having a length and/or diameter, e.g., less than a 1 mm, less than 0.1 mm, less than 0.05, less than 0.01 mm, less than 0.001 mm, less than 0.0001 mm, less than 0.00001 mm, etc.). Similarly, in some variations the matrix may be the anodic metal and the cathodic metal may be referred to as forming microdomains (e.g., where the percentage of cathodic metal in the coating is less than 50%, less than 45%, less than 40%, less than 30%, etc. by volume of the coating).

A combined anodic metal and cathodic metal forming a combined coating (or a portion of a coating) may be formed of a single anodic metal (e.g., silver) with a single cathodic metal (e.g., platinum), which may be referred to by the combined anodic metal and cathodic metals forming the coating or portion of a coating (e.g., as a combined silver/platinum coating, a combined silver/palladium coating, a combined zinc/platinum coating, a combined zinc/palladium coating, etc.). In some variations a combined coating may include multiple anodic and/or cathodic metals. For example, the combined coating may include zinc and silver co-deposited with platinum.

As mentioned, the anodic metal in the combined coating may include a continuous path connecting the anodic metal to an exposed outer surface of the coating so that they can be galvanically released from the coating. Deeper regions (veins, clusters, etc.) of the anodic metal may be connected to more superficial regions so that as the more superficial regions are corroded away by the release of the anodic ions, the deeper regions are exposed, allowing further release. This may also expose additional cathodic metal. Thus, in general, anodic metal microdomains are not completely encapsulated within the catholic metal. In some variations, the majority of the anodic metal is not completely encapsulated within the cathodic metal, but is connected to an exposed site on the surface of the coating via connection through a more superficial region of anodic metal; although some of the anodic metal may be completely encapsulated.

For example, the coating may include an anodic metal in which less than 50 percent of the total anodic metal is completely encapsulated within the cathodic metal (e.g., less than 40%, less than 35%, less than 30%, less than 25%, less than 20%, less than 15%, less than 10%, etc.).

The co-deposited anodic and cathodic combined coatings described herein for the galvanic release of anodic ions may be formed by co-depositing the anodic metal and the cathodic metal so as to minimize the amount of encapsulation by the cathodic material. For example, the percentage of the anodic material may be chosen so that there is both an optimal amount of cathodic metal to drive reasonable galvanic release in the presence of an electrolyte, and so that there is sufficient continuity of anodic metal with the combined coating to form a continuous path to an exposed surface of the coating, making it available for galvanic release. For example, a coating may be formed by co-depositing the anodic metal and the cathodic metal (e.g., sputtering, vapor deposition, electroplating, etc.) where the concentration of the anodic metal is high enough to allow the formation of a sufficient number of continuous paths through the thickness of the coating. We have found that a combined coating in which more than 25% by volume (or more preferably more than 30%) of the coating is formed of the anodic metal is sufficient to form a combined coating with a cathodic metal in which more than half (e.g., >50%) of the anodic metal is connected by a continuous path to the surface of the coating, permitting galvanic release. For example, a coating having between about 33-67% of anodic metal and between about 67-33% of cathodic metal may be preferred. At these percentages, less than half of the anodic metal is fully encapsulated by the non-corroding cathodic metal and trapped within the coating. Thus, in general, the combined coatings (also referred to as co-deposited coatings) may include more than 25% (e.g., 30% or greater, 35% or greater) by volume of anodic metal that is co-deposited with the cathodic metal. In some variations, the remainder of the coating (e.g., between 5% and 75%,) may be cathodic metal. Thus, the percent of anodic metal co-deposited with cathodic metal may be between 25%-95% (e.g., between about 30% and about 95%, between about 30% and about 90%, between about 30% and about 80%, between about 30% and about 70%, between about 25% and 75%, between about 25% and 80%, between about 25% and 85%, between about 25% and 90%, between about 35% and 95%, between about 35% and 90%, between about 35% and 85%, between about 35% and 80%, between about 35% and 75%, between about 35% and 70%, between about 35% and 65%, etc.), with the remainder of the coating being cathodic metal. Further, the coating (or at least the outer layer of the coating) may be primarily (e.g., >95%) formed of anodic and cathodic metals distributed in the micro-domains as described herein. In some variations the coating may also include one or more additional materials (e.g., a metal, polymer, or the like). The additional material(s) may be inert (e.g., not participating in the galvanic reaction between the anodic metal and the cathodic metal), or it may be electrically conductive. For example, the additional material may be co-deposited with the anodic and cathodic metals, and may also be distributed in a non-homogenous manner.

For example, a mixed coating may be formed using a PVD-system. Vaporization of metal components may be performed on a substrate (with or without an adhesive layer), e.g., using an arc and/or a magnetron sputter from metallic targets. Mixed coatings may be produced by simultaneous vaporization of both metals while the substrate is held fixed, or is moved (e.g., rotated). After coating, the coated materials may be cleaned, e.g., using an argon plasma and/or other methods.

As mentioned, any of the coatings described herein may be of any appropriate thickness. For example, the coatings may be between about 500 microinches and about 0.01 microinches thick, or less than about 200 microinches (e.g., between about 10 microinches and about 500 microinches), less than about 150 microinches, less than about 100 microinches, less than about 50 microinches, etc. The thickness may be selected based on the amount and duration (and/or timing) of the release of anodic metal. In addition, the coatings may be patterned, e.g., so that they are applied onto a substrate in a desired pattern, or over the entire substrate. As mentioned and described further below, different combined coatings may be applied to the same substrate. For example, a combined coating of silver/platinum may be applied adjacent to a combined coating of zinc/platinum, etc. The different combined coatings may have different properties (e.g., different anodic metal, different anodic/cathodic metal percentages, different thicknesses, etc.) and therefore different release profiles. Combinations in which different combined coatings are in (electrical) contact with each other may also have a different release profile than combinations in which the different coatings are not in electrical contact. For example, a material may include a first combined coating of zinc and a cathodic metal (e.g., zinc/platinum) and a second combined coating of silver and a cathodic metal (e.g., silver/platinum). If the first and second combined coatings are in electrical contact, the zinc will be galvanically released first. If the first and second combined coatings are not in electrical contact, then both zinc and silver will be concurrently released (though zinc may be released more quickly and my diffuse further).

Figure 2A:
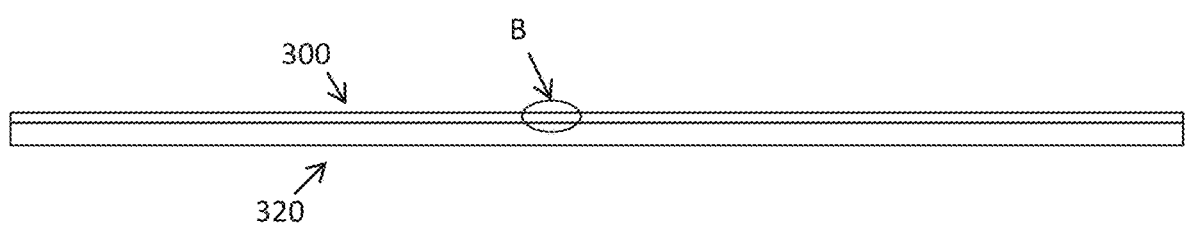
FIG. 2A shows a cross-sectional view through one example of a substrate having a combined coating, comprising an anodic metal that is co-deposited with a cathodic metal.

For example, FIG. 2A illustrates one example of a substrate 320 onto which a combined coating of anodic and cathodic metals have been co-deposited 300. The substrate may be, for example, a bioabsorbable material. In some variations the substrate may be an adhesive layer, e.g., when applying the coating to some medical devices. For example, an adhesive layer may be a metal layer such as an undercoating of titanium or tantalum. The undercoating may be of any appropriate thickness (e.g., the same thickness or smaller than the thickness of the galvanically releasing coating). In some variations the undercoating is thicker than the coating of the non-homogeneous mixture of anodic and cathodic metals that are galvanically released. Although an undercoating may be used in some variations, the coatings of anodic and cathodic metals described herein may be coated directly onto a medical device (e.g., implant) without the need for an undercoating.

Although the combined coatings described herein may be used with any substrate (even non-bioabsorbable substrates), any of the examples described herein may be used with bioabsorbable substrates. In the example of FIG. 2A the dimensions (thicknesses of the substrate and coating) are not to scale. For example, the coating may be less than 100 microinches thick. The substrate may be any thickness. In FIG. 2A, region B shows a portion of the coating and substrate, which is illustrated in the enlarged view of FIG. 2B.

Figure 2B:
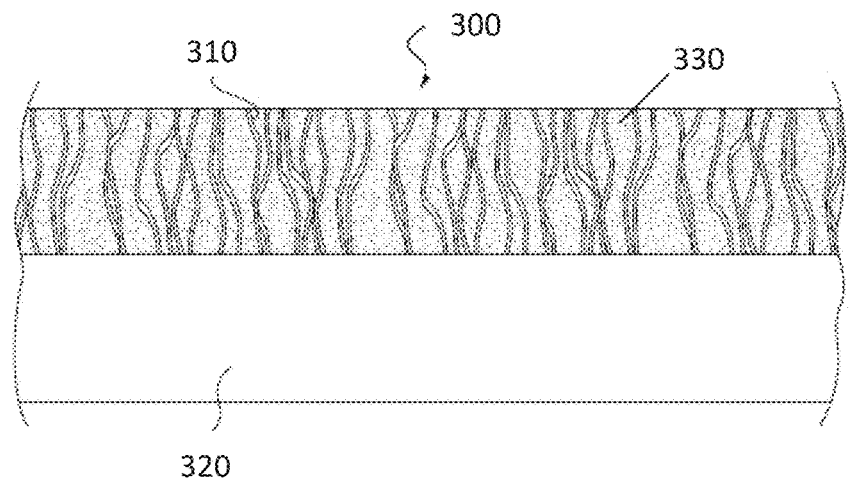
FIG. 2B is a schematic representation of an enlarged view of a portion of the coated substrate of FIG. 2A, schematically illustrating micro-domains or veins of anodic metal (not to scale) within a cathodic matrix.
Figure 2C:
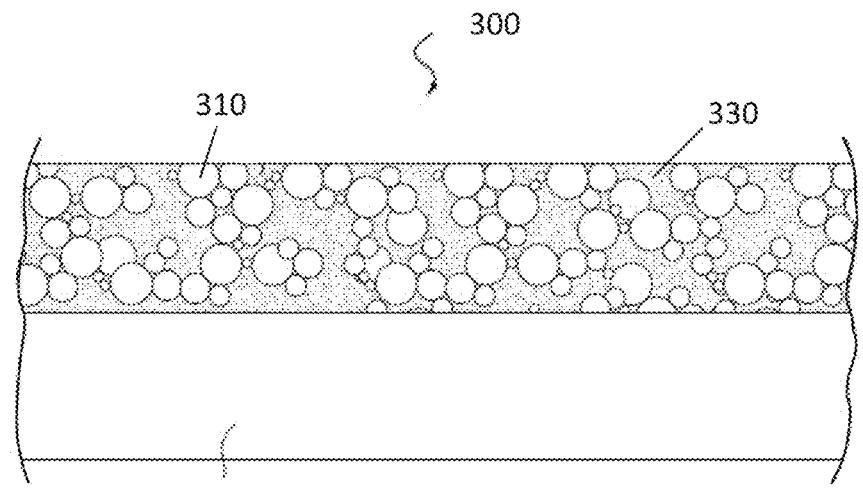
FIG. 2C is another schematic representation of an enlarged view of a portion of the coated substrate of FIG. 2A.

In FIG. 2B, a portion of the substrate 320 (e.g. a bioabsorbable substrate) is shown coated with a combined coating 300. The anodic metal, e.g., silver, 310 is shown forming veins or microregions within the cathodic metal 320. In this example, the silver is schematically illustrated as forming veins through a matrix of cathodic metal, e.g., platinum, not shown to scale. The actual microdomains may be much smaller, and filamentous; for example, the microdomains may be on the order of 10-1000 Angstroms (or more) across. FIG. 2C is another schematic illustration of a section through a portion of a combined coating on a substrate, showing microdomains of anodic metal (e.g. silver) 310, within a matrix of cathodic metal (e.g., platinum) 320. In FIGS. 2B and 2C the majority of the microdomains of anodic metal are connected in continuous paths to the outer surface of the coating 300, allowing galvanic release of the anodic material.

Figure 2D:
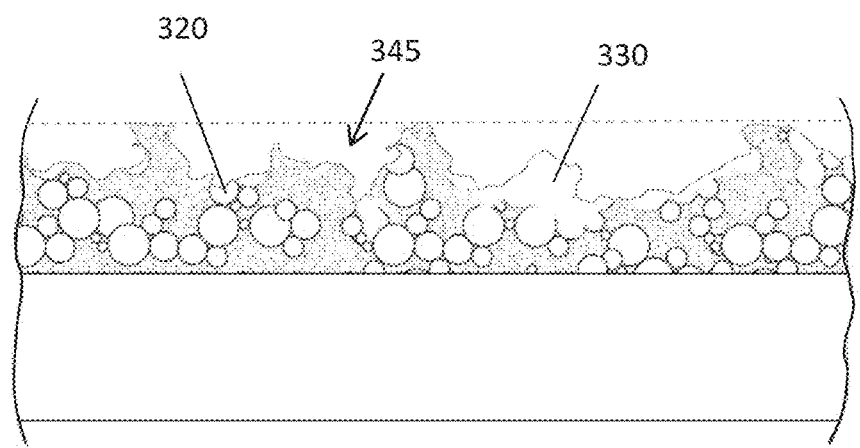
FIG. 2D is an example of the galvanic release (and corrosion) of a coating on a substrate such as the one shown in FIG. 2A.

FIG. 2D illustrates an example of the coating of FIG. 2C during the galvanic release process, in which the implant including the substrate and the combined coating is place into the body, so that the coating is exposed to blood. As shown in FIG. 2D, the anodic metal (silver) in the coating is progressively corroded as ions of silver are released into the body to locally diffuse and provide regional antimicrobial treatment. In this example the anodic metal (e.g., silver) 320 exposed to the surface is release, leaving a negative impression 345 in the cathodic metal 320. Regions of the cathodic metal that are left behind may remain coated (though the substrate may also be biodegrading simultaneous with the release of anodic metal, not shown). Typically, when the substrate is part of an implanted apparatus, the coating layer is thin enough that any remaining cathodic metal (e.g., platinum) is small enough to be ignored or easily cleared by the body.

The combined layers are generally formed by co-depositing the anodic metal and the cathodic metal onto the substrate. For example, a combined layer may be formed by simultaneously sputtering the two metals onto the substrate to the desired thickness. For example, both silver and platinum may be placed into a sputtering machine and applied to the substrate. The amount of cathodic material and anodic material may be controlled, e.g., controlling the percentage of the coating that if anodic metal and the percentage that is cathodic (e.g., 30%-70% anodic/70-30% cathodic, such as 40% silver/60% platinum, etc.). This sputtering process results in a non-uniform pattern, as discussed above, and schematically illustrated in FIGS. 2B-2C, which may be observed. Alternatively, combined layers may be formed by vacuum deposition, or any other technique that can co-deposit the two (or more) metals onto the substrate. Formation of the coating(s) may include masking, for example, locating coatings in particular regions of the substrate.

In general, any of the substrates (e.g., bioabsorbable substrates) described herein may be applied in a pattern, including patterns of multiple different combined coatings. Further, coatings may be applied over only a portion of the substrate, which may allow more localized release of the antimicrobial ions and may prevent the coating from interfering with the properties of the substrate and/or the device that the substrate is part of (e.g., flexibility, surface characteristics, etc.). For example, FIGS. 3A-3C show a top view of a substrate coated with various combined coatings (co-deposited anodic and cathodic metals).

Figure 3A:
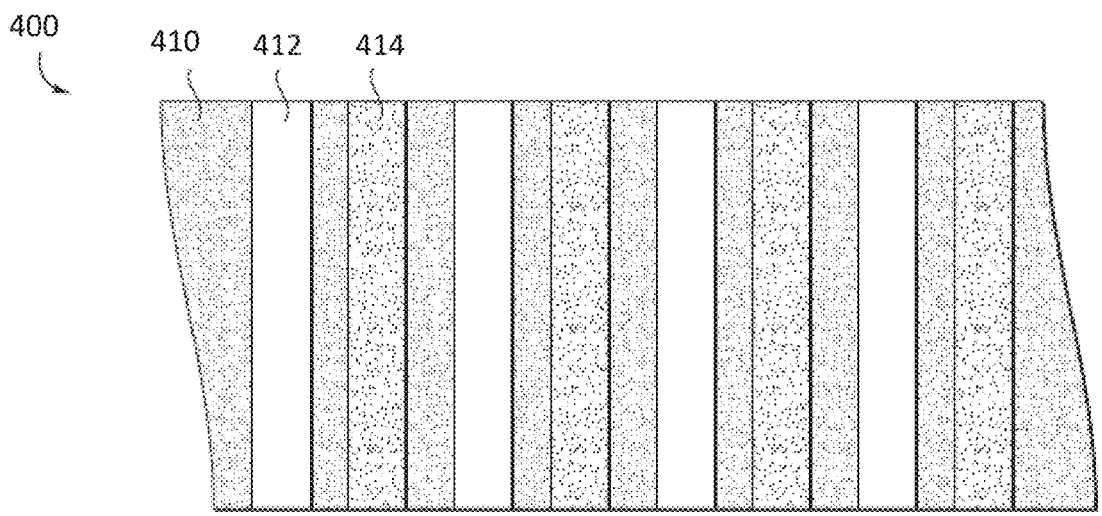
FIGS. 3A-3C illustrate top views of alternative variations of coating patterns for different combined coatings, such as silver/platinum and zinc/platinum.
Figure 3B:
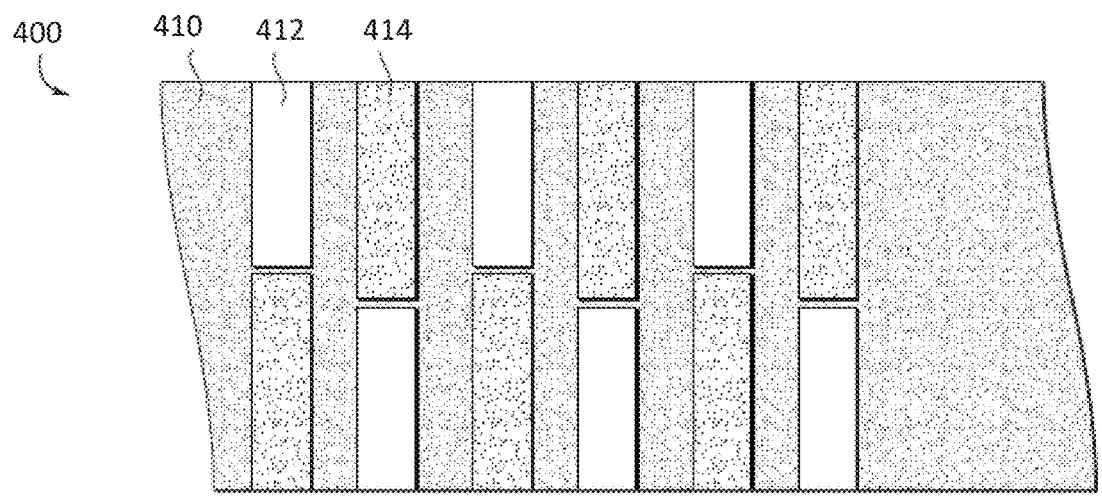

For example, in FIG. 3A, the surface of the substrate 410 of an implant 400 that includes alternating patterns of a first combined coating 412 of silver/platinum that have been co-deposited onto the substrate and a second combined coating 414 of zinc/platinum co-deposited onto the substrate. In this example the first and second coating regions are formed into strips extending along the width of the substrate; the first and second coating regions do not overlap and are not in electrical contact with each other. Thus, the silver ions in the first coating region(s) 412 will be galvanically released concurrently with the zinc ions galvanically released from the second coating region(s) 414 when exposed to an electrolytic bodily fluid (e.g., blood), corroding the two layers. FIG. 3B shows another example of a pattern of a first combined coating 412 (e.g., silver/platinum) and a second combined coating 414 (zinc/palladium) that are arranged with alternating stripes on the surface of the substrate 410, where the stripes are end-to-end with each other.

Figure 3C:
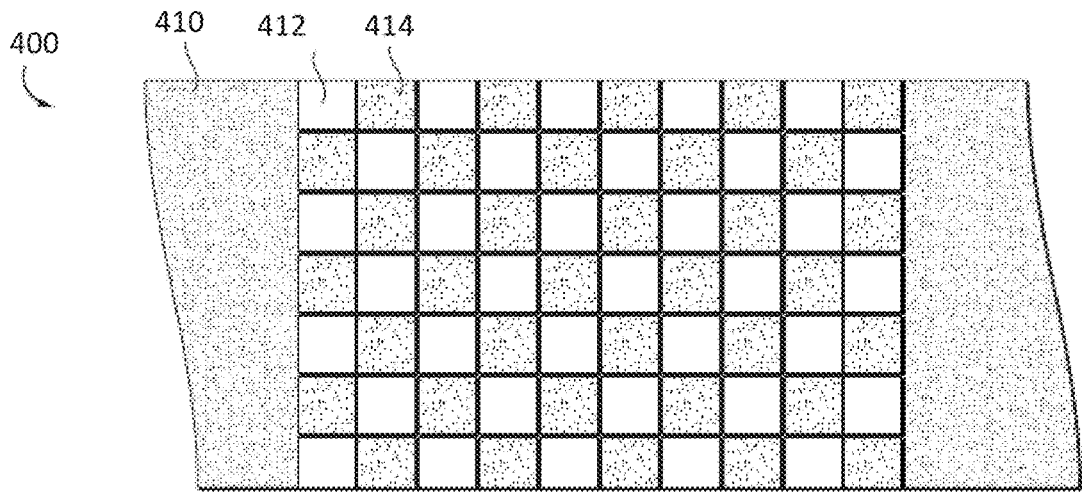

FIG. 3C shows another variation of a surface 410 of an implant 400 that includes a pattern, shown as a checkerboard pattern, of first and second combined coatings. In FIG. 3C, the edges of the different coating regions may contact each other or may be separated by a channel so that they are not in electrical contact for the galvanic reaction. For example, if the first and second regions do contact each other so that they are in electrical contact, then the galvanic reaction may drive the release of the zinc ions before the release of the silver ions; once the zinc has corroded, the silver ions may be released.

In general, there may be some benefit to including multiple coatings, and in particular coatings having multiple anodic metals. The antimicrobial region around the coated implant may be made larger and the ions may be released over a longer time period, than with a single type of anodic coating alone.

As mentioned, the combined coatings of co-deposited anodic and cathodic metals could be formed in any pattern.

Figure 24A:
FIGS. 24A-24C illustrate exemplary patterns of coatings that may be made.
Figure 24B:
Figure 24C:

Other patterns that may be applied include patterns of any of the coatings (or multiple coatings) in one or more of a sinusoidal pattern, cross-hatched pattern, a mesh pattern, a grid pattern, a web pattern, a zig-zag pattern, etc. Patterns may be formed by masking during the application (e.g., vapor deposition) process. For example, FIGS. 24A-24C illustrate patterns of the coatings described herein that may be particularly useful. For example, in FIG. 24A, a cross-hatched pattern is shown. These patterns may be formed on any appropriate substrate, including on catheters, tubing, and other apparatuses. In particular, these patterns may be applied to flexible and/or bendable surfaces/substrates. FIG. 24B shows a coating pattern that may be formed, e.g., on a catheter or tube and has a diagonal-hatched pattern. These patterns may allow flexibility and still provide antimicrobial coverage. In some variations the patterns (e.g., mesh, web, etc. patterns) may include regular gaps or openings exposing the bare surface/substrate; these gaps may be a maximum size, for example, less than 2 mm (e.g., less than 1.5 mm, less than 1.0 mm, less than 0.9 mm, less than 0.8 mm, less than 0.7 mm, less than 0.6 mm, less than 0.5 mm, etc.) in diameter.

FIG. 24C illustrates one example of a sinusoidal pattern of a coating applied to a surface of an apparatus.

Bioabsorbable Substrates

In some variations, the substrate is bioabsorbable and/or biodegradable. For example, the substrate may be formed as a flexible filament, and the coating of anodic and cathodic metals that may corrode to release anodic ions may allow the flexible filament to remain flexible. Galvanic release results in degradation (e.g., corrosion) of the coating.

The substrate onto which the combined coatings may be applied may be any appropriate substrate, and in particular, may be a bioabsorbable substrate. Examples of bioabsorbable materials that may be used includes polymeric materials such as: polylactic acid (PLA), poly(lactic-co-glycolic acid) (PLGA), polyglycolide (PGA), polyglycoside-co-trimethylene carbonate (PGTMC), poly(caprolactone-co-glycoside), poly(dioxanone) (PDS), and poly(caprolactone) (PCL), and combinations of these.

In general, bioabsorbable materials for medical applications are well known, and include bioabsorbable polymers made from a variety of bioabsorbable resins; for example, U.S. Pat. No. 5,423,859 to Koyfman et al., lists exemplary bioabsorbable or biodegradable resins from which bioabsorbable materials for medical devices may be made. Bioabsorbable materials extend to synthetic bioabsorbable or naturally derived polymers.

For example, bioabsorbable substrates may include polyester or polylactone selected from the group comprising polymers of polyglycolic acid, glycolide, lactic acid, lactide, dioxanone, trimethylene carbonate, polyanhydrides, polyesteramides, polyortheoesters, polyphosphazenes, and copolymers of these and related polymers or monomers. Other bioabsorbable substrates may include substrates formed of proteins (e.g., selected from the group comprising albumin, fibrin, collagen, or elastin), as well as polysaccharides (e.g., selected from the group comprising chitosan, alginates, or hyaluronic acid), and biosynthetic polymers, such as 3-hydroxybutyrate polymers.

The bioabsorbable substrate may be absorbed over a predetermined time period after insertion into a body. For example, the bioabsorbable substrate may be absorbed over hours, days, weeks, months, or years. The substrate may be bioabsorbed before, during or after release of the anodic metal ions from the combined coating. In some variations the release of the antimicrobial ions is timed to match the degradation/absorption of the substrate. Further, the absorption of the substrate may facilitate the release of the anodic metal ions. For example, some of the bioabsorbable substrates described herein may result in a local pH change as the substrate is bioabsorbed; the release of the metal ions may be facilitated by the altered pH.

Figure 4:
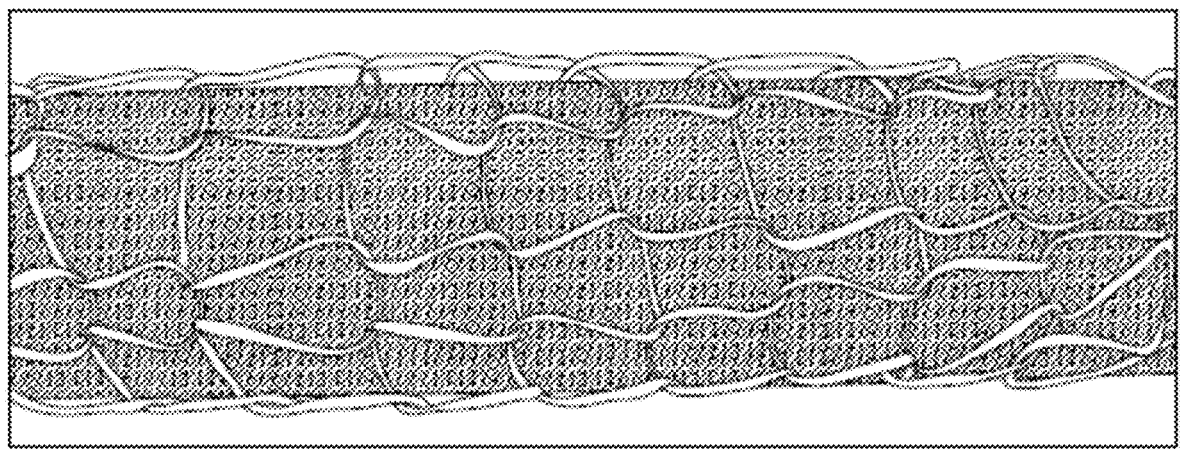
FIG. 4 is an example of a bioabsorbable pouch woven from one or more strands, wherein the strands of the pouch are coated with the combined coatings described herein for release of antimicrobial ions.

FIG. 4 shows an example of a pouch device formed from woven lengths of bioabsorbable filament that is flexible. The filament is formed of a bioabsorbable polymer, PGLA, and this bioabsorbable substrate has been coated with the combined anodic metal/cathodic metal coating described above. In FIG. 4A, the pouch of PGLA fibers coated with (e.g., by vapor deposition) co-deposited silver and platinum galvanically releases silver ions after insertion into the body. The release of anodic metal ions (e.g., silver ions) is enhanced as the bioabsorbable substrate (e.g., PGLA) is hydrolyzed. Hydrolysis lowers the local pH and this may increase solubility of silver and bio-absorption.

The pouch of FIG. 4 may be used similarly to those described in U.S. Pat. No. 8,591,531, herein incorporated by reference in its entirety.

In general, the bioabsorbable substrate may be formed into any appropriate shape or structure. For example, a bioabsorbable substrate may be a filament that is coated, completely or partially, by one or more of any of the combined coatings of anodic and cathodic metals co-deposited onto the bioabsorbable substrate. Coated strands (e.g., filaments, strings, wires, etc.) of bioabsorbable substrate may be used by themselves, e.g., as suture, ties, etc. within a body, or they may be used to form 2D or 3D implants, for example, by weaving them. The combined coatings described herein may be coated onto these structures either before or after they have been formed. For example, a coated filament may be woven into a net (or into a pouch for holding an implantable device, as shown in FIG. 4), or the filament may be woven into a net and then coated.

Figure 5A:
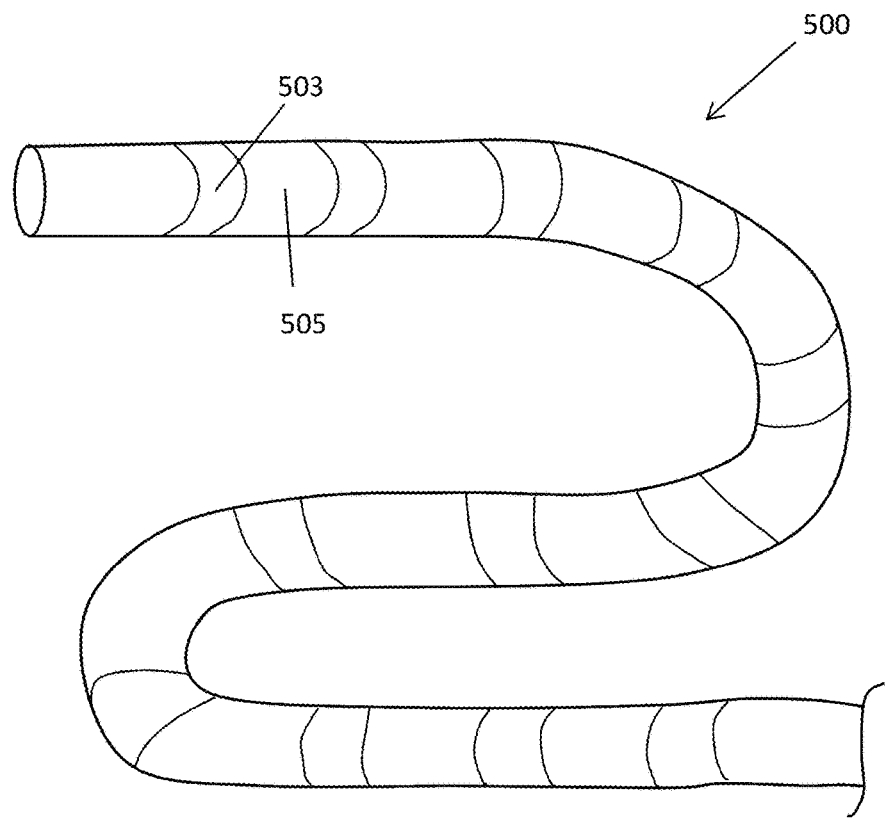
FIG. 5A illustrates a fiber or filament (e.g., suture fiber) coated with a striped pattern of a combined coating for galvanic release of metal ions.

FIG. 5A shows an example of a filament that may be formed of a bioabsorbable substrate that is coated with a combined anodic/cathodic metal coating for galvanic release of anodic metal ions. In FIG. 5A, the fiber 500 may include uncoated regions 505 alternating with coated regions 503. The coated region(s) may be a spiral shape around the fiber, a ring around the fiber (as shown in FIG. 5) or any other pattern. Multiple coatings may be used (see, e.g., FIGS. 3A-3C). The coated fiber may retain its flexibility. In some variations the fiber may be used, e.g., as a suture.

Figure 5B:
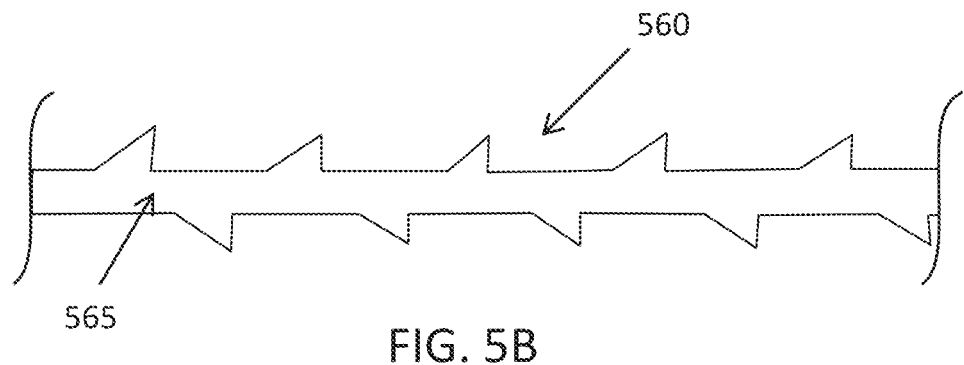
FIG. 5B illustrates a portion of a barbed suture fiber coated as described herein.
Figure 5C:
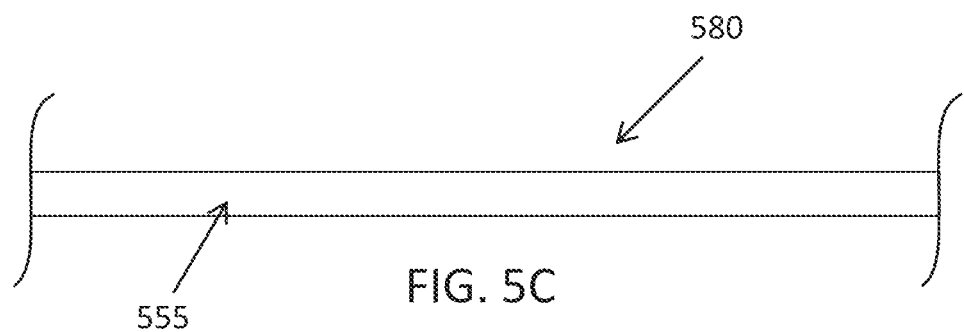
FIG. 5C is a portion of a suture fiber that is coated as described herein.
Figure 5D:
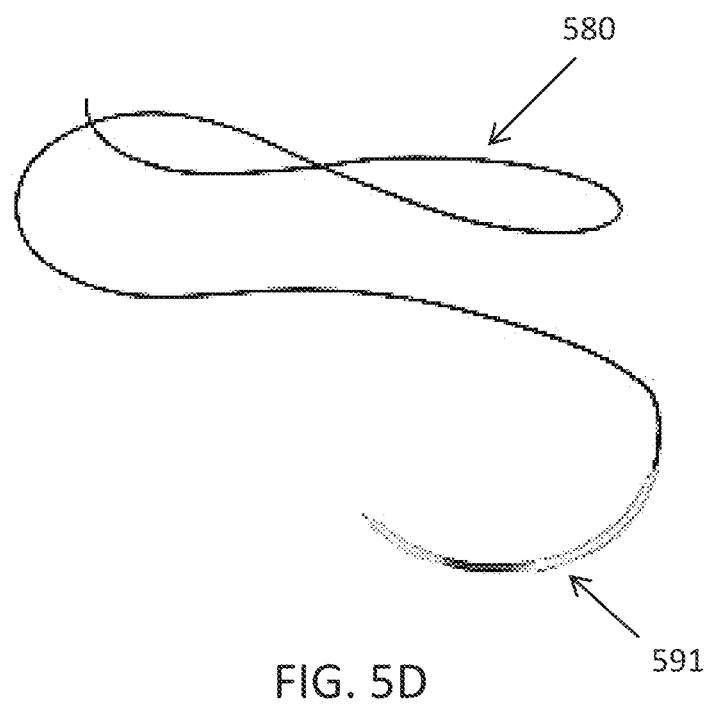
FIG. 5D is an example of a needle and suture (shown as a combined needle preloaded with suture) in which both needle and suture are coated as described herein.

FIGS. 5B-5D and 6 illustrate different variations of sutures that may be coated as described herein. Note that although some of these substrates forming the suture are bioabsorbable, they do not need to be. In some variations, the suture material (the substrate onto which the galvanically releasable coating is applied) is not biodegradable or bioabsorbable. Any variation of suture material may be used. For example, the suture material may be a barbed suture, as shown in FIG. 5B. The barbed suture 560 may be coated 565 or otherwise treated to include the co-deposited coating of anodic metal (e.g., 40% by volume of silver) and cathodic metal (e.g., 50% by volume of platinum) arranged with continuous microdomains of the anodic (and/or cathodic) metal extending from the outer side of the outer surface of the coating through the thickness of the coating. An entire length of suture 580 may be coated 585, as shown schematically in FIG. 5C, or just a portion of the suture. The thickness of the coating may be below a threshold, which may help maintain the flexibility of the suture material. For example, the thickness may be between 10 microinches and 50 microinches. FIG. 5D illustrates a suture kit including a length of suture 580 and a needle 591; either or both the suture 580 and needle 591 may be coated. The same or different anodic metal and/or cathodic metal may be used on the needle as the thread. For example, the needle may include the more quickly releasing nickel as the anode, while the thread, which resides longer in the body, may use and anodic metal of silver.

Figure 6:
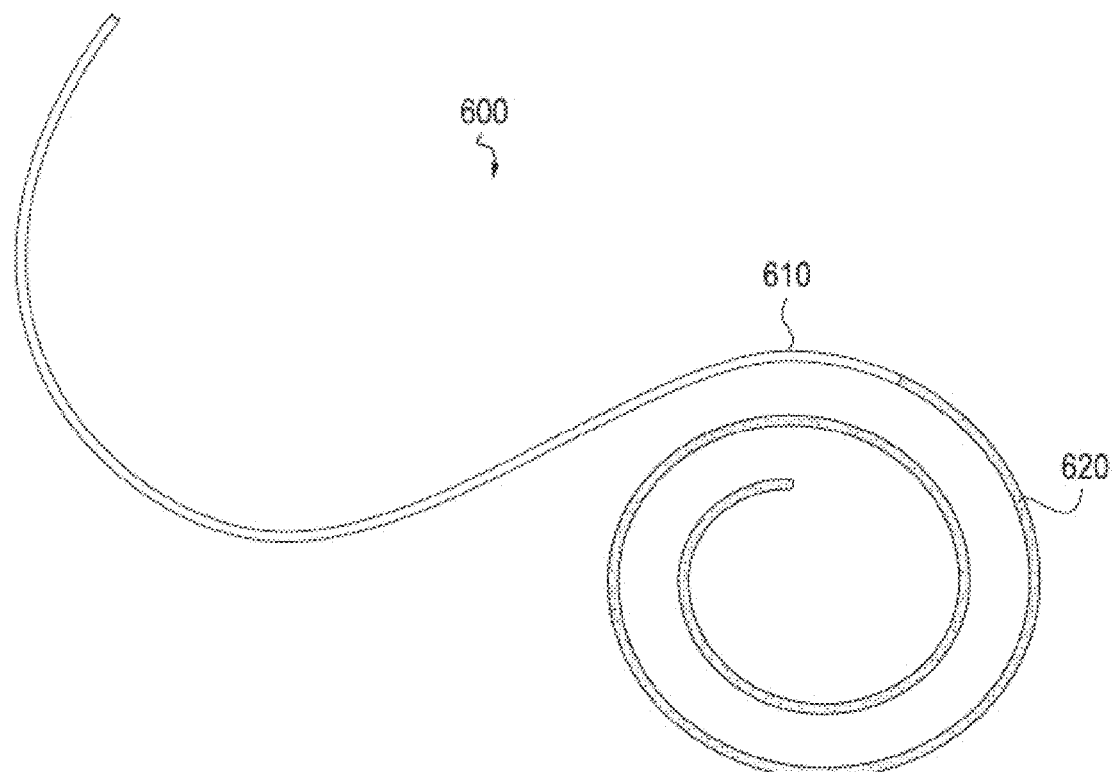
FIG. 6 is an example of a length of suture formed from a bioabsorbable substrate onto which a combined coating has been regionally applied (e.g., near the distal end).

FIG. 6 shows another example of a suture 600 that is coated 620 over the distal portion of the suture, which may be used in the body. The suture may be pre-loaded on a device (including an implant, needle, etc.). The suture may be formed of a bioabsorbable substrate 610 onto which the coating is applied.

In any of the devices described herein, the coating may be made directly onto the substrate. In some variations the coating may be made on top of another coating (e.g., a primer coating) which may be made to prepare the substrate for the coating. Examples of primer coatings are adhesion coatings. An example of a primer coating may include titanium and/or tantalum undercoatings, as described above.

Figure 7:
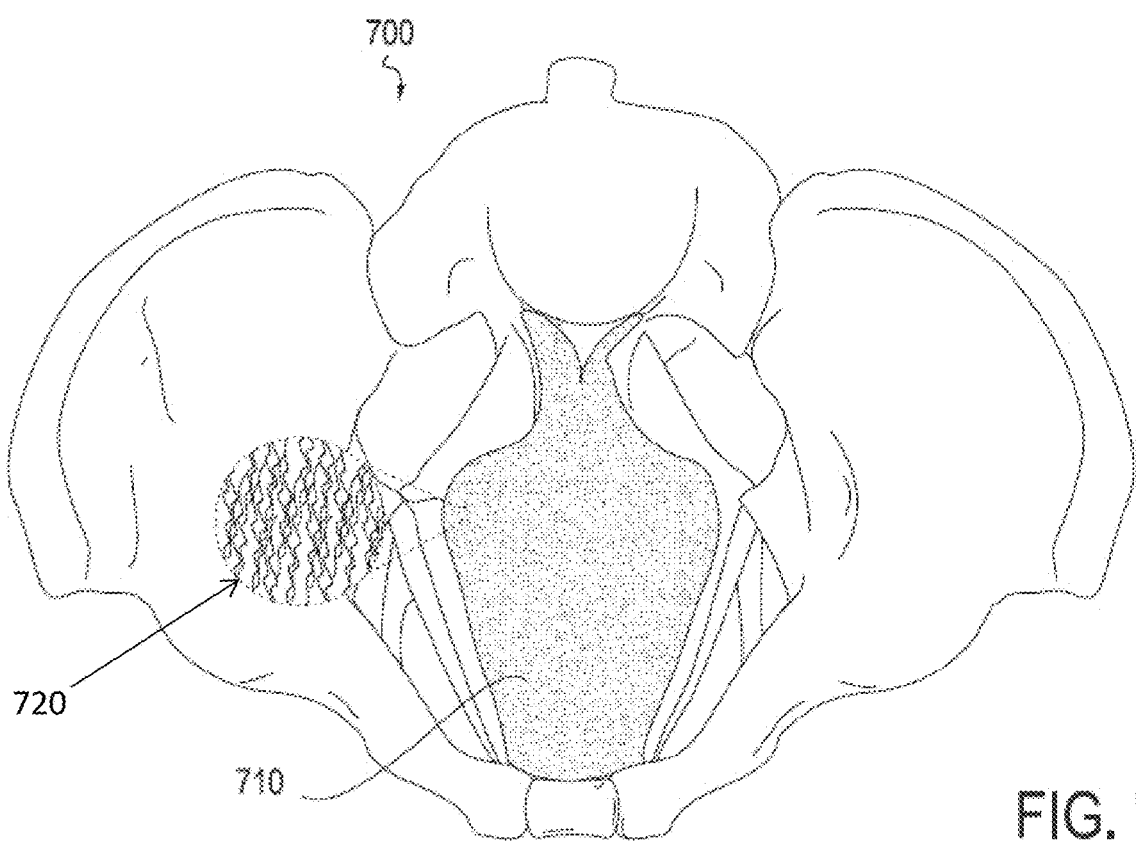
FIG. 7 illustrates one example of a medical device configured as a transvaginal mesh having a combined coating for release of metal ions after insertion into the body.

Additional examples of woven structures are shown in FIGS. 7-11. In FIG. 7, the device 700 is formed of filaments 710 woven or arranged into a mesh (shown in the enlarged view 720) that are coated with a combined coating (or multiple types of combined coatings) as described herein. In this example, the mesh formed is configured as a transvaginal mesh (intravaginal mesh) that may be used for the treatment of vaginal prolapse, for example. Slings or other anatomical support structures, either durable or biodegradable, could also be formed. These devices may galvanically release one or more type of anionic metal ion having antimicrobial effect. For example the mesh may be coated with a coating of silver/platinum that is co-deposited onto the mesh or the fibers forming the mesh for galvanic release of silver from the coating.

FIGS. 8A and 8B illustrate another example of a structure, shown as a woven structure, that may also be configured as a non-woven (e.g., solid) structure. In FIG. 8A the device 400 is a patch or plug that may be used for treating a hernia. In this example, the patch is a woven mesh that includes two types of combined coatings: silver/platinum and zinc/platinum in different regions over the surface of the patch. Darker regions 803 may indicate the silver/platinum co-deposited coating regions, while the lighter regions 805 represent co-deposited zinc/platinum regions. The entire patch outer surface or only a portion of the outer surface may be coated; in FIG. 8A, only discrete regions are shown as coated, for the sake of simplicity. FIG. 8B shows an enlarged view illustrating the fibers forming the weave of the patch. As shown in FIG. 8B, only some of the fibers are coated (e.g., every other fiber of the warp); in some variations, alternating fibers in one direction (warp) are coated with different anodic/cathodic metals, while fibers in the opposite direction (weft) are uncoated.

FIG. 9 illustrates another example of a woven material, formed of a bioabsorbable fiber, coated with the combined coatings described herein for galvanic release of antimicrobial metal ions. In FIG. 9, the device is a patch that could be used, e.g., within the knee after surgery, to reduce the chance of infection. In this example, as in FIGS. 8A and 8B above, the patch may include filaments/fibers having different coatings (e.g., silver/platinum, zinc platinum, silver palladium, zinc palladium, etc.) and/or different regions on the patch, as shown by the light and darker regions in FIG. 9. In some variations the patch may be worn outside of the body, e.g., it is "implanted" by placing it over a wound, rather than entirely within the body. Blood in the wound region may act as the electrolytic fluid, allowing galvanic release of the metal ions.

Figure 10:
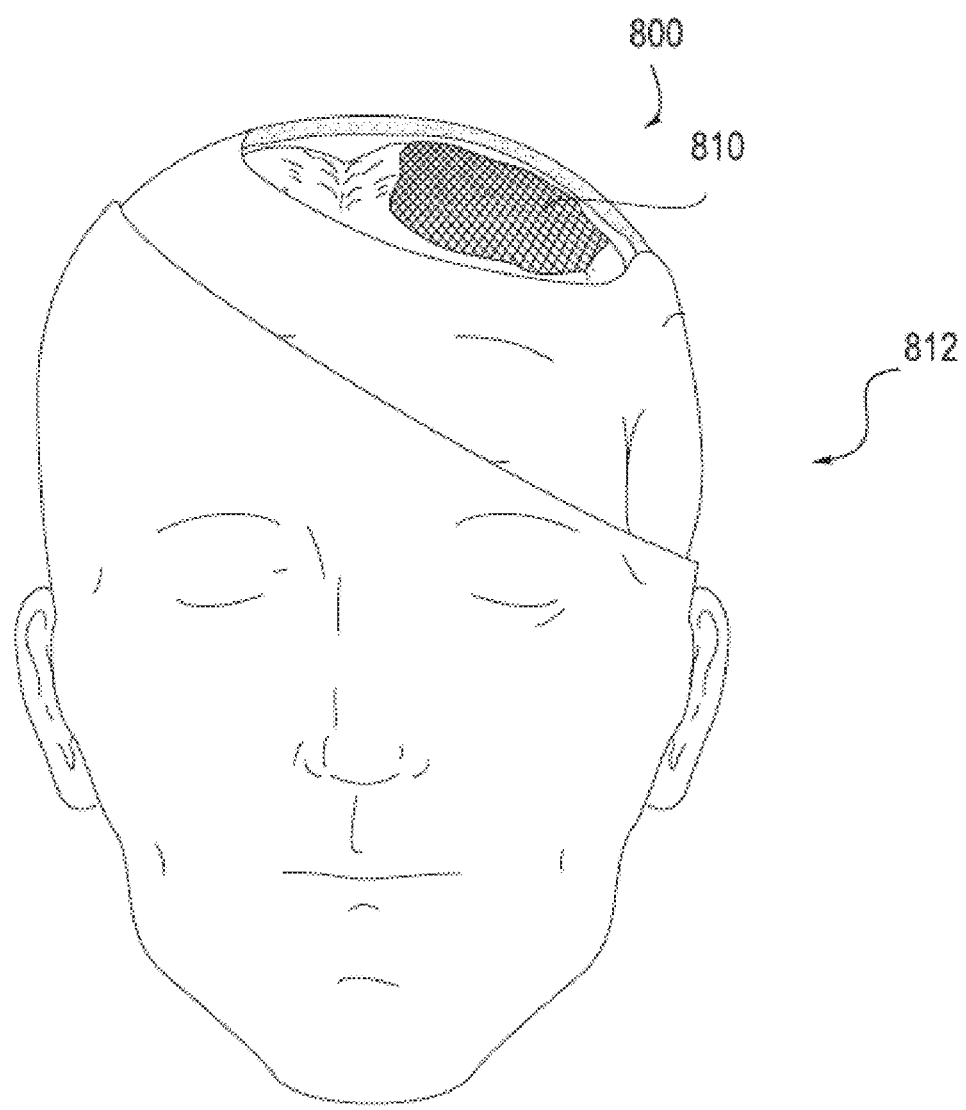
FIG. 10 illustrates one variation of an artificial dura (mesh) including a combined coating for galvanic release of metal ions.

Similarly, FIG. 10 illustrates a dural replacement mesh 810 that may be implanted into a subject's head 812 to replace dural matter following trauma and/or surgery. The mesh may be formed of a non-bioabsorbable material (or a bioabsorbable material) that is coated as described above so as to galvanically release antimicrobial metal ions.

Figure 11:
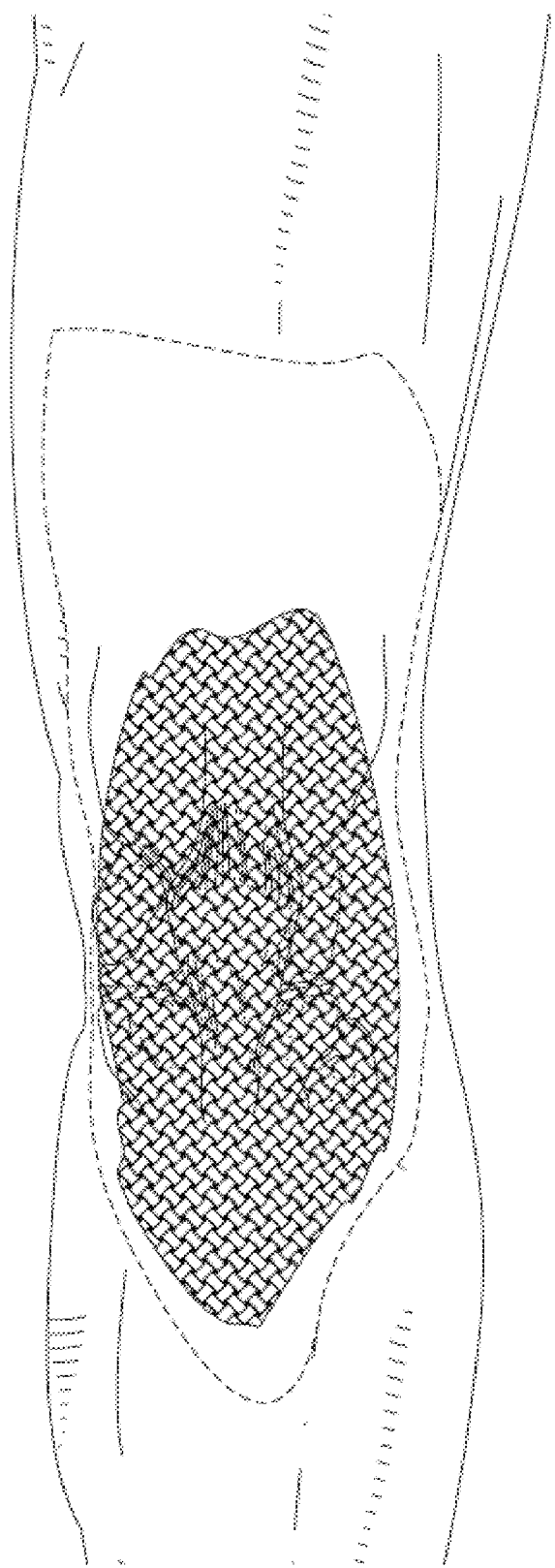
FIG. 11 shows an example of a material that may be used as within a wound or surgical site to prevent or treat infection. The material may be a porous and/or bioabsorbable mesh that is configured to galvanically release metal ions.

FIG. 11 illustrates another example of a fabric or mesh that may be implanted into a patient as part of a surgical procedure. In FIG. 11, the mesh is a woven fabric that has been coated with one or more combined coatings of anodic and cathodic metals co-deposited on the substrate (e.g., bioabsorbable substrate) for galvanic release of metal ions. The material may be used, for example, as part of a large joint procedure such as knee replacement, or spinal surgery (e.g., fixation using rods, screws, etc.) in place of currently used antibiotic powers. For example the coated bioabsorbable mesh could be in, around, or over the surgical site and used to galvanically release antimicrobial ions following surgery. The implant (material) would break down over time, and be absorbed following implantation (e.g., within 30 days following the procedure), allowing sufficient time for the patient to recover and avoid infection potentially introduced by the procedure and/or the resulting wound.

Although the devices described herein include flexible, e.g., filament or mesh, structures, the devices may also be configured as rigid or more traditional surgical implants, including screws, rods, staples, cannulas, etc. The substrate may be bioabsorbable.

Figure 12A:
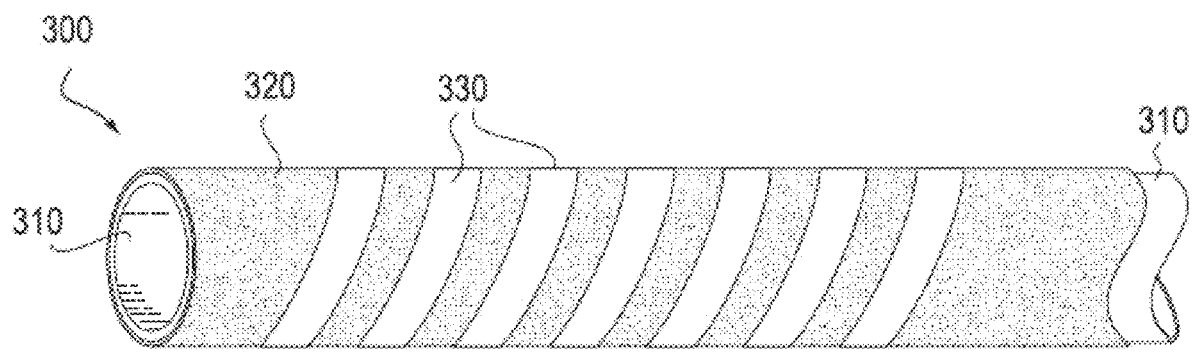
FIGS. 12A and 12B show side perspective and end views, respectively of one variation of a cannula including a pattern of a combined coating for the release of antimicrobial metal ions.
Figure 12B:
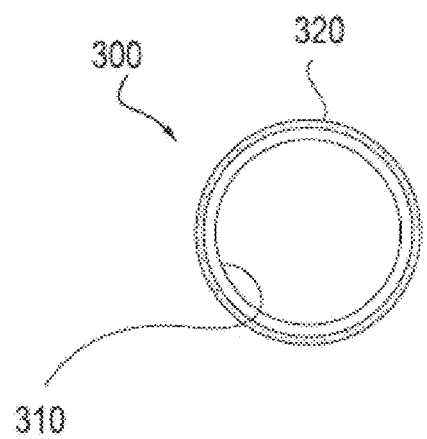

For example, FIGS. 12A-12B shows one variation of a cannula that may be used within a body and galvanically release antimicrobial metal ions. In FIG. 12A, the cannula 300 includes a substrate 320 onto which a combined coating 330 is applied in a spiral pattern. The combined coating galvanically releases anodic metal ions (e.g., silver, zinc, copper), is includes the anodic metal that has been co-deposited with cathodic metal (e.g., platinum, palladium, etc.). In this example, the inner surface 310 of the cannula 300 may also be separately coated with a combined coating (the same or a different coating). FIG. 12B shows a side view of the catheter of FIG. 12A.

Any of the devices described herein may be used as part of a surgical procedure within a body (e.g., human, animal, etc.). In general, the combined coatings described herein may be implanted into the body and may galvanically release metal ions over an extended period of time (e.g., days, weeks, months). For example, in some variations the coating and/or apparatus (e.g., device) may be configured to galvanically release metal ions for 30 days, 60 days, 90 days, or more.

The anti-microbial coatings, devices and systems described herein may use two or more types of metal ions with anti-microbial properties, such as silver and zinc. The zone of inhibition of microbial activity/growth formed around the coated devices due to the released metal ions may be enhanced where two different types (e.g., silver and zinc) are released. The combination of zinc and silver has been observed to have a synergistic effect compared to either metal alone.

Further, when the combined coatings described herein are used in combination with a bioabsorbable (e.g., biodegradable) substrates or material, the metal ions may form complexes with the byproducts of degradation of the substrate (e.g., polymeric substrates including PLA, PLGA, PGA) such as lactate, galactate, or glucoate. These substrates may increase the anti-microbial activity. For example, the range of diffusion of the anionic metal ions (e.g., zinc, silver, etc.) may be increased by the creation of a complex between the metal ions and the polymeric degradation byproduct. Further, as mentioned above, degradation of the polymers may create acidic byproducts such as lactic acid, galactic acid, and/or glycolic acid. The drop in pH and formation of the anionic byproducts may further enhance the rate of the galvanic reaction.

Thus, the apparatuses and methods above may, in some variations, generally take advantage of the use of bioabsorbable substrates that are coated through a co-deposition process of a cathodic metal (e.g., platinum, palladium, gold, etc.) and an anodic metal (e.g., silver, zinc, copper) to form a galvanic circuit in a fluid (e.g., electrolytic) medium to create an antimicrobial zone. The degradation of the bioabsorbable substrate may further enhance this antimicrobial zone, e.g., by forming complexes with the released metal ions to further diffuse the ions as well as to alter the local pH to enhance the galvanic reaction. In general, as described above, the combined coatings described herein can be quite thin and do not compromise the flexibility, chemic structure, strength (e.g., tensile strength) or chemical properties of the underlying substrate(s).

Examples

Any of the coatings described herein may be included on all or a portion of a medical device. For example, any of the following devices may be wholly or partially coated with a mixture of an anodic metal and a cathodic metal as described herein: shunts (e.g., drainage shunts, dialysis shunts, etc.), catheters (e.g., urinary catheters, intravascular catheters, etc.), ports (e.g., portacath, etc.), artificial joints (e.g., total hip, knee, etc.), pacemakers, defibrillators (ICD), pain management implants, neuro-stimulators, neuro-pacemakers, stents, bariatric balloons, artificial heart valves, orthodontic braces, pumps (drug pumps, e.g., insulin pumps, etc.), implantable birth control devices, IUDs, etc.

Any of the coatings described herein may be included on all or a portion of a medical tool. For example, any of the following materials for use in operating on a subject may be wholly or partially coated with a mixture of an anodic metal and a cathodic metal as described herein: surgical gauze, surgical sponges, wound packing materials, augmentation and/or cosmetic implants (e.g., breast/chin/facial implants), surgical retractors, needles, clamps, forceps, and the like.

Figures 13A, 13B:
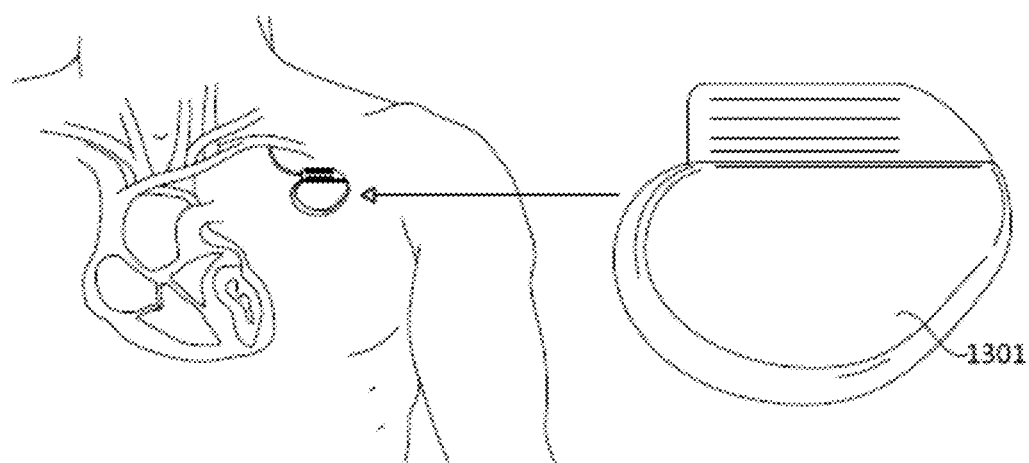
FIGS. 13A and 13B illustrate one example of a medical device (an implantable pacemaker) that may be used with the co-deposited galvanic coatings described herein.

For example, FIG. 13B illustrates one example of an implant that may be coated on an outer surface with any of the antimicrobial coatings comprising a non-homogeneous mixture of anodic and cathodic metals for galvanic release of anti-microbial ions, as described herein, and implant as illustrated in FIG. 13A. In this example all or just a portion of a pacemaker 1301 may be coated on an outer surface with the mixture of between about 30% and 70% by volume of an anodic metal, and between about 30% to 70% by volume of a cathodic metal. The anodic and cathodic metals may be co-deposited on the outer substrate surface to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal. In some variations different regions may be coated with different anodic metals (e.g., forming a pattern of silver, nickel, etc. releasing regions). In some variations the electrical leads (e.g., an outer surface of the leads that are tunneled through the body, as illustrated in FIG. 13A) may be coated as described herein. Similarly, electrical leads for other devices (e.g., neurostimulators) may be coated as described herein. In general, these coatings may terminate before the electrically active regions of the lead.

Figure 13C:
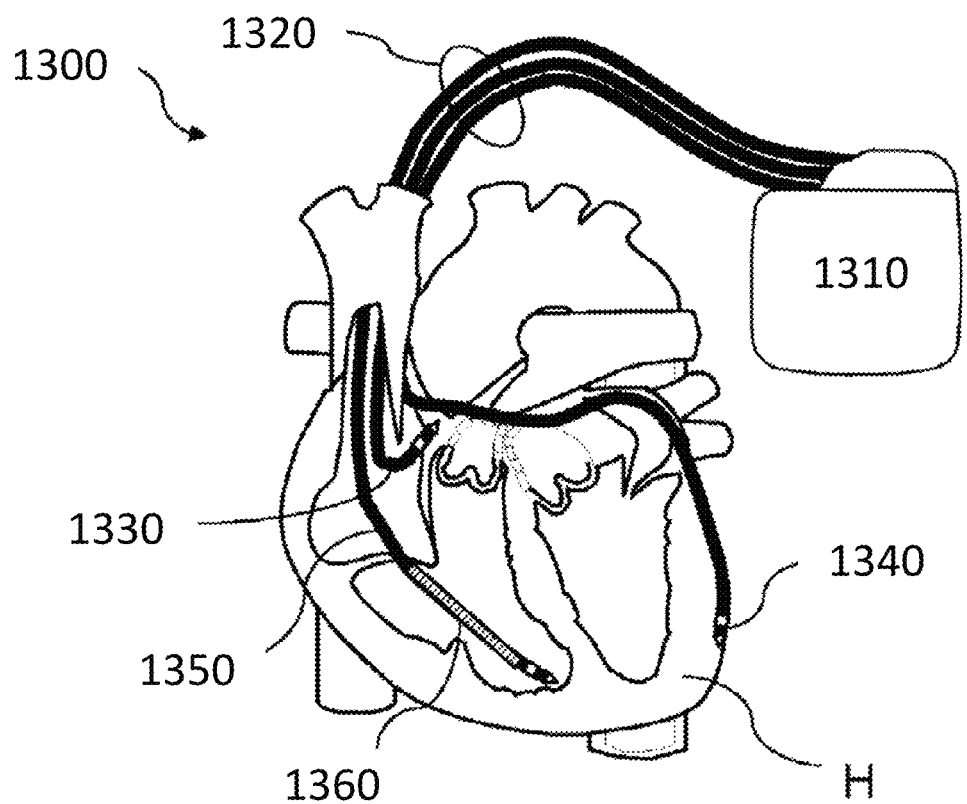
FIG. 13C is a schematic depiction of a conventional cardiac stimulation and defibrillation arrangement.

For example, FIG. 13C shows a schematic depiction of an implantable pacemaker (defibrillator) system 1300 including electrodes implanted in the heart H of a subject (patient). A cardiac stimulation and defibrillation device 1310 is connected to the heart H via an electrode lead 1320 which comprises three lead branches or electrode supply leads 1330, 1340 and 1350. Each lead branch comprises sensing or stimulation electrodes (which are not depicted individually) on or near the distal end thereof, and lead branch 1350 also comprises an elongated defibrillation electrode 1360. In the arrangement shown, lead branch 1330 is placed in the right atrium, lead branch 1340 is placed in the left atrium of the heart H, and lead branch 1350 on which defibrillation electrode 1360 is installed is placed in the right ventricle (RV). As mentioned above, any of the leads described herein may be coated with the mixture of between about 25% to 75% (e.g., 30% and 70%) by volume of an anodic metal, and a cathodic metal that are co-deposited on the outer substrate surface to form a non-uniform mixture of the anodic and cathodic metals. The coatings may include the electrical contacts (not shown) or the contacts may not be coated. Different coatings may be used (e.g., different anodic and/or cathodic metals, different patterns of coating, etc.) may be used. In general, the coating comprises a plurality of microregions or microdomains of anodic metal in a matrix of cathodic metal or a plurality of microregions or microdomains of cathodic metal in a matrix of anodic metal. This coating may be made on the leads without detrimentally affecting the flexibility of the leads. For example, the coating may be applied thin enough to allow the lead to bend easily, while still providing sufficient elution of antimicrobial metal ions (e.g., silver ions) over a long time period (of weeks and months).

Figures 14A, 14B:
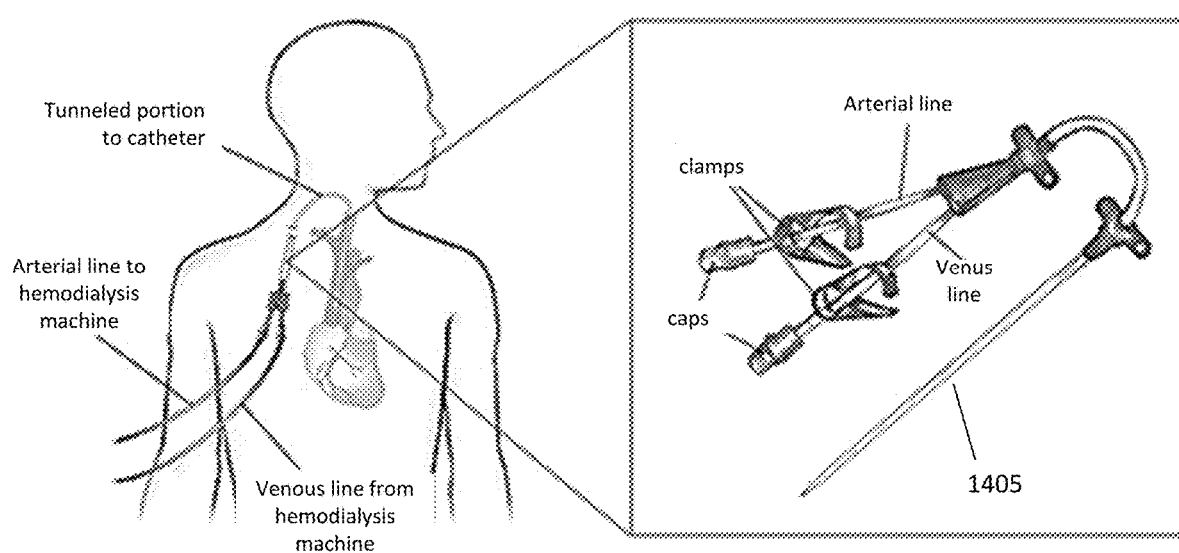
FIGS. 14A and 14B illustrate another example of a medical device (a venous catheter) that may be coated with the co-deposited galvanic coatings described herein.
Figure 15A:
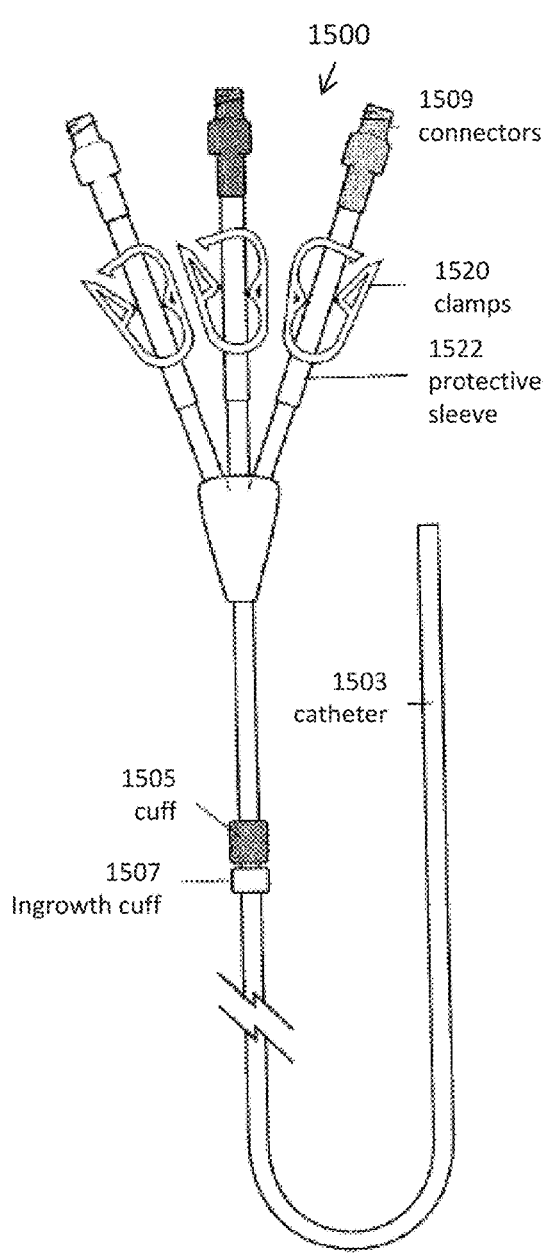
FIGS. 15A and 15B show an example of a catheter (including a cuff) that may include a galvanically released antimicrobial coating that is co-deposited as described herein.
Figure 15B:
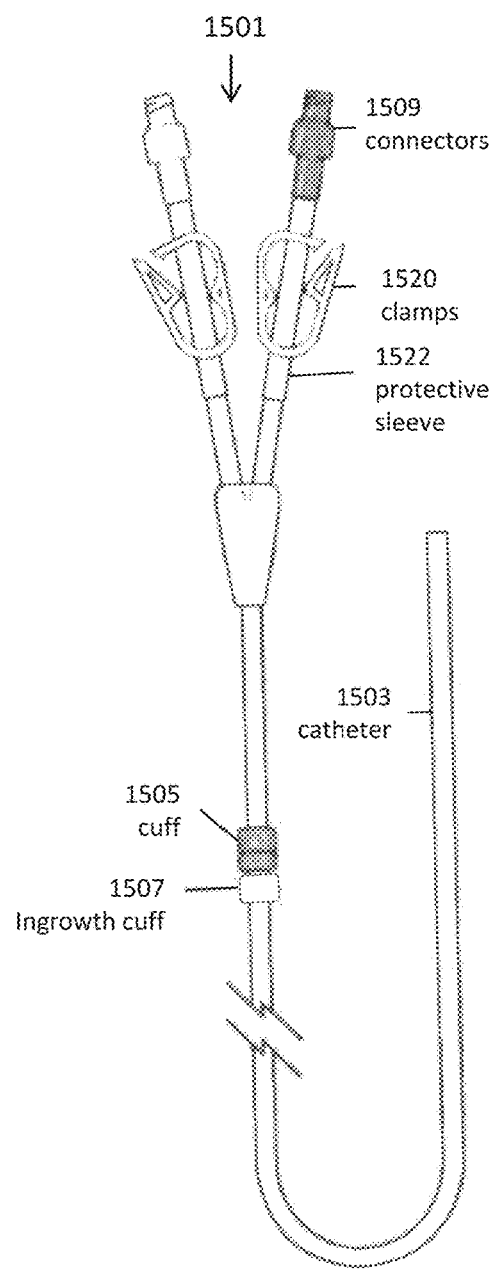

FIGS. 14A and 14B, as well as FIGS. 15A and 15B illustrate another variation of a type of device, a catheter such as a Venus catheter that may be partially or completely coated as described herein. The coatings described herein may benefit virtually any type of catheter; a Venus catheter is generally a tube inserted into a vein in the neck (as shown in FIG. 14A), chest, or leg, e.g., near the groin, usually only for short-term hemodialysis. In FIG. 14A, the tube splits in two after the tube exits the body. The two tubes have caps designed to connect to the line that carries blood to the dialyzer and the line that carries blood from the dialyzer back to the body. A person must close the clamps on each line when connecting and disconnecting the catheter from the tubes. Any portion (or the entire device) may be coated as described herein. For example, in FIGS. 14A and 14B, the outer surface of the catheter 1405 and/or the Venus and arterial lines may be coated as described herein.

In some devices, it may be helpful to provide a cuff or cuffs on the device that are specifically configured for the galvanic release of antimicrobial ions. For example, FIGS. 15A and 15B illustrate catheters 1500, 1501 for long-term vascular access that includes a cuff that may be at least partially coated as described herein for the release of antimicrobial ions. Adjacent to the ion-releasing cuff 1505 is a tissue-ingrowth cuff 1507.

In general, the wide use of invasive medical devices, including intravascular catheters has led to an increase in infections related to the use of the medical device. However, intravascular catheters are often associated with serious infectious complications, such as catheter-related bloodstream infection (CRBSI). In fact, CRBSI is considered to be the most common type of nosocomial bloodstream infection, a finding that has been attributed to the wide use of intravascular catheters in hospitalized patients. It is estimated that 7 million central venous catheters (CVCs) will be inserted annually in the United States. Even with the best available aseptic techniques being used during insertion and maintenance of the catheter, 1 of every 20 CVCs inserted will be associated with at least 1 episode of bloodstream infection.

In the early 2000's, an estimated 300,000 cases of catheter-related bloodstream infection (CRBSI) occurred in the United States each year. Existing interventions to control CRBSI include anticoagulant/antimicrobial lock, use of ionic silver at the insertion site, employment of an aseptic hub model, and antimicrobial impregnation of catheters. However, these solutions have not proven ideal.

Figure 16:
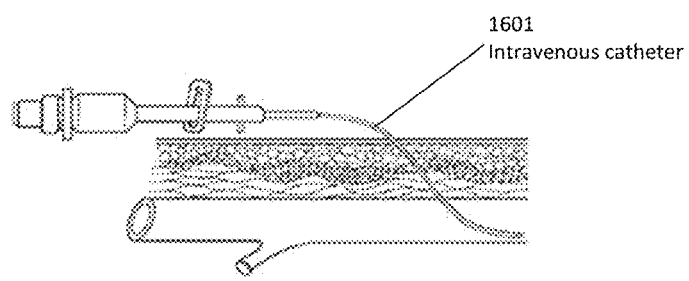
FIG. 16 shows one example of a catheter that has been coated by co-deposition of the galvanic coating described herein.

Several factors pertaining to the pathogenesis of CRBSI have been identified during the last decade. The skin and the hub are the most common sources of colonization of percutaneous vascular catheters. For short-term, nontunneled, noncuffed catheters, the organisms migrate from the skin insertion site along the intercutaneous segment, eventually reaching the intravascular segment or the tip. Thus, it may be beneficial to include the galvanic release coating(s) described herein along any (or all) portions of the catheters that are inserted into the patient, to allow galvanic release of the antimicrobial ions (e.g., silver, nickel, etc.) as described above. For example, FIG. 16 illustrates one variation of a catheter 1601 (shown as an intravascular catheter in this example) that has been coated along its length (or over a region) with a layer of the mixture of between about 25% to about 75% (e.g., 30% and 70%) by volume of an anodic metal, and between about 25% to about 75% (e.g., 30% to 70%) by volume of a cathodic metal co-deposited on an outer substrate surface to form a non-uniform mixture of the anodic and cathodic metals. The coating may comprise a plurality of microregions or microdomains of anodic metal in a matrix of cathodic metal or a plurality of microregions or microdomains of cathodic metal in a matrix of anodic metal. The anodic metal is galvanically released as antimicrobial ions when the apparatus is inserted into a subject's body.

Generally, long-term catheters (particularly those that are cuffed or surgically implanted, such as those illustrated in FIGS. 15A-15B), the hub is a major source of colonization of the catheter lumen, which ultimately leads to bloodstream infections through luminal colonization of the intravascular segment. Thus, in some variations the hub region may be coated as described herein.

In addition to the examples described above, other insertable or implantable device that may be coated as described herein may include implantable devices such as drug delivery devices (e.g., pumps), cardiac management devices (e.g., pacemakers), cochlear implants, analyte sensing devices, catheters, cannulas or the like. Essentially any medical device which experiences microbial colonization and/or biofilm formation and/or encrustation is appropriate for the practice of the present invention, including analyte sensing devices such as electrochemical glucose sensors, drug delivery devices such as insulin pumps, devices which augment hearing such as cochlear implants, urine contacting devices (for example, urethral stents, urinary catheters), blood contacting devices (including needles, blood bags, cardiovascular stents, venous access devices, valves, vascular grafts, hemodialysis and biliary stents), and body tissue and tissue fluid contacting devices (including biosensors, implants and artificial organs). Medical devices include but are not limited to permanent catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts, cerebral and spinal shunts, heart valves, heart assist devices (e.g., left ventricular assist devices), pacemaker capsules, incontinence devices, penile implants, small or temporary joint replacements, urinary dilator, cannulae, elastomers, hydrogels, surgical instruments, dental instruments, tubings, such as intravenous tubes, breathing tubes, dental water lines, dental drain tubes, and feeding tubes, fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field. Medical devices also include any device which may be inserted or implanted into a human being or other animal, or placed at the insertion or implantation site such as the skin near the insertion or implantation site, and which include at least one surface which is susceptible to colonization by biofilm embedded microorganisms. Medical devices also include any other surface which may be desired or necessary to prevent biofilm embedded microorganisms from growing or proliferating on at least one surface of the medical device, or to remove or clean biofilm embedded microorganisms from the at least one surface of the medical device, such as the surfaces of equipment in operating rooms, emergency rooms, hospital rooms, clinics, and bathrooms. Non-implanted devices for use in a medical procedure that may be coated as described herein include surgical tools, e.g., suturing devices, forceps, retractors, sponges, etc.

Orthopedic devices may in particular benefit from the coatings described herein. An implant as described herein may be used to treat bone and/or soft tissue. In some variations the implants are bone implants specifically, and may be configured to support as well as treat the bone. For example, the implant may be used to secure (as a screw, nail, bolt, clamp, etc.) another member such as a plate, rod, or the like, or the implant may itself include a support member such as a rod, plate, etc. In some variations, the implant is a soft tissue implant that is configured to be secured within non-bone body structures.

Figure 17A:
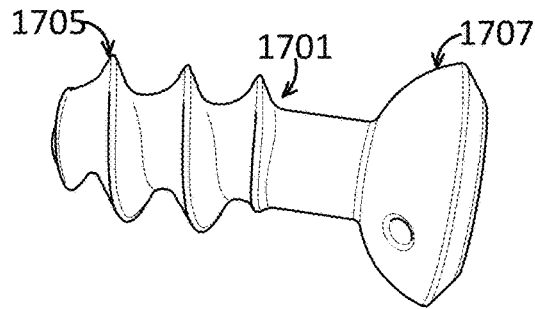
FIG. 17A shows a cannulated bone screw that may be used with a coated insert as shown in FIG. 17B. The coated insert may be a bioabsorbable mesh, coated as described herein.
Figure 17B:
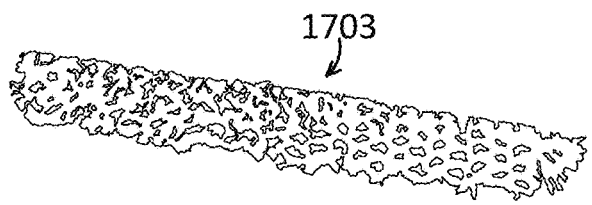
FIG. 17C shows the bone screw of FIG. 17A with the mesh of FIG. 17B inserted.
Figure 17C:
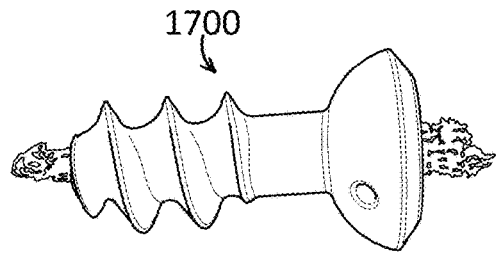

For example, FIGS. 17A-17C illustrate one variation of an apparatus for use in delivering an antimicrobial ion (e.g., silver ions) to a repair site to prevent or treat infection. In this example, apparatus includes a replaceable/removable insert that is coated. The insert maybe a mesh or other material having a relatively large surface to volume ratio (e.g., large surface area). For example, FIG. 17A shows a cannulated bone screw 1701, e.g., a bone screw having a central cannula region (not visible in FIG. 17A) into which another device or element may be inserted, such as the bioabsorbable material 1703 (mesh) shown in FIG. 17B. In FIG. 17A, the bone screw includes a distal threaded region 1705 and a more proximal head 1707. In FIG. 17B the bioabsorbable mesh 1703 is coated with the antimicrobial ion releasing coating such as described herein (e.g., 30% silver/70% platinum) to a thickness of 100 microinches. The cannulated bone screw 1701 may also be coated, or may not be coated. Either before or after inserting the bone screw into the body, the bioabsorbable insert 1703 may be inserted into the cannula of the bone screw 1701. This is illustrated in FIG. 17C. In practice, multiple inserts 1703 may be added to the bone screw device.

Figure 18A:
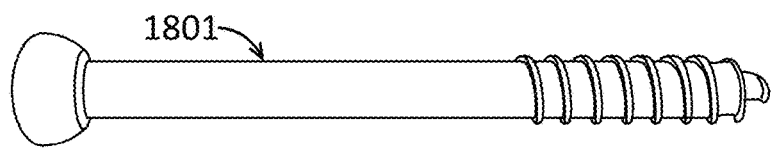
FIG. 18A shows a bone screw coated as described herein.
Figure 18B:
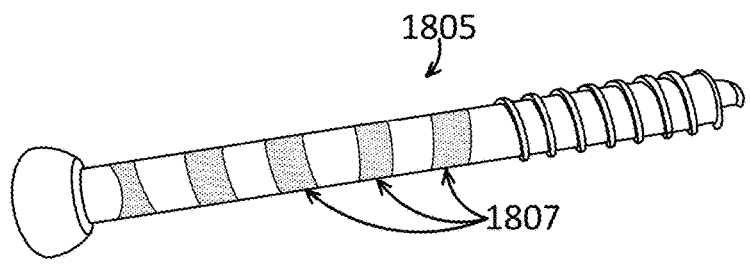
FIG. 18B shows a bone screw similar to that shown in FIG. 18A, but which has been coated in a striped pattern (e.g., having regions that are either uncoated, or coated with different anionic materials/combinations of materials, as described in FIGS. 3A-3C, above.

In some variations, the bone screw may itself be coated, without the use of an additional element (e.g., a bioabsorbable insert). FIGS. 18A and 18B illustrate different variations of implants (e.g., bone screw) that include antimicrobial ion releasing coatings as described herein. In FIG. 18A, the entire bone screw 1801 is coated with an antimicrobial ion releasing coating comprising a mixture of between about 25% to 75% (e.g., 30% and 70%) by volume of an anodic metal, and between about 25% to 75% (e.g., 30% to 70%) by volume of a cathodic metal co-deposited on the outer substrate surface to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming a continuous path of interconnected veins of anodic metal through the coating thickness, or a continuous path of interconnected veins of cathodic metal through the coating thickness, wherein the continuous path extends from an outer surface of the coating to the substrate to the opposite side of the coating (which may be adjacent to the substrate). In FIG. 18B, the bone screw apparatus is a screw that has not been completely coated, but includes differently coated regions, or regions that are both coated and uncoated. In this example the substrate is the surface of a bone screw having a striated pattern of regions of coatings alternating with uncoated regions.

FIGS. 19A-19B illustrate another variation in which the implant is configured as an orthopedic device (e.g., bone screw) having extendable members that can be extended out of the body of the bone screw to project into the tissue and allow release of antimicrobial ions into the surrounding tissue. In this variation, the implant 1901 is configured as a bone screw that is hollow or contains a hollow inner body region (not visible in FIG. 19A) into which a replaceable/rechargeable treatment cartridge may be inserted and/or removed. The cartridge may be itself screwed into the body, or it may be otherwise secured within the body. The cartridge may include one or more (e.g., a plurality) of ion release members 1909 extending or extendable from the cartridge and therefore the implant. The ion release member(s) may be configured to release silver, zinc or silver and zinc and may be coated with any of the coatings described herein. In general, an ion release member may be configured as an elongate member such as an arm, wire, branch, or the like. The ion release member may be a coated member such as a Nitinol or other shape-memory member coated with an antimicrobial ion releasing coating comprising a mixture of between about 25% to about 75% (e.g., 30% and 70%) by volume of an anodic metal (e.g., silver), and between about 25% to about 75% (e.g., 30% to 70%) by volume of a cathodic metal (e.g., platinum) co-deposited on the outer substrate surface to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming a continuous path of interconnected veins of anodic metal through the coating thickness, or a continuous path of interconnected veins of cathodic metal through the coating thickness, wherein the continuous path extends from an outer surface of the coating to the substrate to the opposite side of the coating (which may be adjacent to the substrate). As mentioned, the implant (or the treatment cartridge portion) may include a plurality of ion release members.

These implants may have one or more exit channels 1905. In general the exit channels may be openings from the inner hollow region (e.g. cannulated body) of the implant through a side wall of the implant and out, possibly in the threaded region 1907. Thus, in FIGS. 19A and 19B, the exit channel is configured to deflect the one or more ion release members away from a long axis of the implant. For example, the exit channel may be configured to deflect the one or more ion release members against a thread of the outer threaded region so that it deflects away from the implant. In some variations a plurality of exit channels extending through the cannulated body 1903.

An implant such as the one shown in FIGS. 19A-19B may also include a guide (or guide element, including a rail, keying, etc.) within the channel configured to guide or direct the one or more ion release member out of the cannulated body 1903 from the at least one exit channel 1905. The exit channels may be configured to allow tissue (e.g., bone) ingrowth, which may help with stability of the device once implanted. For example, the exit channels may be slightly oversized compared to the ion release members, permitting or encouraging in-growth. In some variations the exit channels may be doped or otherwise include a tissue-growth enhancing or encouraging factor (such as a growth factor), or may be otherwise modified to encourage tissue growth.

A treatment cartridge may be replaceable. For example, a treatment cartridge may be configured to be removable from the cannulated body of the implant in situ, without removing the body of the implant from the device. Thus, the body of the implant may be structurally supportive (e.g., supporting the bone) while the silver-releasing cartridge arms may be re-charged by inserting another (replacement) cartridge after the previous cartridge has corroded. For example, an elongate cannulated body 1903 may be configured as bone screw (e.g., an intramedullary bone screw).

In addition, the antimicrobial coatings described herein may also be effective for use in non-implantable and/or insertable devices. As mentioned above, any apparatus that may come into contact with a conductive (e.g., electrolytic) fluid, such as bodily fluids, may benefited from the antimicrobial coatings described herein; such apparatuses are not limited to medical devices and systems.

For example, also descried herein are garments (e.g., gloves, masks, scrubs), including facial masks (surgical masks, filters, or the like), sporting equipment (e.g., facemasks, mouthpieces, helmets, etc.), shoes (sole/shoe inserts, etc.), jewelry (necklaces, bracelets, rings, etc.) and the like, that may be coated or may include a coated region, wherein the coating comprises any of the antimicrobial ion releasing coatings described herein, such as a coating comprising a mixture of between about 25% to about 75% (e.g., 30% and 70%) by volume of an anodic metal (e.g., silver), and between about 25% to about 75% (e.g., 30% to 70%) by volume of a cathodic metal (e.g., platinum) co-deposited on the outer substrate surface to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming a continuous path of interconnected veins of anodic metal through the coating thickness, or a continuous path of interconnected veins of cathodic metal through the coating thickness, wherein the continuous path extends from an outer surface of the coating to the substrate to the opposite side of the coating (which may be adjacent to the substrate).

FIG. 20 is one example of a non-medical application of a coating as described herein. For example, an animal cage 2005 may be coated (particularly on the bottom region) with any of the antimicrobial coatings described herein. In this example, the cage may include an antimicrobial ion releasing coatings as described herein, such as a coating comprising a mixture of between about 25% to about 75% (e.g., 30% and 70%) by volume of an anodic metal (e.g., silver), and between about 25% to about 75% (e.g., 30% to 70%) by volume of a cathodic metal (e.g., platinum) co-deposited on the outer substrate surface to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming a continuous path of interconnected veins of anodic metal through the coating thickness, or a continuous path of interconnected veins of cathodic metal through the coating thickness, wherein the continuous path extends from an outer surface of the coating to the substrate to the opposite side of the coating (which may be adjacent to the substrate).

Similarly, any household apparatus that may be exposed to a bodily fluid (including sweat and/or mucus, as from sneezing or coughing) may be coated with any of the coatings described herein, to act as an effective antimicrobial barrier. For example, FIG. 21 illustrates a doorknob 2101 that may be partially or completely coated with any of the antimicrobial ion releasing coatings described herein on a portion that will be held by an operator's hand 2109. Thus, this region may be coated with a coating comprising an antimicrobial ion releasing coating such as a coating comprising a mixture of between about 25% to about 75% (e.g., 30% and 70%) by volume of an anodic metal (e.g., silver), and between about 25% to about 75% (e.g., 30% to 70%) by volume of a cathodic metal (e.g., platinum) co-deposited on the outer substrate surface to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming a continuous path of interconnected veins of anodic metal through the coating thickness, or a continuous path of interconnected veins of cathodic metal through the coating thickness, wherein the continuous path extends from an outer surface of the coating to the substrate to the opposite side of the coating (which may be adjacent to the substrate). Other household fixtures that may be readily coated include light switches, door handles/pulls, kitchen appliances (and particularly handles/controls for kitchen appliances), tabletop and/or countertop surfaces, and bathroom surfaces. For example, a toilet handle, toilet (including toilet seat and/or bowl), sink, and/or faucet may be coated as described herein.

In addition, cookware, dining wear, and/or cutlery may be coated. Such coatings are safe, and non-toxic, though still antimicrobial, and may be extremely long lasting (e.g., extending over months or years, depending on coating thicknesses and use). Further, these coatings do not degrade or lose their antimicrobial activity, which is dependent primarily or exclusively on the galvanic release of ions (e.g., silver ions). For example, as shown in FIGS. 22A-22B, cutlery (e.g., spoons 2205, forks 2207, etc.) may be coated as described herein, particularly on the portions to be placed in a user's mouth. FIG. 22B shows an example of an infant spoon 2205' having an elongate handle and end region 2230 forming the spoon that is to be placed in an infant's mouth; this end region 2230 may be coated specifically, e.g., with an antimicrobial ion releasing coating as described herein, such as a coating comprising a mixture of between about 25% to about 75% (e.g., 30% and 70%) by volume of an anodic metal (e.g., silver), and between about 25% to about 75% (e.g., 30% to 70%) by volume of a cathodic metal (e.g., platinum) co-deposited on the outer substrate surface to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming a continuous path of interconnected veins of anodic metal through the coating thickness, or a continuous path of interconnected veins of cathodic metal through the coating thickness, wherein the continuous path extends from an outer surface of the coating to the substrate to the opposite side of the coating (which may be adjacent to the substrate). The substrate may be stainless steel, polymer, or any other appropriate material. The coating is both washable and sterilizable without losing efficacy.

In some variations, the substrate is a particle, such as a micro (or nano) particle that is coated as described herein, to form a powder or other material that may be added to a device or system to provide antimicrobial activity. For example, polymeric particles may be coated (or a polymeric material may be coated and ground/broken up into smaller particles) with any of the antimicrobial ion releasing coatings described herein, such as a coating comprising a mixture of between about 25% to about 75% (e.g., 30% and 70%) by volume of an anodic metal (e.g., silver), and between about 25% to about 75% (e.g., 30% to 70%) by volume of a cathodic metal (e.g., platinum) co-deposited on the outer substrate surface to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming a continuous path of interconnected veins of anodic metal through the coating thickness, or a continuous path of interconnected veins of cathodic metal through the coating thickness, wherein the continuous path extends from an outer surface of the coating to the substrate to the opposite side of the coating (which may be adjacent to the substrate). The resulting particles (which may be referred to as an antimicrobial powder) may be added, e.g., into structures or onto surfaces that will come into contact with bodily fluids.

Surface Treatments

As mentioned above, the antimicrobial coatings described herein may be applied directly to any appropriate substrate; the substrate may, in some variations, form a part of another device or system that comes into contact with a bodily fluid and therefore benefits from the use of these antimicrobial coatings. For example, a coating may be made directly onto the substrate, or it may be made onto another coating (e.g., a primer coating) which may be made to prepare the substrate for the coating. Examples of primer coatings are adhesion coatings, which may include a titanium and/or tantalum undercoating, as described above.

In some variations, the material is pretreated to prepare the surface to receive the coating. For example, in some metals (e.g., nickel titanium, stainless steel, etc.) the surface may oxidize naturally, and it may be beneficial to remove this oxide layer prior to applying the antimicrobial coatings described herein. For example, a substrate may be prepared by removing an oxide layer (or for other reasons) by vacuum blast cleaning with a noble gas such as argon (e.g., argon blasting or argon blast cleaning under a vacuum). Removing the thin outer oxide layer may enhance adhesion of the coating. In general, vacuum cleaning may be helpful, and may be performed immediately before applying the coating (e.g., co-sputtering the anodic and cathodic materials).

Other useful pre-treatments may include applying an undercoating layer (e.g., of platinum, parylene, etc.). Such undercoatings may be applied first (e.g., by sputter deposition, etc.).

One additional benefit of the coatings described herein is that they may be applied in a relatively cool application process, e.g., in which the temperature at which the co-deposition of the anodic material and cathodic material is applies is relatively cool (e.g., less than 150° C., less than 120° C., less than 100° C., less than 90° C., less than 80° C., less than 70° C., less than 60° C., less than 50° C., etc.). The temperature of application may be adjusted along with the time to form the coating (e.g., cooler application may generally take longer). Cooler application may be particularly beneficial when the substrates to which it is being applied is temperature sensitive, or when it is being applied to a device (including devices having active/electronic parts) that are rate below a predetermined temperature.

Post-Coating Treatments

Any of the apparatuses described herein (e.g., any of the coatings described herein) maybe treated to enhance the galvanic release of antimicrobial ions (e.g., silver). Such treatments may be referred to as post-coating treatments because they may be performed after the coating has been applied. For example, any of the apparatuses described herein may include coatings that are treated to enhance the surface area by cracking, fracturing, or otherwise roughening the coating, which may increase the exposed surface area of the coating.

Post-coating treatments may include thermal treatments (e.g., exposing the surface to a cooler temperature to crack or fracture the coating), and/or energy (e.g., ultrasound, RF, etc.) to fracture the surface. For example, in some variations the coating may be connected to an oscillating high voltage source that makes cracks in the coating. For example, FIGS. 23A and 23B illustrates a variation of a substrate 2320 (similar to the example shown in FIGS. 2A-2D) has been coated with an antimicrobial ion releasing coating 2300 as described above. In this example, after co-depositing the anodic and cathodic metals, the coated apparatus has been treated to fracture the coating, forming breaks/fractures 2350 (shown schematically in FIG. 23B from the enlarged region B in FIG. 23A). In this example, the fractures 2350 are formed vertically into the coating to expose more of the anodic metal and cathodic metal, potentially allowing for greater (and/or faster) release of anodic antimicrobial ions.

Thus, in any of the apparatuses described herein, the coatings may be fractured (cracked, etc.) to enlarge the surface area. Cracks or fractures may be formed of a predetermined density and/or depth. For example, the coating may be fractured or may include cleavage regions into the thickness of the coating at a density of between 0.01% and 80% of the surface (e.g., greater than 0.1%, greater than 1%, greater than 5%, greater than 10%, greater than 15%, etc.). The percentage of fracturing typically results in an increase the in the surface area, and may therefore be referred to as a percentage increase in the surface area. For example the percent increase in the surface area due to fracturing the surface may result in an increase of greater than 0.25 times the un-fractured surface area (e.g., a 25% or greater surface area following fracturing). In some variations the surface area may be increased greater than 0.3 times (e.g., 0.35× or greater, 0.40× or greater, 0.45× or greater, 0.5× or greater, 0.6× or greater, 0.75× or greater, 0.8× or greater, 0.9× or greater, 1× or greater, 2× or greater, 3× or greater, etc.).

Figure 25A:
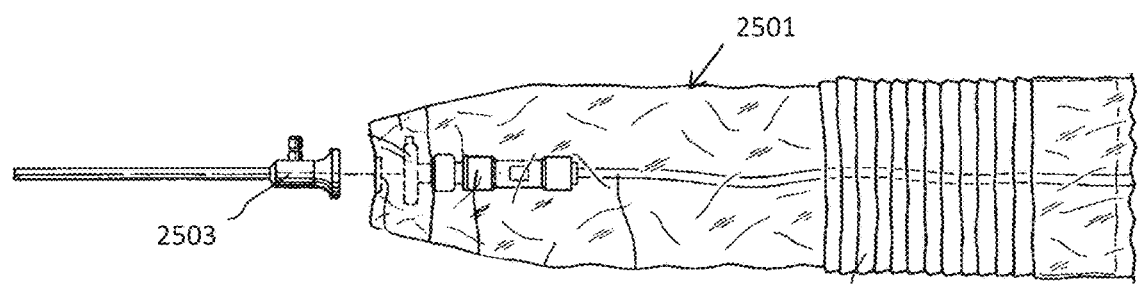
FIGS. 25A and 25B illustrate an example of a surgical drape including an antimicrobial coating as described herein, configured as a drape for a surgical instrument.
Figure 25B:
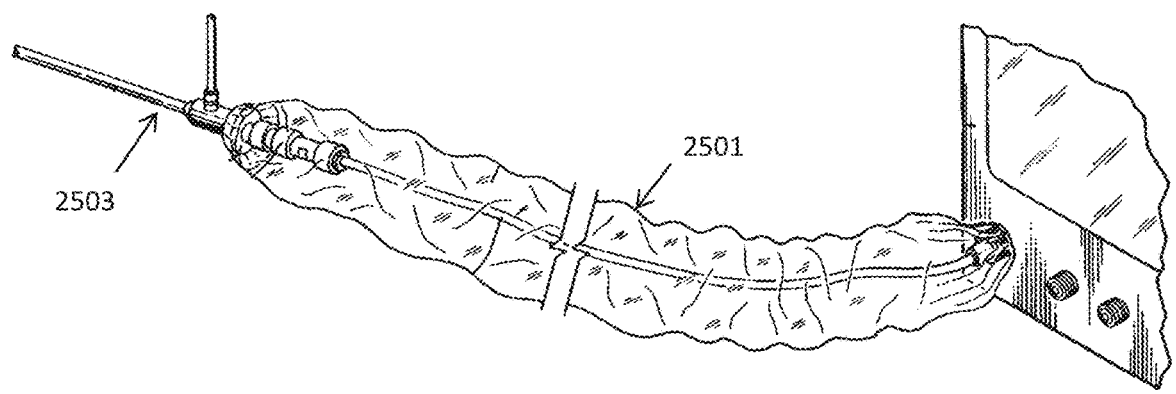

As mentioned above, in general, the antimicrobial coatings described herein may be included on any appropriate surface, including medical devices (e.g., implants, surgical tools, medical clothing, gloves, surgical drapes, covers, etc.), and the like. For example, FIGS. 25A-25B illustrate an endoscope 2503 having a protective (sterile) drape 2501 that may be used as part of a surgical procedure to maintain a sterile field. In FIGS. 25A and 25B, the drape 2501 may be coated completely or partially on a surface (e.g., outer surface) with any of the coatings as described herein. For example, the flexible drape outer surface may be coated with a coating comprising a mixture of between about 25% to about 75% (e.g., 30% and 70%) by volume of an anodic metal (e.g., silver), and between about 25% to about 75% (e.g., 30% to 70%) by volume of a cathodic metal (e.g., platinum) co-deposited on the outer surface of the drape to form a non-uniform mixture of the anodic and cathodic metals, wherein the coating comprises a plurality of microregions or microdomains of anodic metal in a matrix of cathodic metal or a plurality of microregions or microdomains of cathodic metal in a matrix of anodic metal, the microregions or microdomains forming a path of interconnected veins of anodic metal through the coating thickness, or a path of interconnected veins of cathodic metal through the coating thickness, wherein the continuous path extends from an outer surface of the coating to the substrate to the opposite side of the coating (which may be adjacent to the outer surface of the drape). The outer surface of the drape (the substrate) may be prepared for the coating by using a priming coating (e.g., of titanium or other undercoating, etc.). The coating may be applied in a pattern (e.g., mesh pattern) which may preserve flexibility of the substrate.

Figure 26:
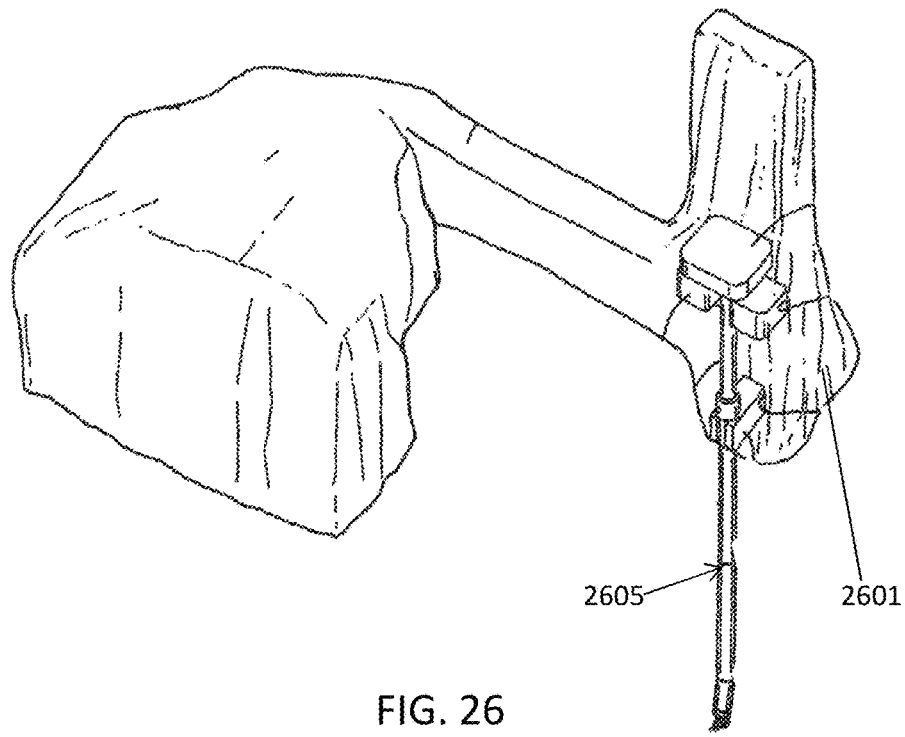
FIG. 26 shows an example of a drape for use in a sterile medical field that has been coated with the antimicrobial coating as described herein; in this example the drape covers a robotic medical device.
Figure 27:
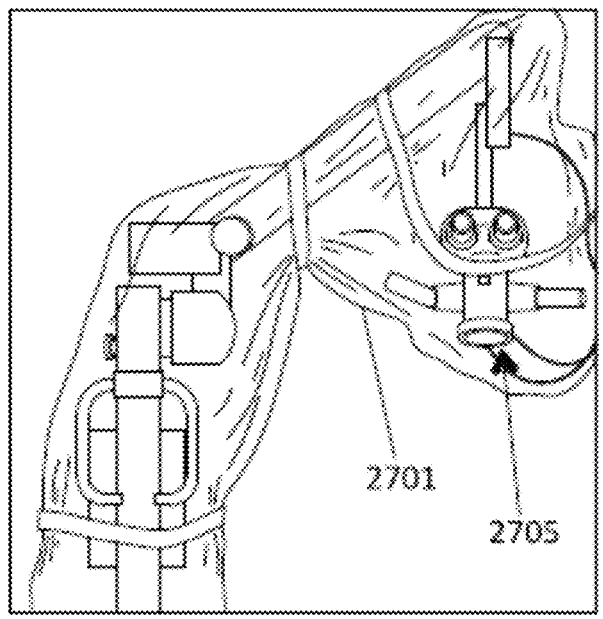
FIG. 27 shows a medical microscope covered with a drape or cover coating as described herein.
Figure 28:
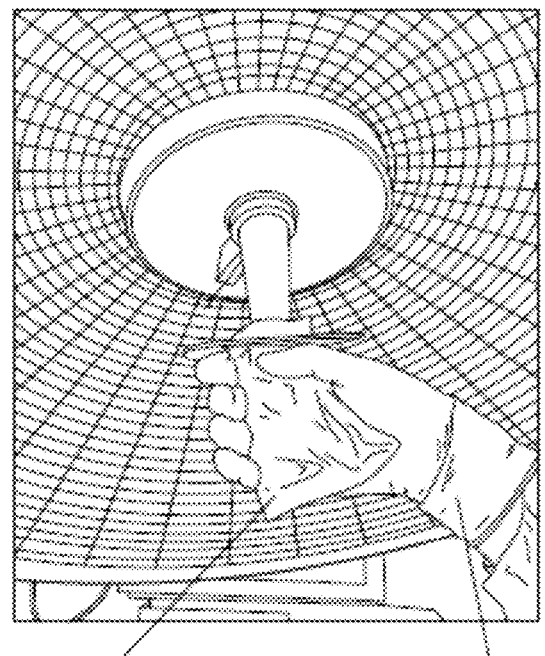
FIG. 28 is an example of a cover/handle for a surgical light that has been coated as described herein.

In general, any cover, clothing or draping (e.g., surgical draping) may include any of the antimicrobial coatings described herein. For example, any of the apparatuses shown and described in FIGS. 26-31 may be coated with an antimicrobial coating as discussed above. FIG. 26 shows one example of a surgical (sterile) draping 2601 that may be used to preserve a surgical sterile field when using a robotic and/or mechanical surgical tool 2605. FIG. 27 shows another example of a cover (or drape) 2701 for a surgical tool; in FIG. 27 the tool is a surgical microscope 2705. An outer surface (the entire outer surface or a region thereof) may be coated with any of the antimicrobial coatings described herein. FIG. 28 illustrates another example of a cover for use in a sterile operating field; in this example the sterile handle 2801 may be coated; alternatively or additionally, the glove 2809 may be coated or include a coating.

Figure 29:
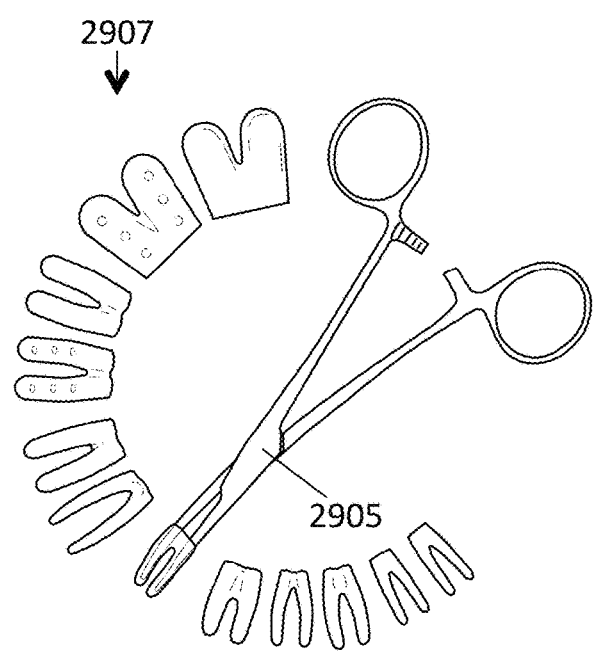
FIG. 29 illustrates an example of a surgical instrument cover including a coating as described herein.
Figure 30A:
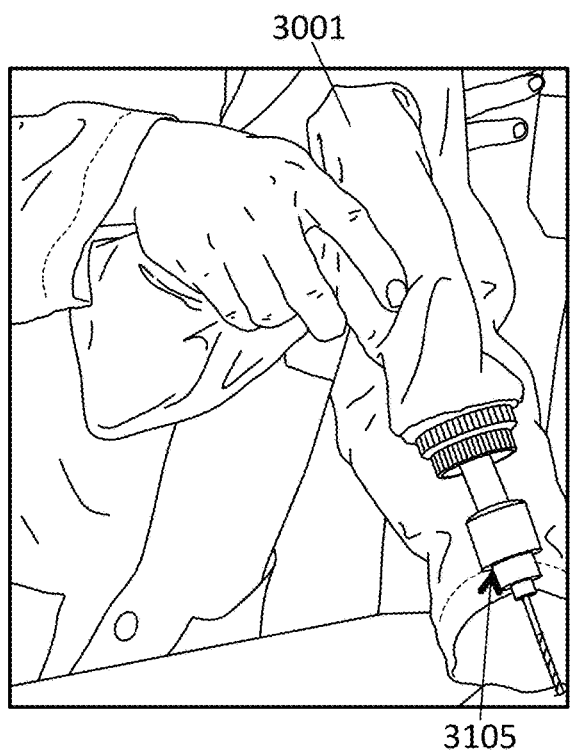
FIGS. 30A and 30B show examples of surgical instrument covers (shown as surgical drills in this example) that may be coated with any of the antimicrobial coatings described herein.
Figure 30B:
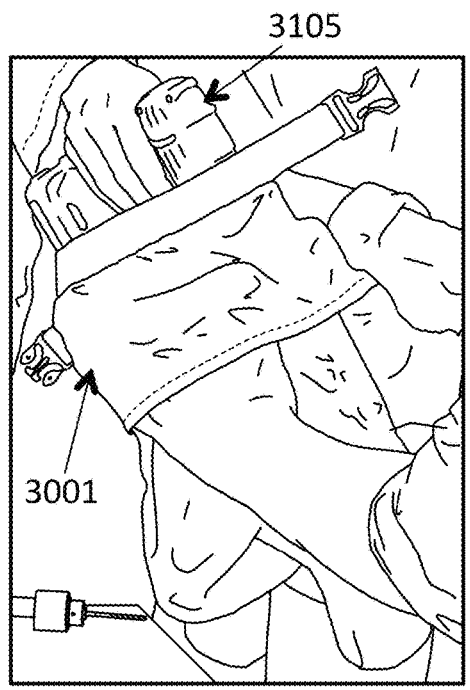
Figure 31:
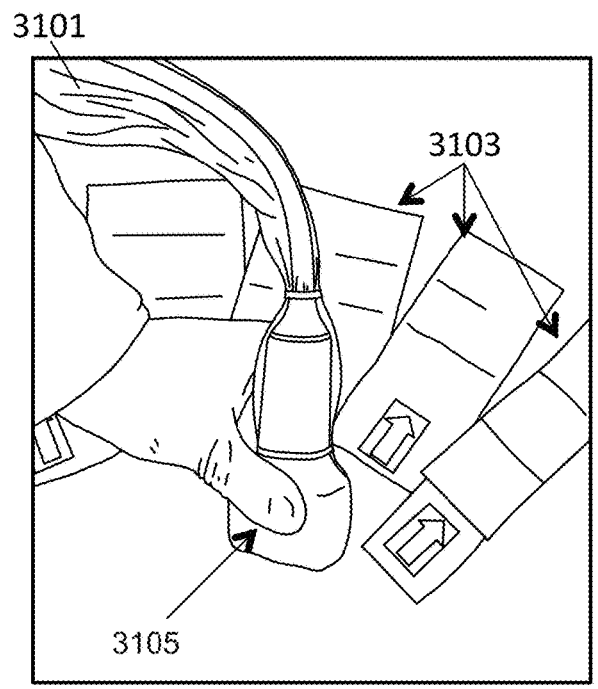
FIG. 31 is an example of a cover for an ultrasound probe that has been coated as described herein.

FIG. 29 illustrates a medical device (e.g., forceps 2905) having covers 2907 that may also be coated as described herein. Either the inside, outside or both inside and outside of the covers may be coated. FIGS. 30A-30B illustrate covers 3001 for medical tools (show as drills 3005) that may be sterile, and may also be coated with any of the antimicrobial coatings described herein. FIG. 31 shows an ultrasound prove 3105 that is covered with a sterile cover 3101 that may include a coating as described above. Additional covers 3103 are shown in FIG. 31, as the single cover may be single-use.

In use, as described above, a draping or cover such as the endoscope covers shown in FIGS. 25A-25B or the surgical drapes or covers shown in FIGS. 26, 27, 28, 29, 30A-30B and 31 may release antimicrobial ions to form an antimicrobial field when contacted with a bodily fluid. In particular, during a surgical procedure, contact with blood, mucus, lymph, vomit, or the like onto the coated surface(s) may initiate the galvanic release of antimicrobial ions (e.g., silver) from the coating, as described herein. Similarly, contacting any of these coated surfaces by hand may initiate galvanic release, as a bare hand typically has sufficient surface moisture, sweat, oils, etc. to initiate galvanic release.

Bone Screws

In some variations, the ion-releasing implants described herein are configured as bone screws for treating a bone in need of treatment, such as a broken or osteoporotic bone. The ions released may be silver, zinc, or silver and zinc. Methods for treating a tissue (including bone) are also described herein. For example, an implant may be configured as a bone screw may align, biopsy, fuse, and/or stabilize a bone. The screw may eliminate, prevent, or reduce an infection, such as a bacterial, protozoan, or fungal infection. The treatment from the screw may provide support to the bone and may generate therapeutic silver ions to eliminate, prevent or reduce an infection.

In general, when two metals with different redox potentials are in electrical contact and immersed in an electrolyte, one metal may preferentially ionize and free electrons. As the free electrons migrate to the second metal, an electrical potential, called a galvanic potential, is created. The process requires an electron acceptor, such as oxygen near the second metal. When the first metal is silver, ionic silver is released. Similarly, if the first metal is zinc, ionic zinc is released.

The devices and systems described herein are controllable ion-releasing systems that are configured to allow the controllable release of ions (and particularly silver and/or zinc ions) into a body with sufficient concentration and distribution to prevent or treat infection in the tissue while also providing structural support to the region and preventing migration of the device. Various embodiments of these devices are described and illustrated, however the general theory of operation of all of these devices may be similar. The devices or systems may be configured as bone implants that treat bone and surrounding tissue, by release of ions such as silver ions.

As described above, FIGS. 1A-F describe a simple galvanic cell setup such as for use in a body. The setup is shown treating an infection, but the same process could be applied to healthy tissue to prevent an infection (prophylactically). The components including a first metal 2 (e.g., silver), second metal 4 (e.g., platinum), and electrolytic fluid 6 (e.g., blood) are shown individually in FIGS. 1A-1C and arranged in a tissue in FIGS. 1D-1F. Electrolytic body fluid 6 is shown bathing or contacting healthy tissue 10 as well as infected tissue 8. When silver metal 2 contacts platinum metal 4 in body fluid 6, it forms a galvanic cell with a silver anode and platinum cathode. As shown in FIG. 1E, ionic silver 12 is generated and spreads through the body fluid, killing microorganisms and creating an infection-free zone 14 in body fluid 16 in the vicinity of the anode. After treatment is complete, silver anode 2 may be removed 20 leaving an infection-free body fluid 18. Alternatively, platinum cathode 4 may be removed; alternatively both anode 2 and cathode 4 may be removed. Although the system is described using a silver metal anode and a platinum metal cathode, any metal with a higher redox potential than silver may be used as the cathode. The metal may be a noble metal, such as gold, palladium or platinum. For purposes of illustration, the silver anode will be described as the removable trigger for creating and stopping the galvanic response. However, either the silver or the metal with the higher redox potential can serve as a removable trigger (cartridge).

One embodiment of a device for controllably releasing silver is a bone stabilization device such, such as a bone screw. A bone stabilization device may include a support region (e.g., an elongate rod, tube, channel, or the like) for insertion into the bone, and an insertion engagement region (e.g., a head, shoulder, coupling, etc.) for engaging with an insertion and or removal tool. The insertion engagement region may be located at or near the proximal end, and may include an opening or engagement region for insertion and/or activation of a silver-release (e.g., galvanic silver release) cartridge. In some variations the engagement region includes a deployment mechanism (or contains a deployment mechanism) for activating and/or deploying silver-releasing members of a silver-releasing cartridge. The deployment mechanism may be referred to as a deployment trigger. Examples of this are provided below.

For example, a stabilization device for controllable release of silver may be configured as a silver-releasing bone screw. In general a silver-releasing bone screw is configured to controllably and/or activatably release silver to prevent and/or treat infection. A bone screw may include an elongate body (which may be threaded or otherwise include one or more bone engagement surfaces) and an engagement region at the proximal end configured as a head; one or more cartridges for galvanic release may also be included to allow the device to galvanically release silver. For example, a bone screw according to the disclosure may have a screw rod (elongate body) and one or more cartridges. The cartridge(s) may be configured to insert into the screw rod, and may be configured as an anti-infective cartridge or a biopsy cartridge or both. A bone screw may have a platinum metal cathode and a silver metal anode. In some variations the cathode and/or the anode (or just one or the other) may be present on the body of the bone screw; in other variations the cathode and/or anode (or both) may be present on a cartridge that can be inserted and/or removed from the bone screw. In some variations, the screw rod may be a platinum metal cathode and the anti-infective cartridge may be a silver metal anode. The cartridges may also include one or more anchoring, engagement, and/or stabilization members that are configured to extend from the bone screw and into the bone. These members may be configured as arms, fingers, spikes, ribs, probes, struts, or the like, and may extend from the body of the bone screw and into the tissue (including into the bone).

For example, in some variations, the screw rod is an elongated, cannulated (hollow), threaded rod. The rod may be externally threaded and/or internally threaded. Internal threads (or other guides/engagement regions) may be used to position and/or secure a cartridge within the body. The screw rod may be sized and elongated to fit a specific type of bone. The screw can fit any type of bone. By way of example, the screw can be configured to fit a femur, metatarsal, tarsal, tibia, or vertebra. Threads on the outer surface of the screw rod may anchor the screw rod into a bone or other body part. Thus, as mentioned, it may be threaded or may include other externally-facing engagement regions. The screw rod may be cannulated along its entire length, or along part of its length. The cannulated portion may create a fluid flow path. Fluid, such as oxygen carrying blood, may flow along the flow path and provide oxygen to create galvanic silver ion generation by the screw. In one example, the screw rod may be cannulated from a proximal end to part but not all of the way to a distal end. The screw rod may be solid along part of its distal end. The solid distal end may be used to deflect a portion (e.g., anchoring, engagement, and/or stabilization members) of a cartridge to be deflected from the cannulated inside to outside the screw rod, and may also provide additional stability and/or strength to the elongate body.

Figure 32A:
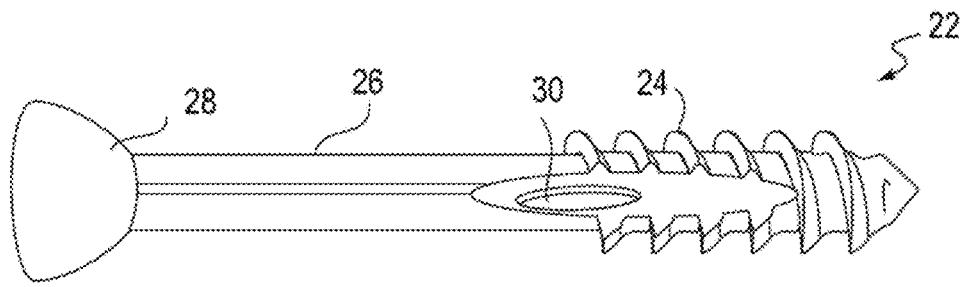
FIGS. 32A and 32B illustrate one variation of an implant as described herein.

FIG. 32A shows one variation of a bone stabilization implant for delivering an antibiotic (e.g., silver) in a controllable manner to a region of bone and/or surrounding tissue. In this example the bone stabilization device is configured as a bone anchor screw including an elongated, cannulated screw rod 22 region. Screw rod 22 has elongated body 26 and threads 24. Threads 24 are configured to penetrate a part of a bone and/or to hold the screw in place in a bone or body region.

The screw may have a screw head 28 at a proximal end with one or more features to aid in holding, placing and/or removing the screw rod and for inserting and/or activating the cartridge. FIG. 32A shows one example of a screw head configured as a grippable screw head 28. The screw head may engage an insertion device and/or removal device. In some variations the screw may have a shaped head, such as hexagonal head 56 shown in FIGS. 35 and 36 that can be gripped by a wrench or other gripping tool. The feature may also be used to hold the rod screw in place while inserting or removing a cartridge or performing other manipulations.

The inside of the screw rod may have connection means for connecting with or attaching an insertion tool. In one example, the screw rod may have threads inside the screw rod (internal threads). The internal threads may be along part or maybe along the entire internal length of the screw rod.

The bone screw example shown in FIG. 32A includes a screw rod with a channel or opening 30. The screw rod may have just one channel or opening or may have more than one channel or opening. The channels or openings may be sized and shaped to allow at least part of a biopsy cartridge and/or anti-infective cartridge to move outside cannulated screw rod.

The shape and pitch of the screw rod external threads may be angled or shaped to aid or direct cartridge placement. FIG. 32A shows screw rod external threads 24 that may aid placement of a cartridge. The cannulated screw rod may have a port or ports (e.g., an opening) around the channel that is configured to guide a portion of a biopsy element and/or anti-migration/anti-infection element of a cartridge from inside the cannulated screw rod to outside.

The screw rod may be made of any biocompatible material that is sufficiently strong to be inserted into a body (bone) region. For example, the screw may be made, at least in part, of a steel (e.g., stainless steel), or other material. In some variations, the screw rod is made of platinum, titanium, or stainless steel material that is coated with platinum, palladium or gold. In particular, the screw rod may be coated with a material or materials that are able to create a galvanic response with silver. The coating may be over the entire surface of the screw rod or may be over part of the surface. The coating may be in the form of bands. The coating material may be a noble metal that has a greater galvanic potential than silver in a body. The noble metal may be gold, palladium, or platinum.

The rod screw may have features to increase its surface area. In particular, in variations in which the anode or, more likely, the cathode is located on the surface of the screw body, the portion of the screw body forming the cathode may have a relatively large surface area (particularly as compared to the opposite redox partner, e.g., anode). A larger surface area may create a higher galvanic current for generating therapeutic silver ions. The rod screw may comprise foamed metal on its inside surface, outside surface, or both surfaces.

Figure 35:
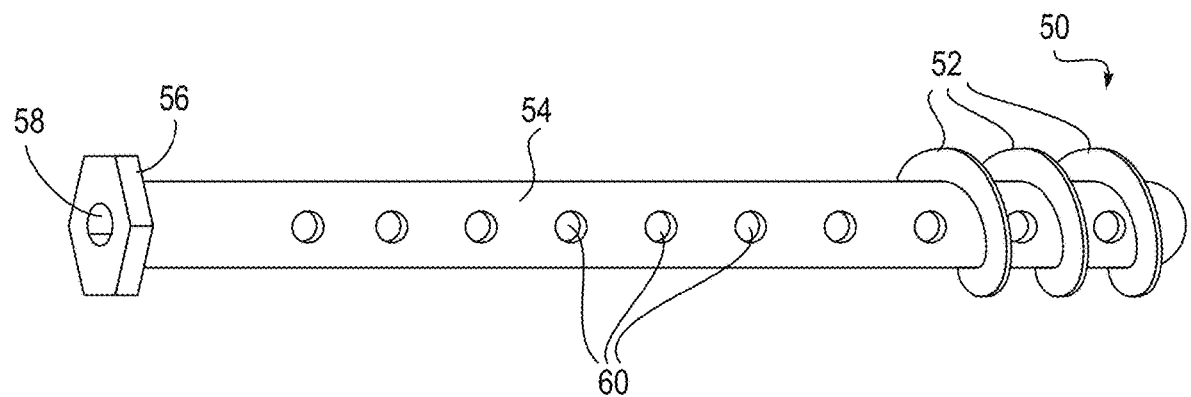
FIG. 35 is another variation of an implant.
Figure 36:
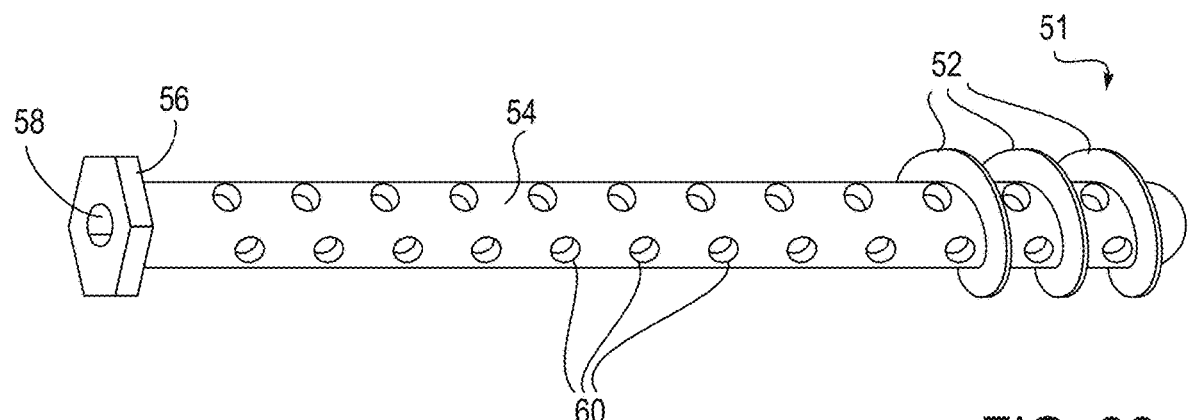
FIG. 36 is another variation of an implant.

In some variations the screw or rod configured as a stabilization device with controllable silver release may include on ore more features to increase opportunities for contact with body fluid. Increased contact may allow a stronger, faster, or longer galvanic response. FIGS. 35 and 36 show examples of rod screws 50, 51 with openings 60 along body 54 in addition to openings near threads 51. These openings may allow increased fluid flow, such as blood flow, around and through the rod screw. Some or all of these opening may also be configured to allow exit of one or more members (e.g., arms, struts, etc.) from a cartridge.

Any of the devices described herein may include or be configured for use with one or more cartridges. In general, a cartridge is a removable/replaceable element that may be inserted into or alongside of these support and antimicrobial devices (e.g., screws). As mentioned above, the cartridge may include one or more members that are configured to be extended out of the device and into the surrounding tissue. These members may be referred to and configured as struts, probes, legs, arms, hooks, wires, coils, fingers, spikes, ribs, or the like; in general they are elongate members that may be inserted into the patient's tissue and extend away from the body of the device. The members may therefore be configured to help secure the device within the tissue. For example, the members may enhance the mechanical attributes of the device, including preventing the device from pulling out of the tissue.

A cartridge may be referred to as an anti-infection cartridge if it is configured to aid in the release of silver ions from the device. For example the cartridge may include one or more members having silver (e.g., anode) regions or configured so that an entire member is silver releasing. In some variations the cartridge may also be referred to as a biopsy cartridge that is configured to remove tissue (e.g., bone, soft tissue, etc.) for testing. In some variations the cartridge may be configured as both an anti-infection and a biopsy cartridge.

An anti-infection cartridge may include a cathode. For example, the cartridge may include a plurality of arms, some of which are formed of a metal such as platinum that can react with the silver anode to release silver. As mentioned, in some variations the body of the implant device may include all or portion of the cathode.

In the examples illustrated herein the treatment cartridges are shown as separate elements that may be inserted into the devices. For example, a cartridge may be inserted into the device after the device (e.g., screw body) has been implanted into the bone. Cartridges may be replaced or recharged (e.g., replacing a portion of a cartridge such as a silver-containing member) without removing the entire device from the patient.

In some variations the cartridge is integral with (or part of) the implant device (e.g., screw).

The anti-infection cartridge may serve other functions in addition to or instead of being anti-infective. For example, it may be configured to prevent device migration. In some variations, including those illustrated below, a plurality of member extend from the device body (e.g., the body of the bone screw) and push into the tissue to help anchor the device. Thus, the cartridge member(s) may be configured to penetrate tissue, including bone. In some variations the members are rigid/stiff member and may also include tissue-penetrating distal regions. For example, one or more members may be stainless steel, nickel titanium, or the like (which may be coated with silver in some variations).

Thus, an anti-infection cartridge may comprise silver or a silver coating, plating, or the like. The anti-infective cartridge may be configured to be easily inserted and/or easily removed from the cannulated device (e.g., screw). In some variations, the cartridge has a holding end and a probe end. The holding end may be configured to be readily held, gripped or grabbed by a hand or by a device. By way of example, the holding end may be a loop, V shape or U shape, or may include a grip region. The probe end may be configured to contact a body part or a body solution. In general, the probe end is configured as one or more members that extend from the implant device when it is implanted. For example, the probe end may be configured as one or more members that extend from the screw rod. This may allow the silver ions to be directed to a particular body region, or it may create a larger region of therapeutic silver ions, or it may allow the cartridge to better contact or grip or hold a body surface.

Figure 32B:
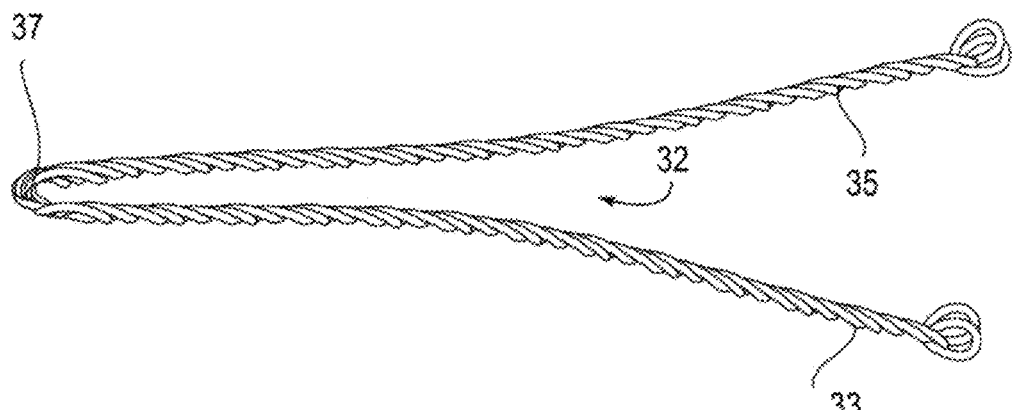

FIG. 32B shows one example of an anti-infection cartridge 32; the proximal end may be referred to as the holding end 37, which can be gripped by a hand or tool. The distal end of the cartridge in this example has two probe ends that can extend out of the body of the screw device. In FIG. 32B, the ends 33, 35 of the two members of the cartridge 32 can be inserted into a screw rod portion of a screw of rod for implantation into the body (bone). In this example the body of the screw rod includes a cathode 22 along the outer surface of the screw; the anodes on the elongate members of the cartridge contact the cathodal surface of the screw when they are extended from the implant. Each probe of the cartridge may have multiple probe ends. The probe ends may be configured to contact a portion of the bone or other tissue to hold the cartridge and bone screw in place. The probe ends may be positioned (spread apart) to create a larger area of effective silver ion area.

Figure 33:
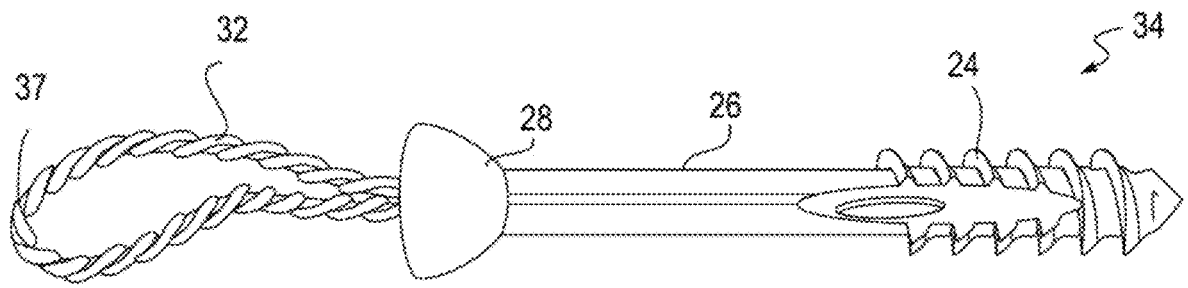
FIG. 33 shows another variation of an implant as described herein.
Figure 34:
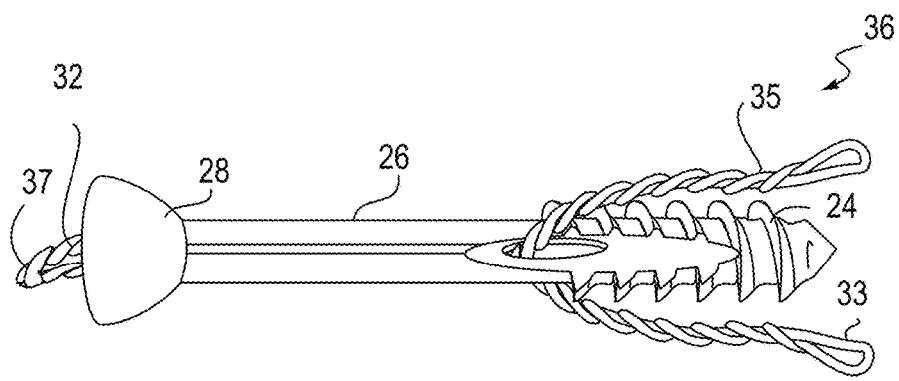
FIG. 34 shows the implant of FIG. 33 in a deployed configuration.

The anti-infective cartridge may be placed in contact with a screw rod to generate a galvanic screw in variations having the anode(s) on the cartridge and the cathode on the body of the implant (e.g., screw). For example, FIGS. 33 and 34 illustrate placement of an anti-infective cartridge 32 such as the one shown in 32B in contact with a screw body such as the one shown in FIG. 32A. The cartridge arms are extended in FIG. 34. In this example the cartridge includes two members, each formed of the twisted wires shown. In one variation the wires are both silver wires; alternatively one wire may be silver and the other wise stainless steel or the like, adding column strength for insertion, such as may be helpful for use in bone. For example, in FIG. 33 the probe ends of the cartridge pass through the center of cannulated screw rod 26 and may be held there until they are deployed into the tissue. When they are deployed (e.g., after implanting the device into the bone) the implant may include deflection/guide regions that steer the members out of the implant and into the tissue. For example, the threads 24 of the screw body in FIGS. 33 and 34 may receive or guide the probe ends as they exit. As the cartridge 32 is advanced, probe ends 33 and 35 exit through openings 30 in the screw body. As mentioned, extending the probes into the tissue may provide mechanical resistance to inhibit unwanted removal or movement of the probe and/or screw. In some variations the distal end of the probes may be sharp or otherwise tissue penetrating.

A biopsy cartridge may share many similarities with an antimicrobial cartridge as described above. For example, the biopsy cartridge may include one or a plurality of members configured to extend from the body of the implant device (e.g., arms, struts, etc.). In some variations the distal ends of these members may include one or more tissue capture elements such as a cup, hook, scraper, basket, needle, etc. A cartridge (including a biopsy cartridge) may also include an attachment site or coupling for a proximal handle (e.g., a threaded region or the like). In some variations a biopsy cartridge may be paired with an antimicrobial cartridge and the two may be exchanged from the same implant device. For example, the implant device (e.g., screw body) may be inserted and an antimicrobial cartridge and a biopsy cartridge may be alternately inserted to sample, then treat, then sample (in any appropriate order) the bone. In some variations the members of the biopsy device are longer (or are capable of extending to a longer length) than the members of the antimicrobial cartridge, to sample bone regions beyond the sites in which the members of the antimicrobial cartridge resided. In some variations the insertion length of the cartridge member(s) is variable, and may be selected or modified by a user when inserting or deploying the cartridge.

FIGS. 37A-C, 38A, 38B, 39A, and 39B describe another embodiment of a galvanic screw system for treating or preventing infection. These systems typically include a support device body (e.g., screw or rod body) and one or more cartridges, as described above. A screw system may have a collapsed or un-deployed configuration and an expanded or deployed configuration. In some variations, toggling between the deployed and un-deployed configurations controls the galvanic potential. For example, in some variations, extending the members of the cartridge including the silver anode may start the galvanic current by placing the anode in electrical contact with the cathode.

Additionally, because of the relatively streamlined initial size/shape, the un-deployed configuration of the system/device can readily be inserted into a bone in a less invasive way and expanded into the deployed configuration once it is in place, limiting any damage or trauma to the tissue.

When the screw is in an un-deployed configuration, the galvanic potential is essentially off. When the screw is in an expanded position, the cathode and anode are in electrical contact with each other and the galvanic potential is on. As the amount of silver in the implant may be limiting, it may be useful to keep a galvanic potential turned off when it is not needed and conserve the potential for future use. The implant may be kept in the collapsed (off) or partially collapsed (off) configuration for any reason. For example, the implant may be configured to be switched "off" (stopping the galvanic release of silver) if there is no evidence of a current infection, but a future infection may be expected, as might be the case in a joint implant. Joint implants have been reported to develop infections months or years after being implanted. By implanting one of the devices as described herein for controllably delivering silver, but leaving galvanic potential "off", the implant may conserve the silver for use if and when an infection develops.

Thus the devices and systems described herein may be configured to allow the anode to be electrically isolated from the cathode (switching "off" the delivery of silver by the device) until it is desired to be controllably released. For example, the electrical connection between the anode and the cathode may depend upon the extent to which a cartridge having members is extended from the body of the device. In some variations, a conductive bridge (e.g., switch) between the anode and cathode may be moveable into and out of position to turn "on" or "off" the galvanic reaction. This is described below in reference to FIGS. 42A-42B. In other variations a switch is not necessary, as the anode and cathode may be place in electrical connection by fully or partially deploying the cartridge (e.g., the members of the cartridge); in the un-deployed configuration the anode may be electrically isolated from the cathode.

In some variations, the activation of the silver release from the implant may depend upon controlling exposure of the anode and/or cathode (which may be in electrical contact) to an electrolytic solution. For example, the cathode and/or anode may be retracted into the fluid-impermeable body of the device until it is desired to release silver ions.

Note that the controllable release of silver as described herein may also refer to the controllable distribution of silver released into the body. In some variations the pattern of distribution of the silver in the body may be determined in part by the arrangement of the member in the deployed configuration. As the members are expanded away from the body of the device (e.g., the screw body or rod body) a much larger pattern (e.g., "cloud") of silver ions having antimicrobial effects at a larger concentration could be achieved than in comparison to an implant or device having only a coating of silver, even actively released silver. In some variations, the implant may be configured to allow control of the extent of the deployment of the members; for example, extending the device only partially from the body of the device as illustrated in FIGS. 37A-38B.

Figure 37A:
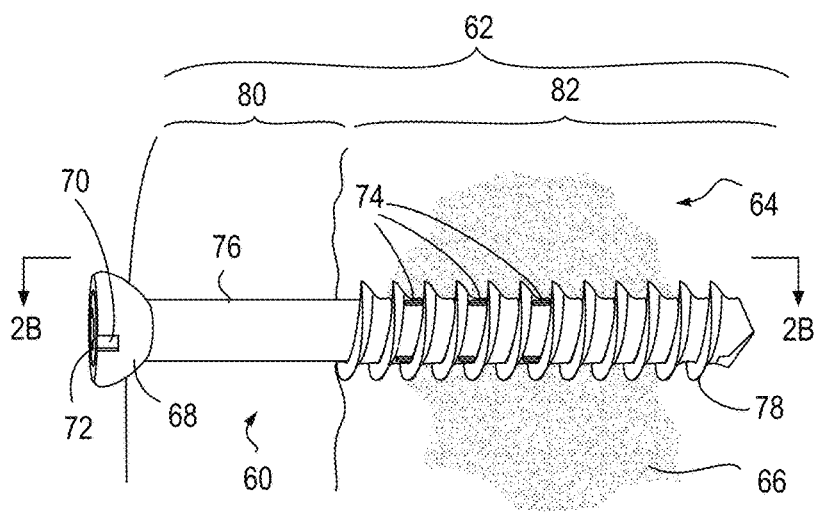
FIGS. 37A-37C illustrate deployment of a silver eluting bone implant as described herein.
Figure 37B:
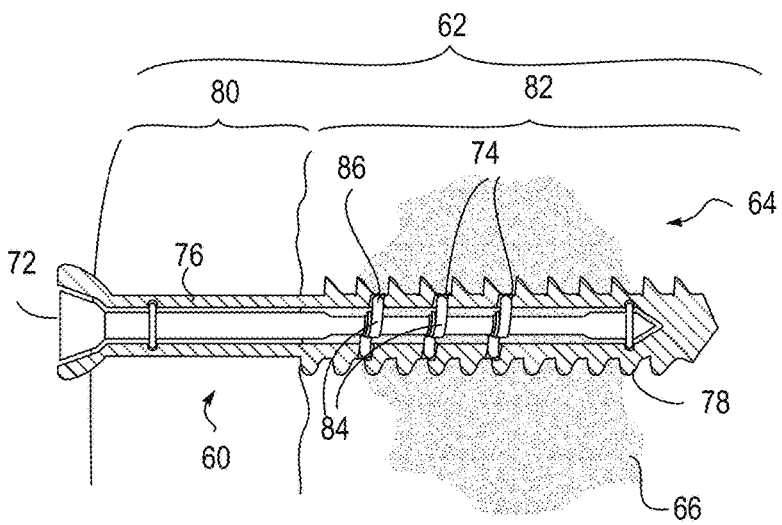
Figure 37C:
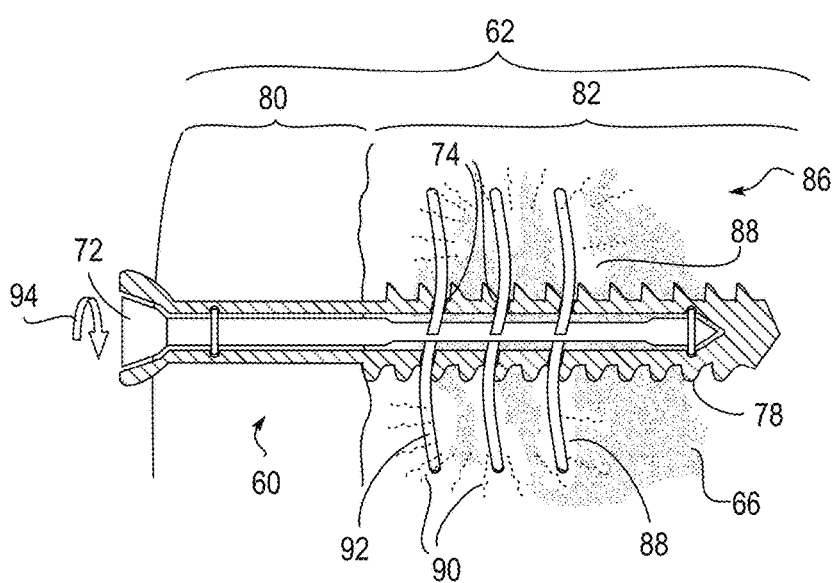

FIGS. 37A-37C show a device for controllably delivering silver ions that is configured as a screw 60; in this example, the screw has been inserted in a bone 62 having an infected region 66. The implant is bathed in a body fluid 64. FIGS. 37B-37C show views along line 32B of FIG. 37A, showing the internal cannulated passage through the elongate screw body 76. The implant is anchored in cancellous bone 82 initially by threaded portion 78, with the rest of implant body 76 in this example positioned within the cortical bone 80. In this example, six members formed as anodes (silver containing regions) are configured as ribbon coils 84 that can be rotated to deploy them out of openings 74 on the body of the screw. The ribbon coil 84 is held inside rod screw 60 near slots/openings 74 between threads 78. These deployable members are part of the loaded (e.g., preloaded) antimicrobial cartridge 72. The cartridge may be rotated when positioned within the screw body to deploy the members from the screw and into the tissue. The device also includes a screw head 68 at the proximal end and a deployment trigger 72 which is configured as a trigger head 72 in this example. Screw head 68 has slots 70 which can be used to insert (e.g., screw in) the screw into the bone, and/or to hold screw body when manipulating trigger head 72 or can be used to otherwise insert, remove, or manipulated the screw.

In the exemplary device shown in FIGS. 37A-37C, the silver releasing members of the cartridge may be deployed by rotating the trigger. Referring to FIG. 37C, the trigger head 72 may be rotated (e.g. counterclockwise), causing ribbon coils 84 to move into position under slots 84 and to unfurl to form probes 88 that extend from the elongate body of the screw. As the members extend from the body, silver on the members (forming a cathode) is placed in electrical contact with the cathode formed on the outer surface of the screw body 76; thus the galvanic potential is on, and silver may be released into the tissue that is bathed in the electrolyte solution (e.g., blood). Thus, members 88 include a silver-releasing anode that is electrically communicating with the platinum cathode on the screw body 76. In this manner, silver ions may be released in a region surrounding the implanted screw body, and silver ions 90 may clear infection 66 to create a clear zone 88 in tissue around the implant.

In the example shown in FIGS. 37A-37C the device for antimicrobial silver release may include a cartridge having the coiled arms that can be extended from the body. In some variations, the cartridge is integral with the body of the device. For example, in FIGS. 37A-37C the cartridge comprises the inner rod member connected proximally to the trigger; the cartridge includes the coiled member wrapped around the inner rod member. The inner rod member may be rotated within the body. In some variation the inner rod member is permanently fixed within the body of the device. In some variations the inner member forming the rotatable may be removable from the body of the device. Thus, the inner member may be recharged and/or replaced while leaving the screw within the patient's bone.

Figure 38A:
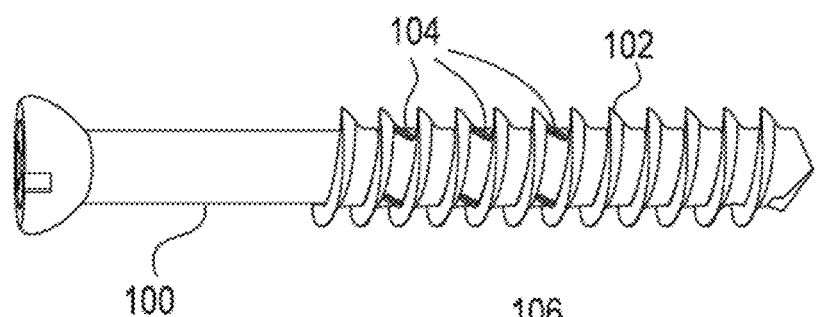
FIGS. 38A and 38B illustrate deployment of another silver eluting bone implant.
Figure 38B:
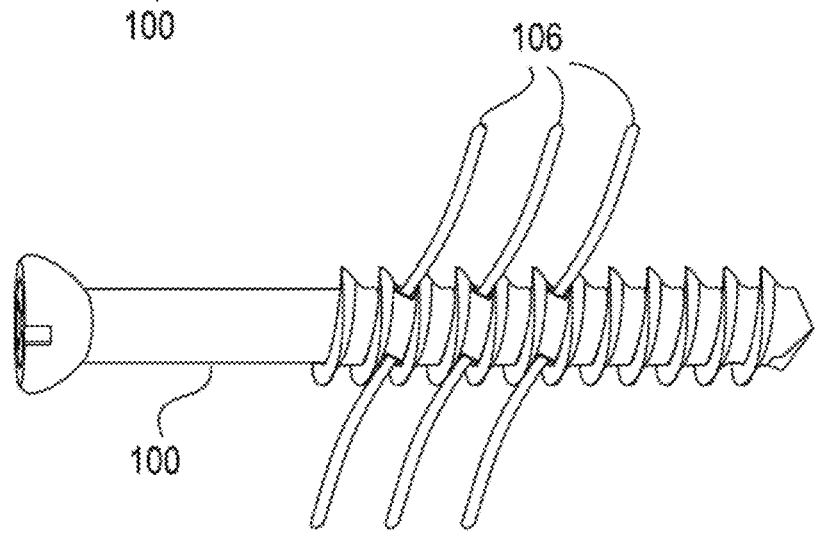

FIGS. 38A and 38B show another variation of a device configured as a screw similar to the one in FIG. 37A-C with tilted slots 104 between threads 102 on rod region 100 in order to bias ribbon coil 106 to exit the body at an angle. In general, the device body may include one or more guides, channels, or the like for directing the members ("ribbon coil 106") from the cartridge (e.g., inner rod) away from the body of the device at an angle or along a pathway. For example, in some variations the device's threads near the distal end of the device may be used to deflect and direct the extending members and thereby control the extent and location of antimicrobial "cloud" surrounding the implant as the ions are released.

Figures 39A, 39B:
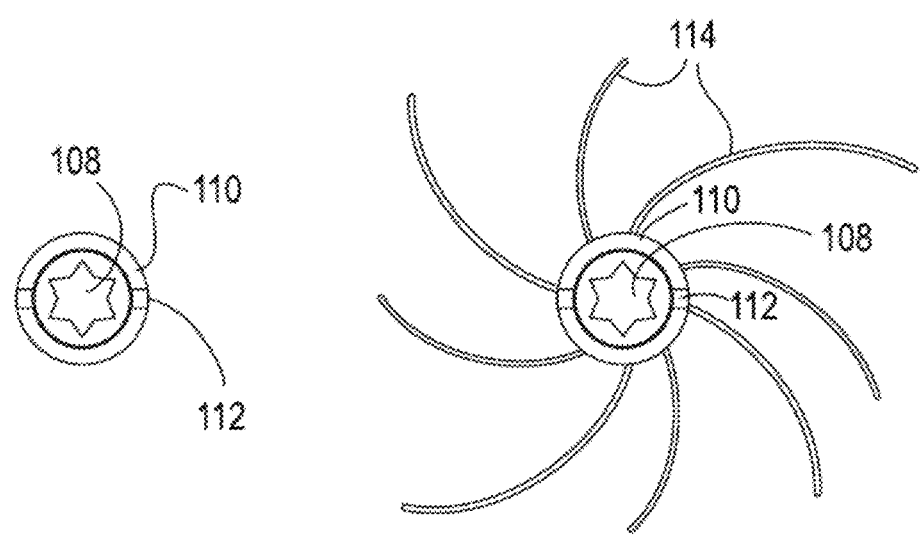
FIGS. 39A and 39B show a top view of an implant in a deployed an un-deployed configuration.

FIGS. 39A and 39B show a top view of another variation of a device configured as a screw similar to the ones shown in FIGS. 37A-38B. This variation includes more members (probes 114), which may be distributed more tightly or specifically around the device. In this example, the trigger head 108 is shown inside rod screw head 110. Slots 112 on screw head 110 can be used to hold the device head 110 relative to trigger head 108 to manipulate the trigger relative to the screw, or screw relative to the bone. In another example, the interior surface and/or outer surface of the screw head 110 may be shaped to engage and/or be grippable by a cannula or other insertion/removal device during screw insertion, removal, or repositioning. The internal shape of the proximal end of the device may be any shape that allows an insertion/removal device to grip the internal surface and to move (e.g. rotate) the screw. The internal shape may be, for example, hexagonal, square, triangular, or threaded. The internal shaping may be only in the head or may extend through part or the entire length of the screw. Being able to grip more than just the head of the screw may better distribute force applied (e.g. torque) to move the screw (e.g., during insertion, removal or repositioning) and thereby prevent the screw from breaking, stripping, or otherwise being damaged. When the multiple arms (probes, coils, etc.) are extended into the tissue (e.g., bone) from within the bone implant device, these member may (in addition to releasing silver) provided additional anchoring to the implanted device. For example, the extended/deployed arms provide mechanical resistance to inhibit unwanted removal or movement of the device.

Figure 40A:
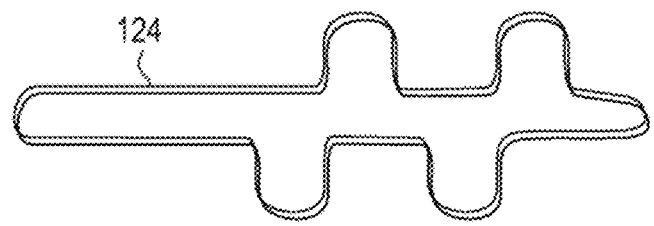
FIGS. 40A-40D illustrate variations of silver eluting bone implants as described herein.
Figure 40B:
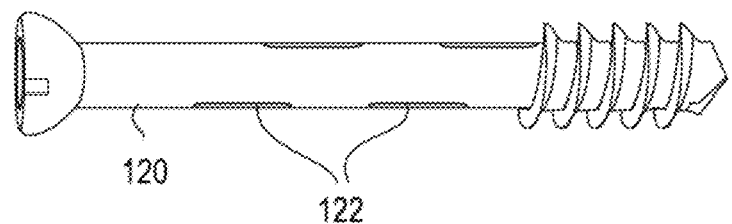
Figure 40C:
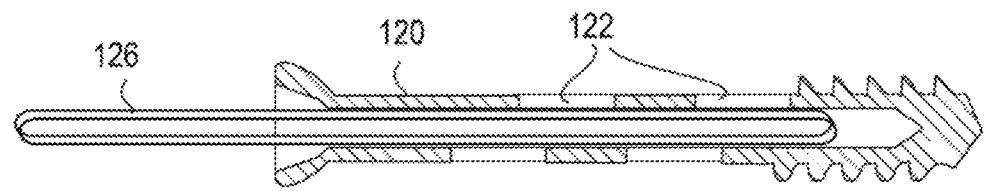
Figure 40D:
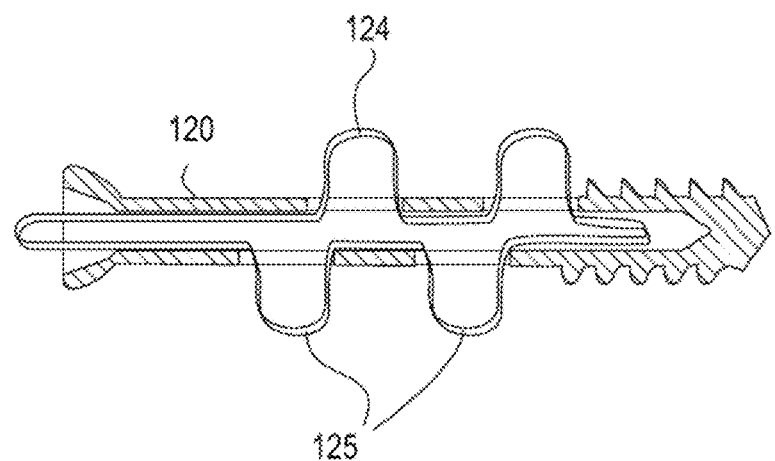

In general, the cartridges described herein can be assembled from any materials that will allow them to be deployed from an implanted device and release silver ions and/or remove (biopsy) tissue. For example, FIGS. 40A-40D show a device, configured as a screw, and a cartridge, formed from a memory shaped ribbon. FIG. 40A shows the shape of the ribbon 124 and the screw device 120. In this example, ribbon 124 collapses to assume collapsed configuration 126 as it's inserted into housing 120. Collapsed ribbon 126 is pushed or turned into position so that probes 125 can expand through slots 122.

Figure 41A:
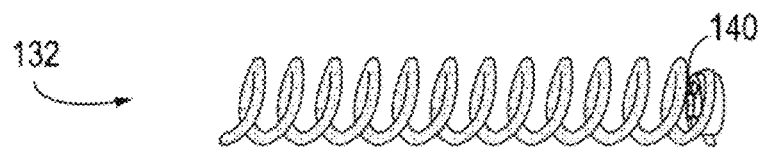
FIGS. 41A-41C illustrate another variation of an implant.
Figure 41B:
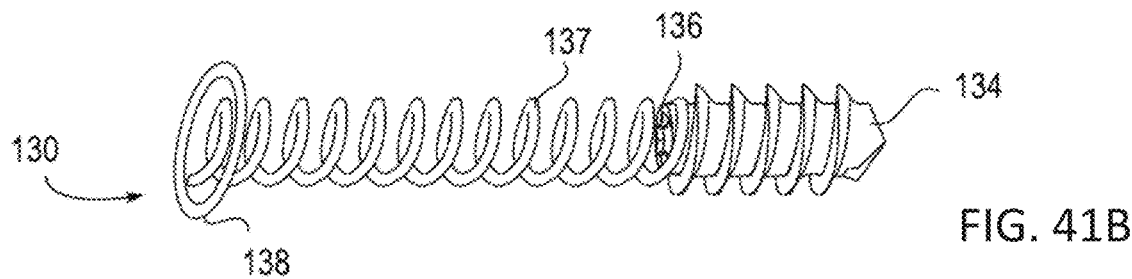
Figure 41C:
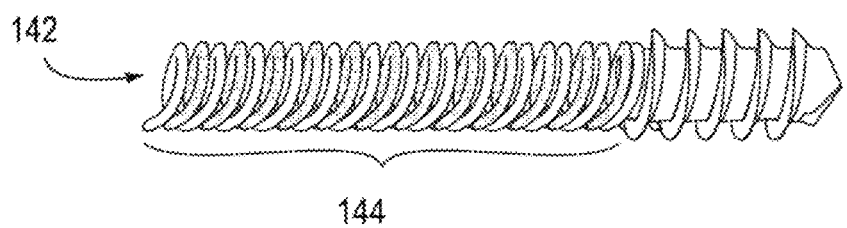

Bones that have been subject to mechanical trauma, infection or other forms of insult may be prone to further damage during insertion of a bone screw. Inserting a bone screw with mechanical properties that are closer to those of bone may reduce or prevent further trauma. FIGS. 41A-C show a bone screw in which the mechanical properties of the bone screw are relatively similar to the mechanical properties of the bone, but which is still able to generate therapeutic silver ions. In this example the elongate body of the device 130 includes a threaded distal end region and a proximal spring region. The device is shown in FIG. 41B and the cartridge for use with the device is shown in FIG. 41A. FIG. 41B shows a platinum (or platinum coated) screw with a threaded distal end 134 and a proximal spring end 137. Screw end 134 may be inserted into a bone by turning hex 136 with a driver. In any of the variations described herein, an initial (e.g. pilot) passage into the bone may be drilled or otherwise formed before implanting the device. Stop 138 may be used to prevent the screw from being inserted too far into the bone. Once rod screw 130 is in place, a cartridge comprising, in this example, a silver screw or spring 132 as shown in FIG. 41A can be screwed into rod screw 130. The result is the two springs coiled together 144 as shown in FIG. 41C. The contact between the platinum or platinum coated coiled region of the device body 137 and the coiled and silver or silver coated region of the cartridge 132 is sufficient that when in the presence of an electrolytic solution, silver ions will be released from the implant.

Figure 42A:
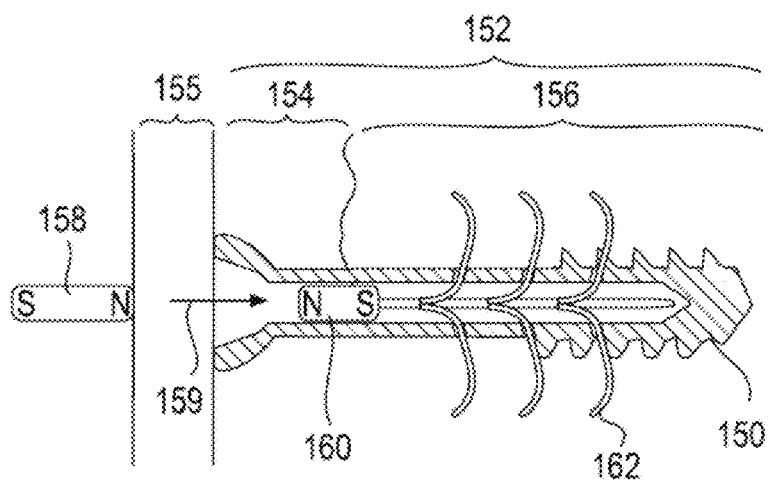
FIG. 42A shows another variation of a silver-eluting implant in a deployed and activated configuration (e.g., with silver release members extended into the tissue)
Figure 42B:
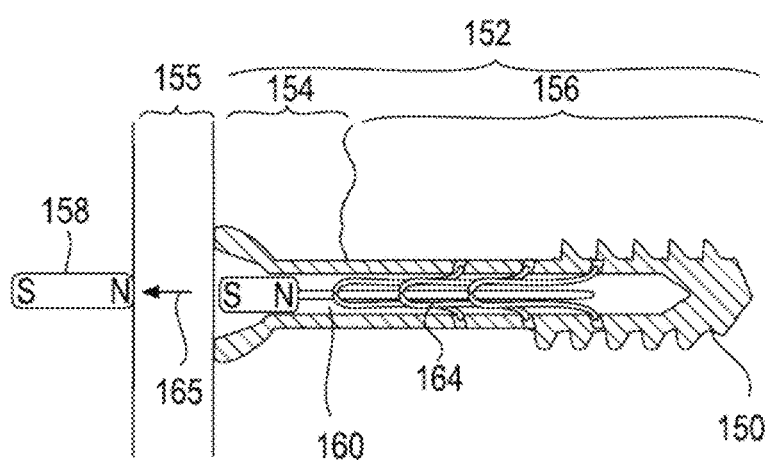
FIG. 42B shows the same implant in a de-activated configuration, in which the silver release members have been withdrawn into the lumen/channel of the implant.

Another example of a trigger or switch for controlling the release of silver ions (e.g., for creating a device having a controllable on/off application of silver ions) uses a magnet as shown in FIGS. 42A-42B. In this example a control magnet is shown outside the body, external to skin 155 while screw 152 is shown screwed into cortical 154 and cancellous 156 regions of bone 152 in the body. Application of external magnetic force (e.g., magnet 158) repels or attracts a corresponding magnetic region within the implant 160, causing it to move the cartridge 162 into or out of position to expand probes 162 out of screw 150 or retract them into the screw. For example, in FIG. 42B, application of external magnet 158 attracts the internal cartridge implanted with the screw, causing it to move the cartridge 164 towards it in a contracted position. Lateral movement of the cartridge results in extending or retracting the members of the cartridge into and out of the screw body, thereby turning on or off the release of silver ions from the screw.

Figure 43A:
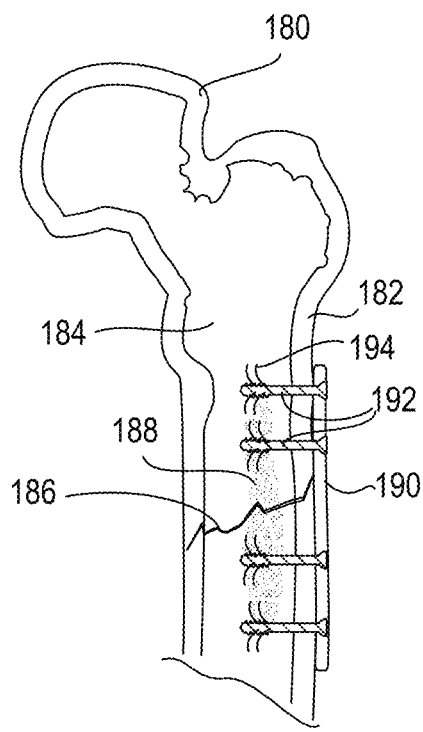
FIGS. 43A and 43B illustrate two variations of silver eluting bone implants as described.
Figure 43B:
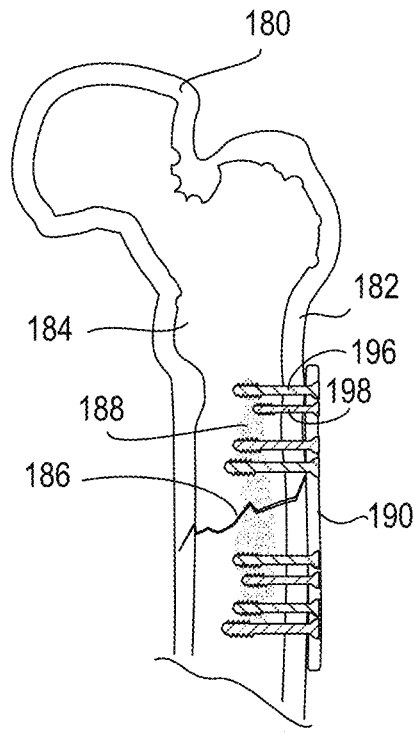

In use, several bone screws can be used together for larger bones or bones otherwise requiring more support or treatment as shown in FIGS. 43A-43B. For example, FIG. 43A shows a series of bone screws 190 inserted through a bone plate 190 that is adjacent to a cortical bone 194 and treating large infection 188 near fracture 186 in femur 180. Each screw has multiple silver-releasing members 194 extending into cancellous bone 184 to create a large silver therapeutic area. FIG. 43B shows an alternative embodiment in which some silver/silver coated rod screws 196 are alternating with platinum plated or noble metal rod screws 198.

Figure 44:
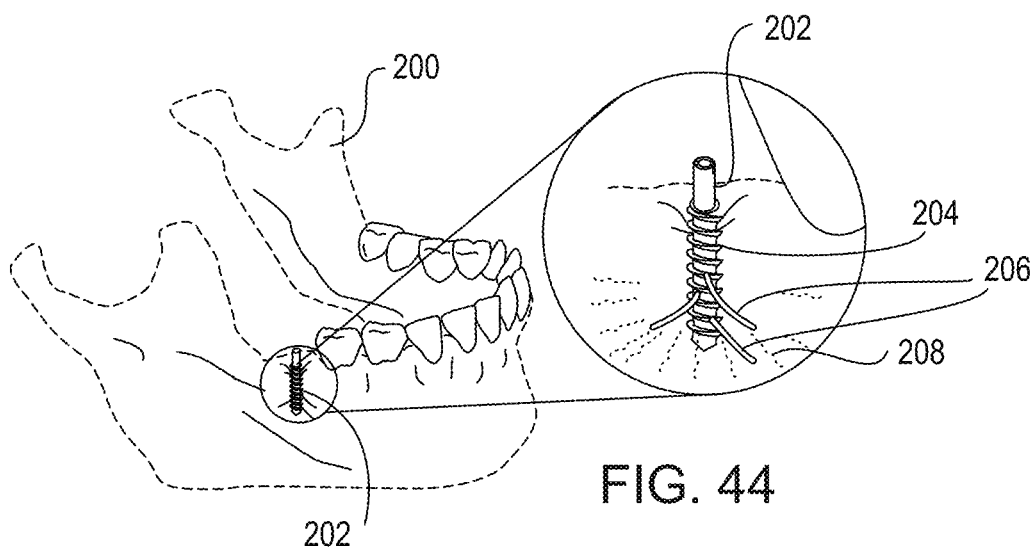
FIG. 44 illustrates another variation of an implant configured for use as a dental device. Similarly.
Figure 45:
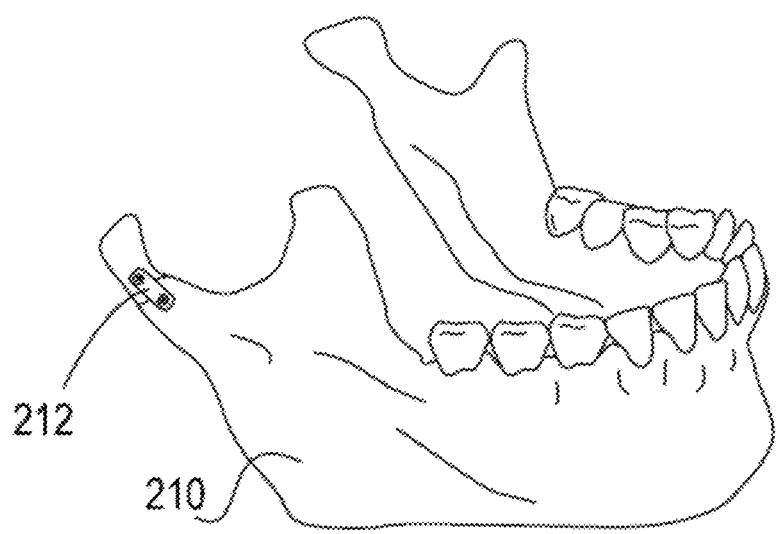
FIGS. 45 and 46 illustrate variations of silver eluting bone implants configured to treat other bone regions, including the jaw and skull (face), respectively.
Figure 46:
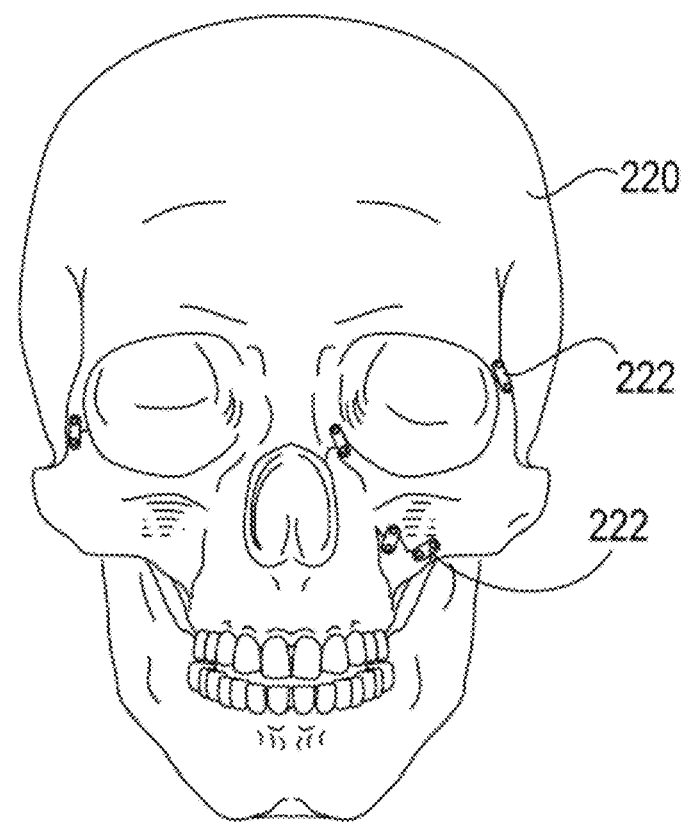

The bone screw, methods, and systems described herein may be used with any type of bone, including long bones. FIG. 44 shows a bone screw 202 configured to release silver ions similar to those in FIGS. 32A-33B above, inserted into a portion of a jaw. Therapeutic silver ions 206 are released from members 206. The screw may be configured to attach a tooth, crown or other dental appliance. FIG. 45 shows bone screws and a plate attached to a mandible such as might be used in a reconstructive surgery to prevent or treat infections. FIG. 46 shows bone screws and plates used in various bones of the jaw, face, and skull 220.

In some variations, the anti-infective cartridge includes a lock on the cannulated screw and/or rod to hold the cartridge in place relative to the elongate body of the device. Thus, the cartridge may be locked in a configuration (e.g., deployed, un-deployed, etc.) within the body of the device. The lock may be releasable; for example, the lock may include a latch.

As mentioned above, the cartridge may be configured as a biopsy (e.g., assay) cartridge, which may be used instead of, or in addition to an anti-infection cartridge; in some variations the cartridge is a combination of both anti-infective and biopsy. In general a biopsy cartridge may be coupled to the body of the device and used to withdraw a sample of tissue from around where the implant has been inserted without having to remove the device ("implant") from the body. For example, in some variations, the biopsy cartridge is inserted through the cannulated elongate body of the device (e.g., of a screw body) and one or more members of the cartridge extends from the elongate body, similar to the silver-releasing members extending from the silver-release cartridges described above, to make contact with a portion of the body to be assayed, to obtain a biopsy (assay) sample, and to be removed. The biopsy sample can be assayed in any way after being removed from the patient. Thus, the biopsy cartridge may have an expanded (deployed) form and a collapsed (un-deployed) form. The biopsy cartridge may be expanded before obtaining a biopsy sample and may be collapsed after obtaining a biopsy sample. Any of the structures described in the disclosure for the anti-infective cartridge and any of the methods described for inserting, using, or removing the cartridge may also or instead be used for the biopsy cartridge.

Although many of the examples described above are configured so that the device body is configured as the cathode (e.g., comprising a platinum material) while the extendable members from the cartridge are the anode material (e.g., silver or silver coated), in some variations this configuration may be reversed. For example, the device body (e.g., the screw body, rod body, etc.) may be silver or silver coated and the anti-infective cartridge may configured as the cathode, comprising a noble metal such as gold, palladium or platinum to create a galvanic response in the body and release silver ions.

In general, the devices may be inserted or implanted into the body, e.g., into the bone, either before during or after engaging a cartridge, including an anti-infective and/or biopsy cartridge. For example, a device configured as a silver-delivering screw may be inserted into a bone, loaded with an anti-infective cartridge or biopsy cartridge by inserting the cartridge through the elongate body (e.g., from the proximal end of the screw rod). A biopsy cartridge may be inserted and removed before, after, or instead of insertion of an anti-infective cartridge. In one example, a biopsy cartridge is inserted through the device body, takes a biopsy sample, and is removed before anti-infective cartridge is inserted. In another example, an anti-infective cartridge may be inserted, left in the body for a period of time to create therapeutic silver ions, and removed before a biopsy cartridge is used to remove a biopsy sample to determine an effectiveness of anti-infective treatment. In another example, an anti-infective cartridge may be inserted, left in the body for a period of time to create therapeutic silver ions, and removed before a biopsy cartridge is used to remove a biopsy sample to determine an effectiveness of anti-infective treatment.

In another example, a first anti-infective cartridge is placed through the device implanted in the body and one or more anti-infective cartridges are additionally placed in the device body, without removing the first anti-infective cartridge. The cartridges may degrade (e.g., corrode as the silver is release) or simply avoiding by preceding cartridges.

In another example, a first anti-infective cartridge may be removed from an implanted device in a body and a second anti-infective cartridge inserted. This process may be repeated. This may be done, for example, if there is insufficient therapeutic silver remaining on a first cartridge. The screw rod and any of the cartridges may be left in the body for any length of time. They may be left in for less than thirty days (e.g. a few days, a week, or several weeks) or they may be left in for more than thirty days. In one example, the screws may be left in permanently.

Examples

Any of the exemplary ion-releasing devices described above may be used to treat (or prophylactically treat or prevent) infection and/or support tissue. Exemplary methods of use are illustrated below. These examples are intended only to illustrate how one such implant may be operated, and is not intended to be limiting or limited to any specific variation.

In general, the implants for controllably providing antimicrobial treatment and support may be used to treat any tissues of the body, but particularly bones, including the long bones (such as the femur, tibia, radius, ulna, fibula, metacarpal, metatarsal, phalanges, etc.), the spine, and the skull. In some variations the device is configured for insertion into the medullary canal of a lower extremity bone, such as a femur, tibia, tarsal or metatarsal, for the alignment, stabilization, fixation and bone biopsy of various types of fractures or deformities caused by trauma, infection or disease. Examples of such fractures include: traumatic fractures, re-fractures, non-union, reconstruction, malunion, malalignment, pathological fractures due to infection or disease and impending pathological fractures. The ion controlled release systems may have silver and/or zinc coated struts that expand out from the body of the device to form a three-dimensional array to stabilize, minimize device migration and form an antimicrobial barrier to reduce microbial colonization on the external surfaces of the device.

An implant that controllably provides antimicrobial treatment, such as a bone screw for controllably releasing silver ions, may be used to repair a bone fracture. The bone may first be prepared to receive the device. Pre-existing deformities may be corrected prior to the preparation and insertion of a device such as those described above configured as a controllable silver-ion releasing bone screw (e.g., intramedullary or IM screw). The anatomy of the deformity, surgeon preference, and patient positioning may determine the appropriate approach chosen for joint preparation and alignment.

For example, a bone implant that controllably provides antimicrobial treatment may be use used to repair a broken ankle. Upon properly aligning and preparing all the joint surfaces, the ankle may be positioned for arthrodesis. The ankle may be medizlized by thorough debridement of medial gutter facilitates positioning in the center of the calcaneus, talus and tibia. The ankle may then be placed in neutral dorsiflexion and symmetric external rotation of the contralateral ankle. This position may be maintained throughout the procedure, and may be facilitated by provisionally placing a wire on the periphery of the ankle joint.

Under fluoroscopic control, a 2-3 cm longitudinal incision may be made just above the location for the bone insertion point. After the incision is made, dissection may be continued down to the surface of the target bone by bluntly dissecting through the soft tissues, noting the location of neurovascular bundles. Thereafter, the device (e.g., a controlled silver ion releasing implant or bone screw) may be inserted. An introducing cannula can then be selected and placed against the bone insertion point. The hand reamer may then be used to carefully ream through the cortical bone into the intramedullary canal. The cannula is not advanced into the bone. The position of the hand reamer under fluoroscopy may be monitored under floro periodically. The hand reamer can be removed from the cannula.

Thereafter, the surgeon may select the proper size implant device IM screw rod that is pre-mounted on trocar. Advance the screw rod into the bone by turning clockwise. Periodically stop and check under fluoroscopy the position of the screw rod with respect to the opposite cortical side.

Finally, the trocar device may be removed from the inside of the cannulated screw rod by turning clockwise.

In some variations, the bone implant that controllably provides antimicrobial treatment may also be used to take a biopsy before, during or after insertion of the implant. The implant may be inserted into the bone as discussed above, and a bone biopsy cartridge may be inserted through the internal cannula of the implanted device. The proximal end of the cartridge may be grasped direction of coupled to a handle for manipulation by a surgeon. The distal end of the biopsy cartridge may include one or a plurality of cupped wires that can be extended from the implant body and used to sample the tissue. For example, one or more cupped wires may be deployed through the ports of the body of a screw-type implant. This may be met with some resistance from the cancellous bone. Extension of the biopsy cup wires can be confirmed by fluoroscopy. After deployment of the wires, the proximal end of the cartridge may be pulled back and the wires retracted, capturing cancellous bone for biopsy in the cups of the cartridge. The cartridge may be removed from the rest of the implant, and placed in a sealed, labeled laboratory infectious disease container for further processing.

In general, the antimicrobial cartridges described herein may be inserted and/or deployed as mentioned above. For example, a cartridge may be removed from a foil sterile package. The cartridge may be stored in a sealed package with an indicator to indicate if the package integrity has been compromised. For example, the package may include an indicating desiccant (e.g., pouch) that visually indicated, e.g., by a line that changes red, if the packaging has been breached and exposed to humidity.

The cartridge may be inserted into the device housing, e.g., the central bore or cannula within the elongate cannulated body. In some variations the cartridge is pre-loaded into the body of the device. The cartridge, and particularly the elongate members of the cartridge at the distal end, may be inspected and/or aligned with the cannulated body so that they may be extended through openings in the body to extend from the body when implanted. The cannulated body may include a guide, channel, keying, etc. to aid in aligning and inserting the cartridge into the body. In some variations the inner surface of the cannulated body is keyed (including threaded) to guide the insertion of the cartridge; an outer surface of the cartridge may mate with and engage the inner surface of the cannulated body.

An insertion tool (e.g., handle) may be used to help insert the cartridge into the elongate cannulated body of the implant. For example, the insertion/removal tool may be an elongate rod having a coupling and or mount its distal end region to connect to a cartridge. In some variations the insertion/removal tool may include an inner body region for holding the cartridge in the collapsed/un-deployed configuration after or before it has been connected/removed from the implant body. For example, the cartridge may be "collapsed" by the action of the insertion tool. The distal end of the insertion tool may include a chamber, cannula, etc. for holding the cartridge in a collapsed configuration; the cartridge may be pushed out of or otherwise extended from the handle into the implant, allowing the members of the cartridge to extend through the body of the device and into tissue.

Thus, the distal ends of the members may be extended away from the body of the implant and into the patient tissue so that the members will deploy through the ports of the device. In some variations this deployment is guided by the implant body which deflects and/or guides the members as they are extended. For example, the threads of an implant configured as a bone screw may be arranged to deflect the members outward and into the tissue. After insertion and/or deployment of the cartridge in variations requiring it, any inserter tools may be withdrawn and proper positioning may be confirmed using fluoroscopy.

Thereafter, the stability and operation of the device may be verified, and the surgical access/insertion site may be closed, at least for some amount of time. In some variations the cartridge may be replaced/recharged into the same implant over the course of weeks, months or years.

Once the implant has exceeded its useful life, it may be removed from the patient or left in place. In some variations it may be desirable to leave the implant in place so that it can continue to provide structural support. This may be true even of the cartridges, as any extended members that have been extended into the tissue may continue to provide structural support even if the source of silver ions has been exhausted.

The cartridges may be removed in many cases by reversing the insertion process just described. In some variations the cartridge may remain within the bone for approximately 30 days or more. The implant may be removed with a removal device configured to couple to the proximal end of the cartridge and/or to release the cartridge from the device body.

In some variations a retrieval kit may be used. For example, a retrieval kit may include a removal device (configured similarly to an inserter). To remove the device, surgical aseptic technique (under fluoroscopy) may be used to make a small incision directly above the site of the previous surgery. The removal device (cartridge retrieval device) may be inserted and attached to the proximal end to the outer housing to stabilize it. In some variations the retrieval device has an elongated body with a distal end that is adapted to couple or abut (e.g., adjacently contact) the implant device body and a second region that is configured to couple with the proximal end of the cartridge. For example, the retrieval member may include a central shaft having a distal end adapted to couple (e.g., screw onto) the proximal end of the cartridge and an outer cannula surrounding the central shaft that is configured to couple to the proximal end of the implant device. In some variations the retrieval device includes a proximal forceps that may be used to couple to the inner cartridge. Such configurations (or similar configurations) may allow sufficient leverage to remove the extended members and withdraw the cartridge form the implant and the body, retracting the members through the outer housing ports and collapsing them for removal.

After removal, the cartridge may be disposed of or used to provide biopsy material. The surgical site may be examined directly and by fluoroscopy. If it appears that the site (and implant) would benefit from additional anti-migration or anti-infection elements, a new cartridge may be re-deployed for another treatment period (e.g., 30 days) and the process repeated.

Although the illustrations described above illustrated primarily threaded screw variations, it should be apparent that non-treaded variations and non-screw variations are contemplated. For example, the devices for controllable release of silver ions described herein may be configured as nails, rods or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An implantable device comprising:
a device body formed of a substrate;
a coating on the device body, the coating comprising a mixture of an anodic metal and a cathodic metal, wherein the mixture of the anodic metal and the cathodic metal comprises a plurality of microregions or microdomains of anodic metal in a matrix of cathodic metal or a plurality of microregions or microdomains of cathodic metal in a matrix of anodic metal, the microregions or microdomains forming interconnected veins of anodic metal through a thickness of the coating, or interconnected veins of cathodic metal through the thickness of the coating, so that the anodic metal is galvanically released as antimicrobial ions when the device body is exposed to a bodily fluid.

2. The device of claim 1, wherein the device body comprises a graft.

3. The device of claim 1, wherein the substrate is of one or more of: Polyglycolide (PGA), poly(lactic-co-glycolic acid) (PGLA), a bioabsorbable mesh or a metal.

4. The device of claim 1, wherein the mixture of the anodic metal and the cathodic metal forms a pattern.

5. The device of claim 1, wherein the mixture of the anodic metal and the cathodic metal forms one or more of: a sinusoidal pattern, cross-hatched pattern, a mesh pattern, a web pattern, or a zig-zag pattern.

6. The device of claim 1, wherein less than 30% of the anodic metal is fully encapsulated within the matrix of cathodic metal and connects through a microregion or microdomain of anodic metal to the outer surface of the device body.

7. The device of claim 1, wherein less than 20% of the anodic metal is fully encapsulated within the matrix of cathodic metal and connects through a microregion or microdomain of anodic metal to the outer surface of the device body.

8. The device of claim 1, wherein the anodic metal comprises both zinc and silver.

9. The device of claim 1, wherein the anodic metal comprises silver, zinc or copper.

10. The device of claim 1, wherein the cathodic metal comprises one or more of: palladium, platinum, or gold.

11. The device of claim 1, wherein the cathodic metal comprises one or more of: palladium, platinum, gold, molybdenum, titanium, iridium, osmium, rhodium, manganese, niobium or rhenium.

12. The device of claim 1, wherein the device body comprises the anodic metal and the cathodic metal that have been vapor-deposited so that the anodic metal is not encapsulated by the cathodic metal.

13. The device of claim 1, wherein the outer surface of the device body is fractured.

14. The device of claim 1, wherein the device body comprises a screw or staple.

15. The device of claim 1, wherein the coating has a thickness that is greater than 2 microns.

16. An implantable device comprising:
a device body formed of a bioabsorbable substrate;
a coating on the device body, the coating comprising a mixture of an anodic metal and a cathodic metal, wherein the mixture of the anodic metal and the cathodic metal comprises a plurality of microregions or microdomains of anodic metal in a matrix of cathodic metal or a plurality of microregions or microdomains of cathodic metal in a matrix of anodic metal, the microregions or microdomains forming interconnected veins of anodic metal through a thickness of the coating, or interconnected veins of cathodic metal through the thickness of the coating, so that the anodic metal is galvanically released as antimicrobial ions when the device body is exposed to a bodily fluid, wherein the coating has a thickness that is greater than 10 microinches.

17. An implantable device comprising:
a device body formed of a substrate;
a coating on the device body, the coating comprising a mixture of an anodic metal and a cathodic metal, wherein the mixture of the anodic metal and the cathodic metal comprises a plurality of microregions or microdomains of anodic metal in a matrix of cathodic metal or a plurality of microregions or microdomains of cathodic metal in a matrix of anodic metal, the microregions or microdomains forming interconnected veins of anodic metal through a thickness of the coating, or interconnected veins of cathodic metal through the thickness of the coating, so that the anodic metal is galvanically released as antimicrobial ions when the device body is exposed to a bodily fluid, wherein the coating has a thickness between 10 microinches and 500 microinches.

* * * * *